(12) United States Patent
Alcouffe et al.

(10) Patent No.: US 9,732,078 B2
(45) Date of Patent: Aug. 15, 2017

(54) THERAPEUTIC USE OF IMIDAZOPYRIDINE DERIVATIVES

(71) Applicant: SANOFI, Paris (FR)

(72) Inventors: Chantal Alcouffe, Paris (FR); Corentin Herbert, Paris (FR)

(73) Assignee: SANOFI, Paris (FR)

( * ) Notice: Subject to any disclaimer, the term of this patent is extended or adjusted under 35 U.S.C. 154(b) by 176 days.

(21) Appl. No.: 14/370,462

(22) PCT Filed: Jan. 3, 2013

(86) PCT No.: PCT/IB2013/050048
§ 371 (c)(1),
(2) Date: Jul. 2, 2014

(87) PCT Pub. No.: WO2013/102860
PCT Pub. Date: Jul. 11, 2013

(65) Prior Publication Data
US 2014/0343054 A1    Nov. 20, 2014

(30) Foreign Application Priority Data

Jan. 4, 2012    (FR) ...................... 12 50075

(51) Int. Cl.
*C07D 471/04*    (2006.01)
*A61K 31/437*    (2006.01)

(52) U.S. Cl.
CPC .......... *C07D 471/04* (2013.01); *A61K 31/437* (2013.01)

(58) Field of Classification Search
CPC ............................ C07D 471/04; A61K 31/437
See application file for complete search history.

(56) References Cited

U.S. PATENT DOCUMENTS

| 8,759,344 B2 | 6/2014 | Alcouffe et al. |
| 2009/0069368 A1 | 3/2009 | Bono et al. |
| 2014/0243328 A1 | 8/2014 | Alcouffe et al. |

FOREIGN PATENT DOCUMENTS

| CN | 1887878 A | 1/2007 |
| WO | WO2006097625 A1 | 9/2006 |
| WO | WO-2007/080325 A1 | 7/2007 |
| WO | WO-2008/012690 A2 | 1/2008 |
| WO | WO-2012/004732 A1 | 1/2012 |

OTHER PUBLICATIONS

Bower, J. D. and Ramage, G. R. "Heterocyclic Systems Related to Pyrrocoline. Part I. 2:3a-Diazaindene" J. Chem. Soc. (1955), 2834-2836 (1955).
di Martino, E., L'Hote, C. G., Kennedy, W., Tomlinson, D. C. and Knowles, M. A. "Mutant fibroblast growth factor receptor 3 induces intracellular signaling and cellular transformation in a cell type- and mutation-specific manner" Oncogene (2009) 28: 4306-4316 (Sep. 14, 2009).
Dodurga, Y., Tataroglu, C., Kesen, Z. and Satiroglu-Tufan N. L. "Incidence of fibroblast growth factor receptor 3 gene (FGFR3) A248C, S249C, G372C, and T375C mutations in bladder cancer" Genetics and Molecular Research 10 (1): 86-95 (2011) (Jan. 18, 2011).
Gwynn, E. S. and Clark, P.E. "Bladder Cancer" Current Opinion in Oncology 2006, 18:277-283 (May 2006).

(Continued)

*Primary Examiner* — Barbara P Badio
*Assistant Examiner* — Sara E Townsley
(74) *Attorney, Agent, or Firm* — Morrison & Foerster LLP

(57) ABSTRACT

The invention relates to the use of compounds corresponding to formula (I) in which $R_2$ and $R_3$ together form, with the carbon atoms of the phenyl nucleus to which they are attached, a 6-membered nitrogenous heterocycle corresponding to one of the formulae (A), (B) and (C) in which the wavy lines represent the phenyl nucleus to which $R_2$ and $R_3$ are attached, or of a pharmaceutically acceptable salt thereof, for preparing a medicament for the treatment of bladder cancer.

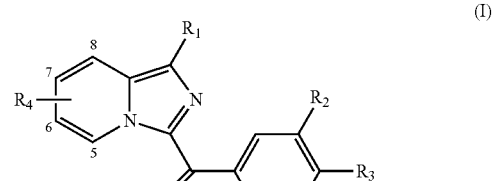

(I)

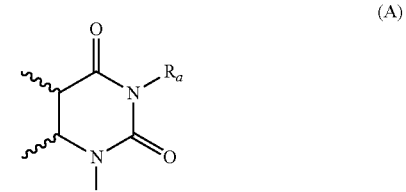

(A)

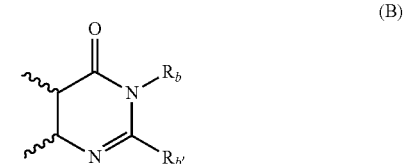

(B)

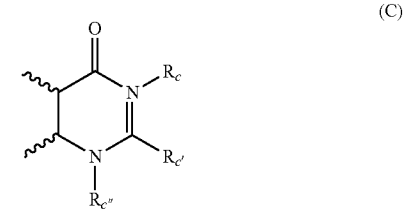

(C)

4 Claims, No Drawings

(56) References Cited

OTHER PUBLICATIONS

Ahmedin Jemal, Taylor Murray, Elizabeth Ward, Alicia Samuels, Ram C. Tiwari, ASMA Ghafoor, Eric J. Feuer and Michael J. Thun "Cancer Statistics, 2005" CA Cancer J Clin 2005;55:10-30 (Feb. 24, 2009).

Knowles, M. A. "Novel Therapeutic Targets in Bladder Cancer: Mutation and Expression of FGF receptors" Future Oncol. (2008) 4(1), 71-83 (Feb. 1, 2008).

Lamont, F. R., Tomlinson, D. C., Cooper, P. A., Shnyder, S. D., Chester, J. D. and Knowles, M. A. "Small molecule FGF receptor inhibitors block FGFR-dependent urothelial carcinoma growth in vitro and in vivo" British Journal of Cancer (2011) 104, 75-82 (Nov. 30, 2010).

Oosterlinck, W., Lobel, B., Jakse, G., Malmstrom, P.-U., Stockle, M., Sternberg, C. "Guidelines of Bladder Cancer" European Urology (2002) 41, 105-112 (2002).

Wolfgang Otto, Stefan Denzinger, Simone Bertz, Andreas Gaumann, Peter J. Wild, Arndt Hartmann and Robert Stoehr "No mutations of FGFR3 in normal urothelium in the vicinity of urothelial carcinoma of the bladder harbouring activating FGFR3 mutations in patients with bladder cancer" Int. J. Cancer: 125, 2205-2208 (2009) (May 28, 2009).

Jing Qing, Xiangnan Du, Yongmei Chen, Pamela Chan, Hao Li, Ping Wu, Scot Marsters, Scott Stawicki, Janet Tien, Klara Totpal, Sarajane Ross, Susanna Stinson, David Dornan, Dorothy French, Qian-Rena Wang, Jean-Philippe Stephan, Yan Wu, Christian Wiesmann, and Avi Ashkenazi "Antibody-based targeting of FGFR3 in bladder carcinoma and t(4;14)-positive multiple myeloma in mice" The Journal of Clinical Investigation (2009) vol. 119 No. 5 (May 2009).

Tomlinson, D. C., Baldo, O., Harnden, P. and Knowles, M. A. "FGFR3 protein expression and its relationship to mutation status and prognostic variables in bladder cancer" J Pathol. Sep. 2007; 213(1): 91-98 (Jul. 31, 2007).

Tomlinson, D. C., Hurst, C. D. and Knowles, M. A. "Knockdown by shRNA identifies S249C mutant FGFR3 as a potential therapeutic target in bladder cancer" Oncogene. Aug. 30, 2007; 26(40): 5889-5899 (Mar. 26, 2007).

Xue-Ru Wu "Urothelial Tumorigenesis: A Tale of Divergent Pathways" Nature Reviews Cancer, Sep. 2005, vol. 5, No. 9, 713-725 (Sep. 2005).

International Search Report for International Patent Application No. PCT/IB2013/050048 dated Feb. 18, 2013 (mailed Feb. 25, 2013).

Non-Final Office Action mailed on May 7, 2015, for U.S. Appl. No. 14/267,272, filed May 1, 2014, 59 pages.

THERAPEUTIC USE OF IMIDAZOPYRIDINE DERIVATIVES

This application is a national stage application under 35 U.S.C. §371 of International Application No. PCT/IB2013/050048, filed Jan. 3, 2013, which claims priority benefit of French Application No. 1250075, filed Jan. 4, 2012, the disclosures of which are incorporated herein by reference in their entirety.

The present invention relates to the therapeutic use of imidazopyridine derivatives which are FGF (Fibroblast Growth Factor) receptor inhibitors, for preparing a medicament for the treatment of bladder cancer.

FGFs are a family of polypeptides synthesized by a large number of cells during embryonic development and by cells of adult tissues under various pathological conditions.

Bladder cancer is the sixth most common cancer in industrialized countries and the fourth in the United States, representing, in the latter country, more than 63 000 cases diagnosed every year and more than 13 000 deaths (Gwynn et al., 2006; Knowles et al., 2008; Jemal et al., 2005). These cancers affect mainly individuals over the age of 50, the population of which is greatly increasing. Throughout the world, at least 300 000 cases are detected each year, and this number is increasing. They are categorized in 2 main groups: i) superficial, papillary and non-invasive forms which do not penetrate the epithelium of the basal membrane or the underlying muscle (papilloma stages Ta and T1; Knowles et al., 2008) and represent between 70% and 80% of diagnosed cases, and ii) invasive forms (stages T2, T3 and T4; Knowles et al., 2008).

Although patients suffering from superficial and non-invasive bladder cancer have a good vital prognosis, this disease often presents multifocal carcinomas, which have a very high rate of recurrence (70%). Current treatment requires repeated and invasive procedures (transurethral resection combined with intravesical instillation of chemotherapy, such as mitomycin B, or an intravesical infusion of a solution of attenuated bacillus Calmette-Guerin (BCG)), each time requiring several days of hospitalization (www.cancer.govicancertopics/pdq/treatment/bladder/Patient/page1).

All these characteristics make this disease extremely expensive by virtue of the medical follow-up that it requires. Furthermore, the current treatments are curative only for a minority of cases (less than 30%) and they cause numerous side-effects, such as pain during urination, nausea, fever, a considerable decrease in the time interval between urinations, bladder irritation, etc. (Oosterlink et al., 2002). Consequently, a curative treatment for bladder cancers while avoiding the numerous side-effects of the current medications is still a necessity.

Recently, a link has been demonstrated between these superficial urothelial cancers (UCs) of the bladder and the expression of a mutated form of FGF receptor 3 (FGF-R3). In this context, a very strong correlation has been made between the expression of mutated forms of FGF-R3 and low grade/stage bladder UCs. These mutations have also been identified in urothelial papillomas, and have been proposed as being responsible for the lesions that are a warning of papillary UCs (Knowles et al., 2008; Wu et al., 2005). The principal mutations are in the extracellular domain of FGF-R3 (75% of cases) at positions Arg248 and Ser249, in the transmembrane domain (25% of cases) at positions Gly372 and 382, Ser373, Tyr375 and Ala393 or else in the tyrosine kinase domain (2.5% of cases) at position Lys652 (Knowles et al., 2008; Dodurga et al., 2011). The two most common mutations are the replacement of Ser249 or of Tyr375 with a cysteine, leading to a ligand-independent constitutive dimerization of the receptor by virtue of an inter-chain disulphide bridge resulting in permanent activation of the receptor and of the underlying intracellular signalling pathways (di Martino et al., 2005; Qing et al., 2009). These "gain-of-function" mutations contribute to the proliferation of tumour cells, and to their ability to grow beyond confluence and to resist apoptosis (Tomlinson et al, 2007b; di Martino et al., 2009; Lamont et al., 2011). Furthermore, it appears that expression of the FGF-R3 protein correlates strongly with the presence of these mutations, with increased expression in the majority of superficial tumours carrying these FGF-R3 mutations (Tomlinson et al., 2007a), whereas these mutated forms are not detected in healthy urothelium (Otto et al., 2009).

The Ser249Cys mutation is the most common mutation in bladder UCs. It is present in more than 70% of the superficial forms of UCs. Reduction of the expression of this mutated form of FGF-R3 using an siRNA approach has made it possible to show that this mutated receptor controls the proliferation and growth of bladder cancer tumour cells independent of attachment to a substrate (Tomlinson et al., 2007b). This mutated form of FGF-R3 therefore appears to be a therapeutic target of choice for the treatment of superficial and non-invasive bladder cancers. The TCC97-7 cell line described in the literature is a relevant line for studying the effect of compounds for treating FGF receptor-3 Ser249Cys-mutation-dependent bladder cancers and the overexpression of this mutated receptor. (Qing et al., 2009; Lamont et al., 2011). This line has therefore been used for evaluating the ability of the FGF-R antagonists of the present invention to counteract the pro-tumour effects of the Ser249Cys mutation of FGF receptor 3.

Thus a subject of the present invention is the therapeutic use of the compound, which is an imidazopyridine derivative, corresponding to formula (I):

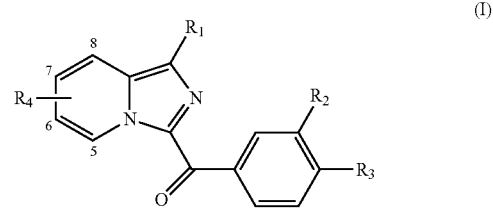

in which:
R$_1$ represents
  a hydrogen or halogen atom,
  an alkyl group optionally substituted with —COOR$_5$,
  an alkenyl group optionally substituted with —COOR$_5$,
  a —COOR$_5$ or —CONR$_5$R$_6$ group,
  an —NR$_5$COR$_6$ or —NR$_5$—SO$_2$R$_6$ group,
or
  an aryl, in particular phenyl, group or a heteroaryl group, said aryl or heteroaryl group being optionally substituted with one or more groups chosen from halogen or oxygen atoms, alkyl groups, cycloalkyl groups, —COOR$_5$, —CF$_3$, —OCF$_3$, —CN, —C(NH$_2$)NOH, —OR$_5$, —O-Alk-COOR$_5$, —O-Alk-NR$_5$R$_6$, —O-Alk-NR$_7$R$_8$, -Alk-OR$_5$, -Alk-COOR$_5$, —CONR$_5$R$_6$, —CONR$_5$-Alk-Phenyl, —CO—NR$_5$—OR$_6$, —CO—NR$_5$—SO$_2$R$_7$, —CONR$_5$-Alk-NR$_5$R$_6$, —CONR$_5$-Alk-NR$_7$R$_8$, -Alk-NR$_5$R$_6$, —NR$_5$R$_6$, —NC(O)N(CH$_3$)$_2$, —CO-Alk, —CO(OAlk)$_n$OH, —COO-Alk-NR$_5$R$_6$, —COO-Alk-NR$_7$R$_8$ and 5-membered heteroaryl groups, said heteroaryl groups being optionally substituted with one or more groups chosen from halogen atoms and alkyl, —CF$_3$, —CN, —COOR$_5$, -Alk-OR$_5$, -Alk-COOR$_5$, —CONR$_5$R$_6$, —CONR$_7$R$_8$, —CO—NR$_5$—OR$_6$, —CO—NR$_5$—SO$_2$R$_6$, —NR$_5$R$_6$ and -Alk-NR$_5$R$_6$ groups, or with a hydroxyl group or with an oxygen atom, n is an integer ranging from 1 to 3, R$_2$ and R$_3$ together form, with the carbon atoms of the phenyl nucleus to which they are attached, a 6-membered nitrogenous heterocycle corresponding to one of the formulae (A), (B) and (C) below:

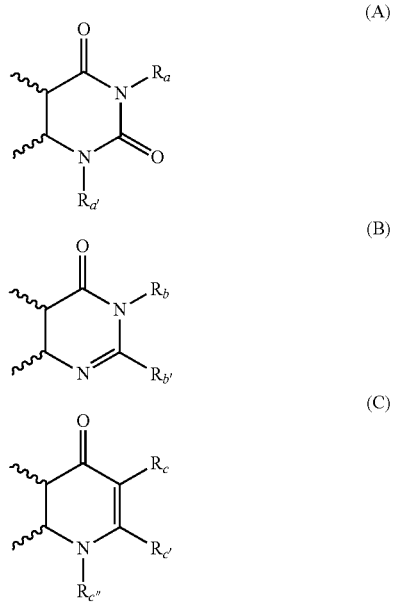

in which the wavy lines represent the phenyl nucleus to which R$_2$ and R$_3$ are attached and:

R$_a$ represents a hydrogen atom or an alkyl, haloalkyl, -Alk-CF$_3$, -Alk-COOR$_5$, -Alk'-COOR$_5$, -Alk-CONR$_5$R$_6$, -Alk'-CONR$_5$R$_6$, -Alk-CONR$_7$R$_8$, -Alk-NR$_5$R$_6$, -AlkCONR$_5$—OR$_6$, -Alk-NR$_7$R$_8$, -Alk-cycloalkyl, -Alk-O—R$_5$, -Alk-S—R$_5$, -Alk-CN, —OR$_5$, —OAlkCOOR$_5$, —NR$_5$R$_6$, —NR$_5$—COOR$_6$, -Alk-aryl, -Alk'-aryl, -Alk-O-aryl, -Alk-O-heteroaryl, -Alk-heteroaryl or heteroaryl group, where the aryl or heteroaryl group is optionally substituted with one or more halogen atoms and/or alkyl, cycloalkyl, —CF$_3$, —OCF$_3$, —O—R$_5$, —S—R$_5$, or —O-Alk-NR$_7$R$_8$ groups, R$_{a'}$ represents a hydrogen atom or a linear, branched, cyclic or partially cyclic alkyl group or an -Alk-OR$_5$, -Alk-NR$_5$R$_6$ or -Alk-NR$_7$R$_8$ group, R$_{a'}$ being optionally substituted with one or more halogen atoms, R$_b$ represents a hydrogen atom or an alkyl or -Alk-COOR$_5$ group, R$_{b'}$ represents a hydrogen atom or an alkyl, haloalkyl, cycloalkyl, phenyl or -Alk-COOR$_5$ group, R$_c$ represents a hydrogen atom or an alkyl, —CN, —COOR$_5$, —CO—NR$_5$R$_6$, —CONR$_7$R$_8$, —CO—NR$_5$-Alk-NR$_5$R$_6$, —CONR$_5$-Alk-OR$_5$, —CONR$_5$SO$_2$R$_5$, -Alk-aryl or -Alk-heteroaryl group, where the aryl or heteroaryl group is optionally substituted with one or more halogen atoms and/or alkyl, cycloalkyl, —CF$_3$, —OCF$_3$, —O-alkyl or —S-alkyl groups, R$_{c'}$ represents a hydrogen atom or an alkyl group, R$_{c''}$ represents a hydrogen atom or an alkyl, alkenyl, haloalkyl, cycloalkyl, -Alk-NR$_5$R$_6$, -Alk-NR$_7$R$_8$, -Alk-OR$_5$ or -Alk-SR$_5$ group, R$_4$, located on position 6, 7 or 8 of the imidazopyridine nucleus, represents:
a hydrogen atom,
a —COOR$_5$ group,
a —CO—NR$_5$-Alk-NR$_5$R$_6$ group,
a —CO—NR$_5$-Alk-NR$_7$R$_8$ group, or
a —CO—NR$_5$-Alk-OR$_6$ group, R$_5$ and R$_6$, which may be identical or different, represent hydrogen atoms, haloalkyl groups or alkyl groups, cycloalkyl groups, or an Ms (mesyl) group, R$_7$ and R$_8$, which may be identical or different, represent hydrogen atoms or alkyl or phenyl groups, or else R$_7$ and R$_8$ together form a saturated 3- to 8-membered ring optionally comprising a heteroatom, Alk represents a linear or branched alkylene chain, and Alk' represents a linear, branched, cyclic or partially cyclic alkylene chain, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

The compounds of formula (I) can comprise one or more asymmetric carbon atoms. They can therefore exist in the form of enantiomers or diastereoisomers. These enantiomers, diastereoisomers and also mixtures thereof, including racemic mixtures, are part of the invention.

These compounds of formula (I) can exist in the form of bases or of acids or can be salified with acids or bases, in particular pharmaceutically acceptable acids or bases. Advantageously, the compounds of formula (I) can exist in the form of a sodium salt or of a hydrochloride salt. Such addition salts are part of the invention. These salts are advantageously prepared with pharmaceutically acceptable acids or bases, but the salts of other acids or bases which are of use, for example, for purifying or isolating the compounds of formula (I) are also part of the invention.

In the context of the present invention, and unless otherwise mentioned in the text:
the term alkyl is intended to mean: a linear or branched, saturated hydrocarbon-based aliphatic group comprising from 1 to 6 carbon atoms, particularly from 1 to 4 carbon atoms. By way of examples, mention may be made of methyl ethyl, propyl and butyl groups;
the term alkenyl is intended to mean: a linear or branched, monounsaturated or polyunsaturated aliphatic group comprising, for example, one or two ethylenic unsaturations and comprising from 1 to 6 carbon atoms;
the term cycloalkyl is intended to mean: a 3- to 8-membered cyclic alkyl group comprising between 3 and 6 carbon atoms and optionally comprising one or more heteroatoms, for example 1 or 2 heteroatoms, such as nitrogen and/or oxygen, said cycloalkyl group being optionally substituted with one or more halogen atoms and/or alkyl groups. By way of examples, mention may be made of cyclopropyl, cyclopentyl, piperazinyl, morpholinyl, pyrrolidinyl and piperidinyl groups;

the term partially cyclic alkyl group is intended to mean: an alkyl group of which only one part forms a ring;

the term alkylene is intended to mean: a linear or branched, divalent alkyl group comprising from 1 to 6 carbon atoms, more particularly from 1 to 4 carbon atoms;

the term halogen is intended to mean: a chlorine, fluorine, bromine or iodine atom, advantageously fluorine or chlorine;

the term haloalkyl is intended to mean: an alkyl chain in which all or some of the hydrogen atoms are replaced with halogen atoms, such as fluorine atoms;

the term aryl is intended to mean: a cyclic aromatic group comprising between 5 and 10 carbon atoms, for example a phenyl group;

the term heteroaryl is intended to mean: a cyclic aromatic group comprising between 3 and 10 atoms, including 1 or more heteroatoms, for example between 1 and 4 heteroatoms, such as nitrogen, oxygen or sulphur, this group comprising one or more, preferably 1 or 2, rings. The heteroryls may comprise several condensed rings. The heteroaryls are optionally substituted with one or more alkyl groups or an oxygen atom. By way of examples, mention may be made, as 1-ring heteroaryls, of thienyl, pyridinyl, pyridinonyl, pyrazolyl, imidazolyl, thiazolyl and triazolyl groups; and as 2-ring heteroaryls, of indolyl, indolinyl, quinolinyl, imidazopyridinyl, benzofuranyl and benzodixolyl groups;

the term 5-membered heteroaryl is intended to mean: a heteroaryl group consisting of a 5-membered ring comprising 1 to 4 heteroatoms (such as oxygen and/or nitrogen or sulphur atoms), optionally substituted with one or more alkyl groups or a hydroxyl group or with an oxygen atom. Mention may be made, for example, of oxadiazolyl, imidazolyl, pyrazolyl, thiazolyl, thiophenyl and tetrazolyl groups.

In the present application, the terms "use of the compounds of formula (I) or a pharmaceutically acceptable salt thereof in the preparation of a medicament for the treatment of" can be understood to be synonymous with "compound of formula (I) or a pharmaceutically acceptable salt thereof for use in the treatment of".

A first subgroup which is a subject of the invention is the therapeutic use of the compound, which is an imidazopyridine derivative, corresponding to formula (I):

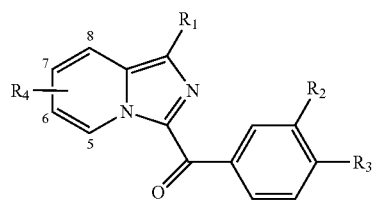

in which:
R$_1$ represents
a hydrogen or halogen atom,
an alkyl group optionally substituted with —COOR$_5$,
an alkenyl group optionally substituted with —COOR$_5$,
a group —COOR$_5$, —CONR$_5$R$_6$,
a group —NR$_5$COR$_6$, —NR$_5$—SO$_2$R$_6$,
or
an aryl, in particular phenyl, group or a heteroaryl group, said aryl or heteroaryl group being optionally substituted with one or more groups chosen from halogen atoms, alkyl groups, cycloalkyl groups, —COOR$_5$, —CF$_3$, —OCF$_3$, —CN, —C(NH$_2$)NOH, —OR$_5$, —O-Alk-COOR$_5$, —O-Alk-NR$_5$R$_6$, —O-Alk-NR$_7$R$_8$, -Alk-OR$_5$, -Alk-COOR$_5$, —CONR$_5$R$_6$, —CO—NR$_5$—OR$_6$, —CO—NR$_5$—SO$_2$R$_7$, —CONR$_5$-Alk-NR$_5$R$_6$, —CONR$_5$-Alk-NR$_7$R$_8$, -Alk-NR$_5$R$_6$, —NR$_5$R$_6$, —NC(O)N(CH$_3$)$_2$, —CO-Alk, —CO(OAlk)$_n$OH, —COO-Alk-NR$_5$R$_6$, —COO-Alk-NR$_7$R$_8$ and 5-membered heteroaryl groups, said heteroaryl groups being optionally substituted with one or more groups chosen from halogen atoms and alkyl, —CF$_3$, —CN, —COOR$_5$, -Alk-OR$_5$, -Alk-COOR$_5$, —CONR$_5$R$_6$, —CONR$_7$R$_8$, —CO—NR$_5$—OR$_6$, —CO—NR$_5$—SO$_2$R$_6$, —NR$_5$R$_6$ and -Alk-NR$_5$R$_6$ groups, or with a hydroxyl group or with an oxygen atom, n is an integer ranging from 1 to 3, R$_2$ and R$_3$ together form, with the carbon atoms of the phenyl nucleus to which they are attached, a 6-membered nitrogenous heterocycle corresponding to one of the formulae (A), (B) and (C) below:

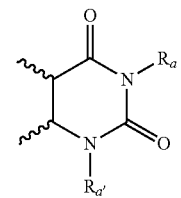

(A)

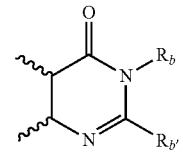

(B)

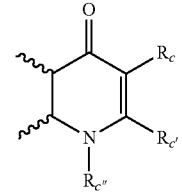

(C)

in which the wavy lines represent the phenyl nucleus to which R$_2$ and R$_3$ are attached and:

R$_a$ represents a hydrogen atom or an alkyl, haloalkyl, -Alk-CF$_3$, -Alk-COOR$_5$, -Alk'-COOR$_5$, -Alk-CONR$_5$R$_6$, -Alk'-CONR$_5$R$_6$, -Alk-CONR$_7$R$_8$, -Alk-NR$_5$R$_6$, -AlkCONR$_5$—OR$_6$, -Alk-NR$_7$R$_8$, -Alk-cycloalkyl, -Alk-O—R$_5$, -Alk-S—R$_5$, -Alk-CN, —OR$_5$, —OAlkCOOR$_5$, —NR$_5$R$_6$, —NR$_5$—COOR$_6$, -Alk-aryl, -Alk-O-aryl, -Alk-O-heteroaryl, -Alk-heteroaryl or heteroaryl group, where the aryl or heteroaryl group is optionally substituted with one or more halogen atoms and/or alkyl, cycloalkyl, —CF$_3$, —OCF$_3$, —O—R$_5$ or —S—R$_5$ groups, R<sub>a'</sub> represents a hydrogen atom or a linear, branched, cyclic or partially cyclic alkyl group or an -Alk-OR$_5$, -Alk-NR$_5$R$_6$ or -Alk-NR$_7$R$_8$ group, R$_{a'}$ being optionally substituted with one or more halogen atoms, R$_b$ represents a hydrogen atom or an alkyl or -Alk-COOR$_5$ group, R$_{b'}$ represents a hydrogen atom or an alkyl, haloalkyl, cycloalkyl, phenyl or -Alk-COOR$_5$ group, R$_c$ represents a hydrogen atom or an alkyl, —CN, —COOR$_5$, —CO—NR$_5$R$_6$, —CONR$_7$R$_8$ —CO—NR$_5$-Alk-NR$_5$R$_6$, —CONR$_5$-Alk-OR$_5$, —CONR$_5$SO$_2$R$_5$, -Alk-aryl or -Alk-heteroaryl group, where the aryl or heteroaryl group is optionally substituted with one or more halogen atoms and/or alkyl, cycloalkyl, —CF$_3$, —COF$_3$, —O-alkyl or —S-alkyl groups, R$_{c'}$ represents a hydrogen atom or an alkyl group, R$_{c''}$ represents a hydrogen atom or an alkyl, alkenyl, haloalkyl, cycloalkyl, -Alk-NR$_5$R$_6$, -Alk-NR$_7$R$_8$, -Alk-OR$_5$ or -Alk-SR$_5$ group, R$_4$, located on position 6, 7 or 8 of the imidazopyridine nucleus, represents:
a hydrogen atom,
a —COOR$_5$ group,
a —CO—NR$_5$-Alk-NR$_5$R$_6$ group,
a —CO—NR$_5$-Alk-NR$_7$R$_8$ group, or
a —CO—NR$_5$-Alk-OR$_6$ group, R$_5$ and R$_6$, which may be identical or different, represent hydrogen atoms, haloalkyl groups or alkyl groups, cycloalkyl groups, or an Ms (mesyl) group, R$_7$ and R$_8$, which may be identical or different, represent hydrogen atoms or alkyl or phenyl groups, or else R$_7$ and R$_8$ together form a saturated 3- to 8-membered ring optionally comprising a heteroatom, Alk represents a linear or branched alkylene chain, and Alk' represents a linear, branched, cyclic or partially cyclic alkylene chain, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A second subgroup which is a subject of the invention is the therapeutic use of the compound, which is an imidazopyridine derivative, corresponding to formula (I):

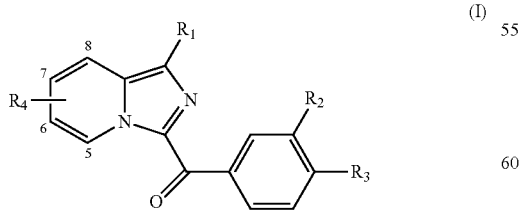

(I)

in which:
R$_1$ represents
a hydrogen atom,
an alkyl group optionally substituted with —COOR$_5$,
an alkenyl group optionally substituted with —COOR$_5$,
a —CONR$_5$R$_6$ group,
an —NR$_5$—SO$_2$R$_6$ group,
or
or an aryl, in particular phenyl, group or a heteroaryl group, said aryl or heteroaryl group of being optionally substituted with one or more groups chosen from halogen or oxygen atoms, alkyl groups, cycloalkyl groups, —COOR$_5$, —CF$_3$, —OCF$_3$, —CN, —C(NH$_2$)NOH, —OR$_5$, —O-Alk-COOR$_5$, —O-Alk-NR$_5$R$_6$, —O-Alk-NR$_7$R$_8$, -Alk-OR$_5$, -Alk-COOR$_5$, —CONR$_5$R$_6$, —CONR$_5$-Alk-Phenyl, —CO—NR$_5$—OR$_6$, —CO—NR$_5$—SO$_2$R$_7$, —CONR$_5$-Alk-NR$_5$R$_6$, —CONR$_5$-Alk-NR$_7$R$_8$, —NR$_5$R$_6$, —NC(O)N(CH$_3$)$_2$, —CO-Alk, —CO(OAlk)$_n$OH, —COO-Alk-NR$_5$R$_6$, —COO-Alk-NR$_7$R$_8$ and 5-membered heteroaryl groups, said heteroaryl groups being optionally substituted with one or more groups chosen from alkyl groups, or with a hydroxyl group, n is an integer ranging from 1 to 3, R$_2$ and R$_3$ together form, with the carbon atoms of the phenyl nucleus to which they are attached, a 6-membered nitrogenous heterocycle corresponding to one of the formulae (A), (B) and (C) below:

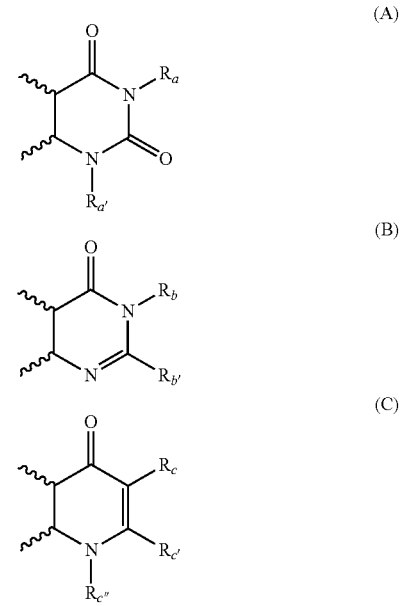

in which the wavy lines represent the phenyl nucleus to which R$_2$ and R$_3$ are attached and:

R$_a$ represents a hydrogen atom or an alkyl, -Alk-CF$_3$, -Alk-COOR$_5$, -Alk-CONR$_5$R$_6$, -Alk-cycloalkyl, Alk'-aryl, -Alk-aryl, -Alk-O-aryl or -Alk-heteroaryl group, where the aryl or heteroaryl group is optionally substituted with one or more halogen atoms and/or alkyl, cycloalkyl, —CF$_3$ or —O-Alk-NR$_7$R$_8$ groups, R$_{a'}$ represents a hydrogen atom or a linear, branched or partially cyclic alkyl group or an -Alk-OR$_5$, -Alk-NR$_5$R$_6$ or -Alk-NR$_7$R$_8$ group, R$_{a'}$ being optionally substituted with one or more halogen atoms, R$_b$ represents a hydrogen atom or an alkyl group, $R_{b'}$ represents a hydrogen atom or an alkyl, cycloalkyl, phenyl or -Alk-COOR$_5$ group, $R_c$ represents a hydrogen atom or —CO—NR$_5$R$_6$, $R_{c'}$ represents an alkyl group, $R_{c''}$ represents an alkyl group, R$_4$, located on position 6, 7 or 8 of the imidazopyridine nucleus, represents:
a hydrogen atom,
a —COOR$_5$ group,
a —CO—NR$_5$-Alk-NR$_7$R$_8$ group,
or
a —CO—NR$_5$-Alk-OR$_6$ group, R$_5$ and R$_6$, which may be identical or different, represent hydrogen atoms, haloalkyl groups or alkyl groups, or an Ms (mesyl) group, R$_7$ and R$_8$, which may be identical or different, represent hydrogen atoms or alkyl groups, or else R$_7$ and R$_8$ together form a saturated 3- to 8-membered ring which can optionally contain a heteroatom, Alk represents a linear or branched alkylene chain, and Alk' represents a cyclic alkylene chain, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A third subgroup which is a subject of the invention is the use of a compound of formula (I) in which R$_1$ represents:
a hydrogen or halogen atom,
an alkyl group which is unsubstituted or substituted with —COOR$_5$,
an alkenyl group which is unsubstituted or substituted with —COOR$_5$,
a —COOR$_5$ group,
a —CONR$_5$R$_6$ group,
an —NR$_5$—SO$_2$R$_6$ group, or
a phenyl group optionally substituted with one or two groups chosen from:
halogen atoms,
alkyl groups optionally substituted with —COOR$_5$, —CN (cyano), —C(NH$_2$)NOH, —COOR$_5$, —CONR$_5$R$_6$, —CO—NR$_5$—OR$_6$, —CO—NR$_5$—SO$_2$R$_6$, —COAlk, —CO(OAlk)$_n$OH, —OR$_5$, —OCF$_3$, —O-Alk-COOR$_5$, -Alk-OR$_5$, NR$_5$R$_6$ or —NC(O)N(CH$_3$)$_2$ groups,
5-membered heteoaryls optionally substituted with an alkyl group and/or a hydroxyl group or an oxygen atom,
in which R$_5$ and R$_6$, which may be identical or different, represent hydrogen atoms or alkyl groups optionally substituted with an —NR$_7$R$_8$ group, R$_7$ represents a hydrogen atom, an alkyl group comprising 1 or 2 carbon atoms or a phenyl group, and n is an integer ranging from 1 to 3, or
a heteroaryl group which is optionally condensed and/or optionally substituted with one or two groups chosen from alkyl groups; OR$_5$, —COOR$_5$, —NR$_5$R$_6$ and cycloalkyl groups, an oxygen atom, in which R$_5$ and R$_6$, which may be identical or different, represent hydrogen atoms or alkyl groups comprising 1 or 2 carbon atoms, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A fourth subgroup which is a subject of the invention is the use of a compound of formula (I) in which R$_2$ and R$_3$ together form, with the carbon atoms of the phenyl nucleus to which they are attached, a 6-membered nitrogenous heterocycle corresponding to one of the formulae (A) and (B) defined above, preferably corresponding to formula (A), on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A fifth subgroup which is a subject of the invention is the use of a compound of formula (I) in which formula (A) or (B) is advantageously such that:

R$_a$ represents a hydrogen atom or an alkyl group, optionally substituted with one or more halogens, -AlkCONR$_5$R$_6$, haloalkyl, —CH$_2$—COOR$_5$, -Alk-heteroaryl, -Alk-O-phenyl or -Alk-phenyl, where the phenyl group is optionally substituted with one or two alkyl and/or OR$_5$ groups and/or halogen atoms; -Alk-cycloalkyl, R$_{a'}$ represents a hydrogen atom or a linear, branched, cyclic or partially cyclic alkyl group, or a —CH$_2$—OR$_5$ or -Alk-NR$_5$R$_6$ group, R$_b$ represents a hydrogen atom or an alkyl group, R$_{b'}$ represents a hydrogen atom or an alkyl, phenyl or —CH$_2$—COOR$_5$ group, in which the alkyl groups comprise 1 to 6 carbon atoms, R$_5$ being as defined above, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A sixth subgroup which is a subject of the invention is the use of a compound of formula (I), in which R$_4$ represents a hydrogen atom or a —COOH, —CO—NH-Alk-NR$_7$R$_8$ or —CO—NH-Alk-OH group, in which Alk, R$_7$ at R$_8$ are as defined previously, or else an unsubstituted alkyl group, preferably comprising from 1 to 3 carbon atoms, on the condition that the compound of formula (I) is other than:

3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid, 1,2-dimethyl-4-oxo-6-(1-pyridin-3-ylimidazo[1,5-a]pyridine-3-carbonyl)-1,4-dihydroquinoline-3-carboxylic acid dimethylamide, or a pharmaceutically acceptable salt thereof, for preparing a medicament for the treatment of bladder cancer.

A seventh subgroup which is a subject of the invention is the use of a compound of formula (I), in which $R_4$ is advantageously located on position 6 or 7 of the imidazopyridine nucleus;
on the condition that the compound of formula (I) is other than:
3-{3-[1-(2-dimethylaminoethyl)-3-(4-fluorobenzyl)-2,4-dioxo-1,2,3,4-tetrahydroquinazoline-6-carbonyl]imidazo[1,5-a]pyridin-1-yl}benzoic acid,
1,2-dimethyl-4-oxo-6-(1-pyridin-3-ylimidazo[1,5-a]pyridine-3-carbonyl)-1,4-dihydroquinoline-3-carboxylic acid dimethylamide,
or a pharmaceutically acceptable salt thereof, for preparing a medicament for the treatment of bladder cancer.

An eighth subgroup which is a subject of the invention is the use of a compound of formula (I) in which:
$R_1$ represents
  a hydrogen or halogen atom,
  an alkyl group optionally substituted with —$COOR_5$,
  an alkenyl group optionally substituted with —$COOR_5$,
  a —$COOR_5$ or —$CONR_5R_6$ group,
  an —$NR_5COR_6$ or —$NR_5$—$SO_2R_6$ group,
  or
  an aryl, in particular phenyl, group optionally substituted with one or more groups chosen from: halogen atoms, alkyl groups, cycloalkyl groups, —$COOR_5$, —$CF_3$, —$OCF_3$, —CN, —$C(NH_2)NOH$, —$OR_5$, —O-Alk-$COOR_5$, —O-Alk-$NR_5R_6$, —O-Alk-$NR_7R_8$, -Alk-O $R_5$, -Alk-COO $R_5$, —$CONR_5R_6$, —CO—$NR_5$—$OR_6$, —CO—$NR_5$—$SO_2R_7$, —$CONR_5$-Alk-$NR_5R_6$, —$CONR_5$-Alk-$NR_7R_8$, -Alk-$NR_5R_6$, —$NR_5R_6$, —$NC(O)N(CH_3)_2$, —CO-Alk, —$CO(OAlk)_nOH$, COO-Alk-$NR_5R_6$, —COO-Alk-$NR_7R_8$ and 5-membered heteroaryl groups, said heteroaryl groups being optionally substituted with one or more groups chosen from halogen atoms and alkyl, —$CF_3$, —CN, —$COOR_5$, -Alk-$OR_5$, -Alk-$COOR_5$, —$CONR_5R_6$, —$CONR_7R_8$, —CO—$NR_5$—$OR_6$, —CO—$NR_5$—$SO_2R_6$, —$NR_5R_6$ and -Alk-$NR_5R_6$ groups, or with a hydroxyl group or with an oxygen atom,
or a pharmaceutically acceptable salt thereof, for preparing a medicament for the treatment of bladder cancer.

A ninth subgroup which is a subject of the invention is the use of a compound of formula (I) in which:
$R_2$ and $R_3$ together form, with the carbon atoms of the phenyl nucleus to which they are attached, a 6-membered nitrogenous heterocycle corresponding to one of the formulae (A) and (B) defined previously,
or a pharmaceutically acceptable salt thereof, for preparing a medicament for the treatment of bladder cancer.

A tenth subgroup which is a subject of the invention is the use of a compound of formula (I) in which:
$R_{a'}$ represents a hydrogen atom or a linear, branched, cyclic or partially cyclic alkyl group or an -Alk-$OR_5$ or -Alk-$NR_7R_8$ group, Ra' being optionally substituted with one or more halogen atoms,
or a pharmaceutically acceptable salt thereof, for preparing a medicament for the treatment of bladder cancer.

The first, second, third, fourth, fifth, seventh, eighth, ninth and tenth subgroups defined above, taken separately or in combination, are also part of the invention.

An eleventh subgroup which is a subject of the invention is the use of one of the following components:
3-[3-(2,4-dioxo-3-propyl-1,2,3,4-tetrahydroquinazoline-6-carbonyl)imidazo[1,5-a]pyridin-1-yl]benzamide
3-{3-[3-(4-fluorobenzyl)-1-methyl-2,4-dioxo-1,2,3,4-tetrahydroquinazoline-6-carbonyl]imidazo[1,5-a]pyridin-1-yl}benzoic acid
3-[3-(2-methyl-4-oxo-3-propyl-3,4-dihydroquinazoline-6-carbonyl)imidazo[1,5-a]pyridin-1-yl]benzamide
3-{3-[3-(4-fluorobenzyl)-1-methoxymethyl-2,4-dioxo-1,2,3,4-tetrahydroquinazoline-6-carbonyl]imidazo[1,5-a]pyridin-1-yl}benzoic acid
3-{3-[3-(4-fluorobenzyl)-1-methyl-2,4-dioxo-1,2,3,4-tetrahydroquinazoline-6-carbonyl]imidazo[1,5-a]pyridin-1-yl}benzoic acid ethyl ester
3-{3-[3-(3-fluorobenzyl)-1-methyl-2,4-dioxo-1,2,3,4-tetrahydroquinazoline-6-carbonyl]imidazo[1,5-a]pyridin-1-yl}benzamide
3-(4-fluorobenzyl)-1-methyl-6-(1-pyridin-3-ylimidazo[1,5-a]pyridine-3-carbonyl)-1H-quinazoline-2,4-dione
N-(2-dimethylaminoethyl)-3-{3-[3-(4-fluorobenzyl)-1-methyl-2,4-dioxo-1,2,3,4-tetrahydroquinazoline-6-carbonyl]imidazo[1,5-a]pyridin-1-yl}benzamide
3-(4-fluorobenzyl)-1-methyl-6-{1-[3-(5-methyl-[1,3,4]oxadiazol-2-yl)phenyl]imidazo[1,5-a]pyridine-3-carbonyl}-1H-quinazoline-2,4-dione
3-(3-{3-[2-(4-fluorophenyl)ethyl]-1-methyl-2,4-dioxo-1,2,3,4-tetrahydroquinazoline-6-carbonyl}imidazo[1,5-a]pyridin-1-yl)benzoic acid
3-{3-[3-(4-methylpentyl)-2,4-dioxo-1-propyl-1,2,3,4-tetrahydroquinazoline-6-carbonyl]imidazo[1,5-a]pyridin-1-yl}benzoic acid
1-methyl-3-(5-methylthiophen-2-ylmethyl)-6-(1-pyridin-3-ylimidazo[1,5-a]pyridine-3-carbonyl)-1H-quinazoline-2,4-dione
3-(3-{3-[2-(4-fluorophenoxy)ethyl]-1-methyl-2,4-dioxo-1,2,3,4-tetrahydroquinazoline-6-carbonyl}imidazo[1,5-a]pyridin-1-yl)benzoic acid
3-(3-{3-[2-(4-fluorophenoxy)ethyl]-2,4-dioxo-1-propyl-1,2,3,4-tetrahydroquinazoline-6-carbonyl}imidazo[1,5-a]pyridin-1-yl)benzoic acid
3-{3-[3-(5-methylthiophen-2-ylmethyl)-2,4-dioxo-1-propyl-1,2,3,4-tetrahydroquinazoline-6-carbonyl]imidazo[1,5-a]pyridin-1-yl}benzoic acid
3-(4-fluorobenzyl)-6-(imidazo[1,5-a]pyridine-3-carbonyl)-1-methyl-1H-quinazoline-2,4-dione
6-[1-(2-dimethylaminopyrimidin-5-yl)imidazo[1,5-a]pyridine-3-carbonyl]-3-(4-fluorobenzyl)-1-propyl-1H-quinazoline-2,4-dione
3-(4-fluorobenzyl)-6-[1-(6-oxo-1,6-dihydropyridin-3-yl)imidazo[1,5-a]pyridine-3-carbonyl]-1-propyl-1H-quinazoline-2,4-dione,
or a pharmaceutically acceptable salt thereof, for preparing a medicament for the treatment of bladder cancer.

In what follows, the term "protective group" is intended to mean a group which makes it possible, firstly, to protect a reactive function such as a hydroxyl or an amine during a synthesis and, secondly, to regenerate the intact reactive function at the end of synthesis. Examples of protective groups and also methods of protection and of deprotection are given in <<Protective Groups in organic Synthesis>>, Green et al., 4th Edition (John Wiley & Sons, Inc., New York).

In what follows, the term "leaving group" is intended to mean a group which can be easily cleaved from a molecule by breaking a heterolytic bond, with the departure of a pair of electrons. This group can thus be easily replaced with another group in a substitution reaction, for example. Such leaving groups are, for example, halogens or an activated hydroxyl group, such as a mesyl, tosyl, triflate, acetyl, para-nitrophenyl, etc. Examples of leaving groups and also methods for preparing them are given in <<Advances in organic Chemistry>>, J. March, 5th Edition, Wiley Interscience, p. 310-316.

The compounds of general formula (I) can be prepared according to the processes hereinafter.

The compounds of formula (IV) are obtained by methods known in the literature, from the corresponding suitably substituted 2-aminomethylpyridines, according to the following reaction scheme, described in *J. Chem. Soc.* (1955), 2834-2836.

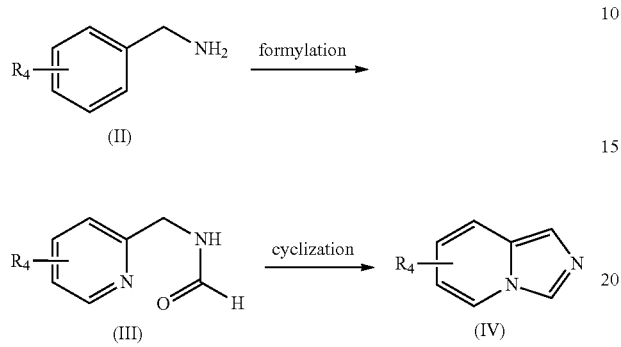

When $R_4$ represents —$COOR_5$, the compounds of formula (II) are obtained according to the reaction scheme described in WO06/097625.

Scheme 1 presents a pathway for obtaining the compounds of formula (I) in which $R_2$ and $R_3$ together form a nitrogenous heterocycle of formula (A) as defined previously, and in which $R_1$ and $R_{a'}$ represent hydrogen atoms.

Scheme 1 (Method 1):

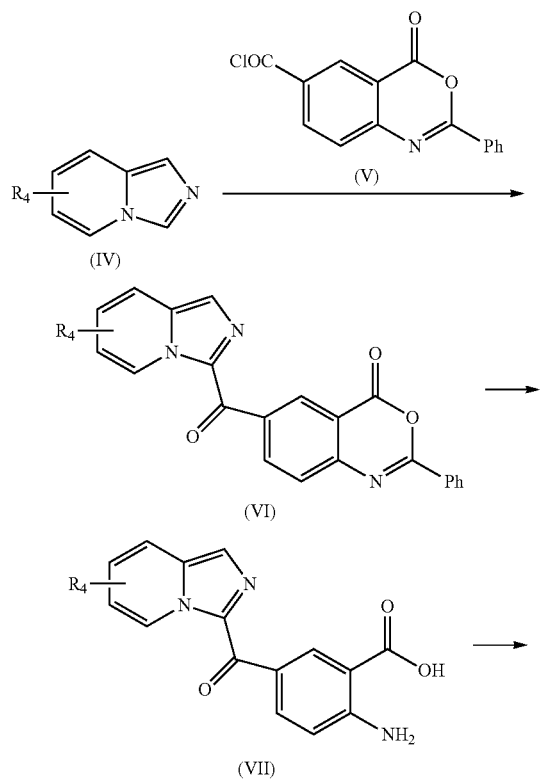

The compound of formula (IV), in which $R_4$ is as defined for the compound of formula (I), is condensed with the compound of formula (V) in order to obtain the compound of formula (VI). The compound of formula (VI) is subjected to a basic hydrolysis reaction in order to obtain the compound of formula (VII). The esterification of the compound of formula VII results in the compound of formula (VIII). Through the action of triphosgene, the isocyanate corresponding to the compound of formula (VIII) is formed, and is condensed with an amine of formula $R_aNH_2$ in order to obtain the urea of formula (IX). The compound of formula (IX) is subjected to a cyclization reaction in a basic medium in order to obtain the compound of formula I in which $R_4$ and $R_a$ are as defined previously.

Scheme 2 presents a pathway for obtaining the compounds of formula (I) in which $R_2$ and $R_3$ together form a nitrogenous heterocycle of formula (A) as defined previously, and in which $R_1$ represents a group as defined in the general formula, except for a hydrogen atom.

Scheme 2 (Method 2):

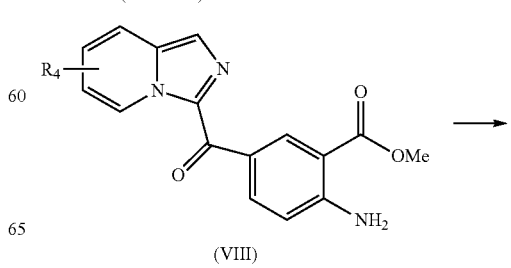

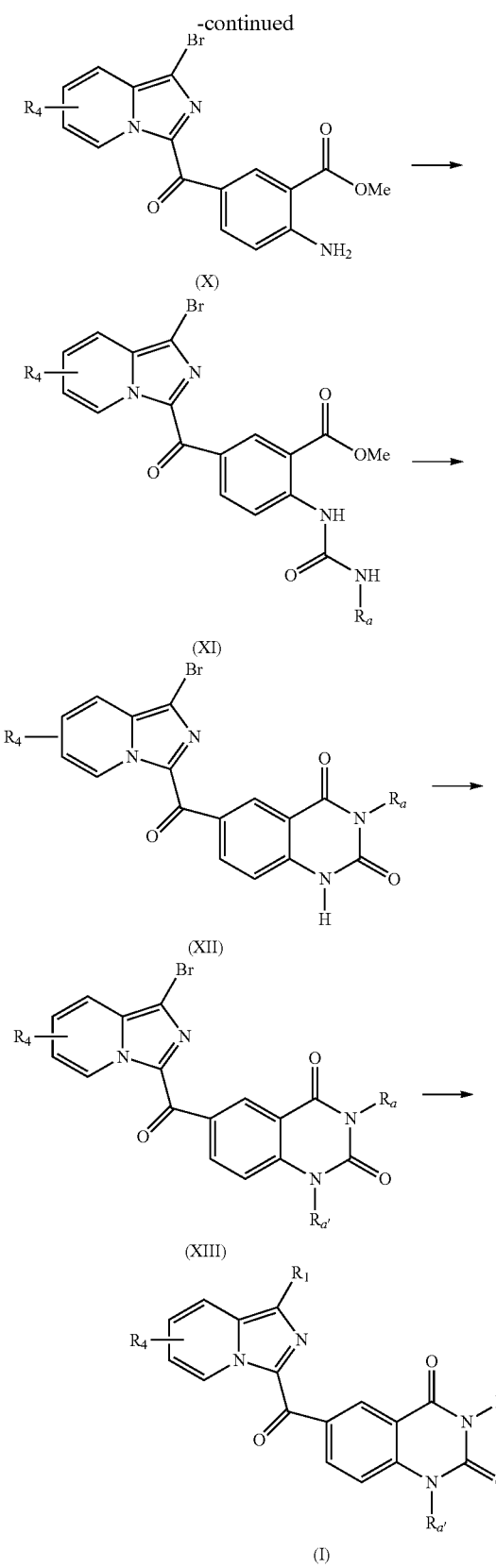

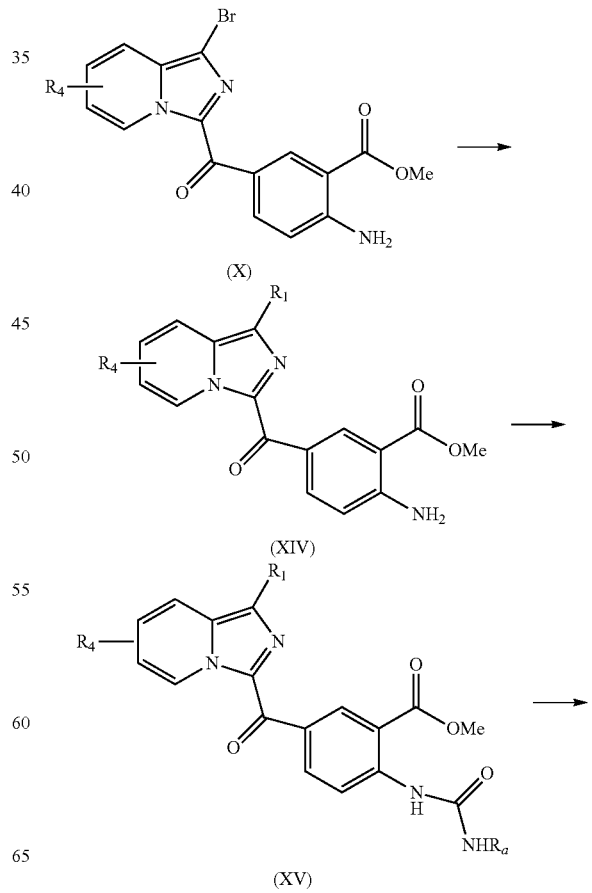

nate corresponding to the compound of formula (X) is formed, and is condensed with an amine of formula $R_aNH_2$ in order to obtain the urea of formula (XI). The compound of formula (XI) is subjected to a cyclization reaction in a basic medium in order to obtain the compound of formula (XII). The compound (XII) is subjected to an alkylation reaction in the presence of a base and of a halogenated derivative Ra'X in order to obtain the compound of formula (XIII). The compound of formula (XIII) is subjected, in the presence of a palladium catalyst, of a ligand and of a base, to a reaction with phenylboronic or heteroarylboronic derivatives or phenylboronate esters or heteroarylboronate esters according to a Suzuki coupling, or alternatively to an imination reaction with benzophenone imine, followed by acid hydrolysis and an alkylation reaction with a sulphonyl chloride of formula $R_6SO_2Cl$, or alternatively to a cyanation reaction with zinc cyanide, followed by acid hydrolysis and esterification or peptide coupling with an amine $R_5R_6NH_2$, in order to obtain the compound of formula (I) in which $R_1$, $R_4$, $R_a$ et $R_{a'}$ are as defined previously.

Scheme 3 presents a pathway for obtaining the compounds of formula (I) in which $R_2$ and $R_3$ together form a nitrogenous heterocycle of formula (A) as defined previously, and in which $R_1$ represents a group as defined in the general formula, except for a hydrogen atom, and in which $R_4$ is as defined previously.

Scheme 3 (Method 3):

The compound of formula (VIII) is subjected to a bromination reaction in order to obtain the compound of formula (X). Through the action of triphosgene, the isocya- -continued

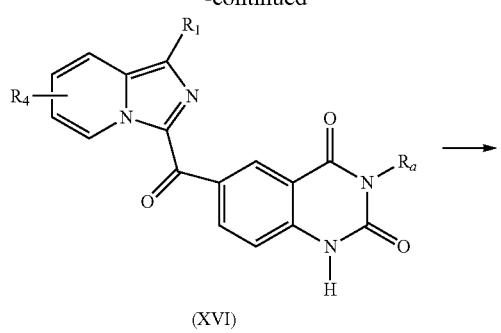

(XVI)

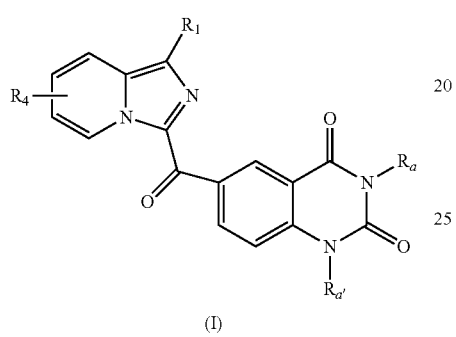

(I)

Scheme 4 (Method 4):

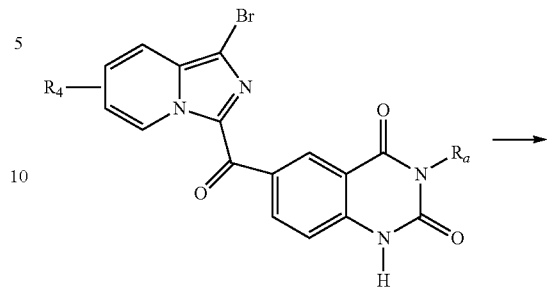

(XII)

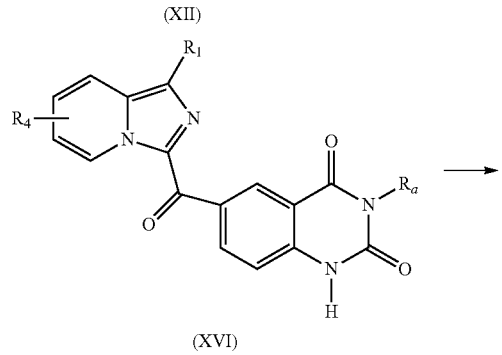

(XVI)

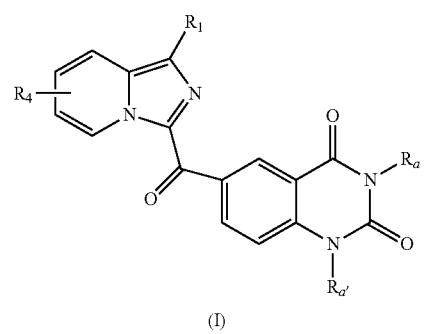

(I)

The compound of formula (X) is subjected, in the presence of a palladium catalyst, of a ligand and of a base,

- to a reaction with phenylboronic or heteroarylboronic derivatives or phenylboronate esters or heteroarylboronate esters according to a Suzuki coupling,
- or alternatively to an imination reaction with benzophenone imine, followed by acid hydrolysis and an alkylation reaction with a sulphonyl chloride of formula $R_6SO_2Cl$,
- or alternatively to a cyanation reaction with zinc cyanide, followed by acid hydrolysis and esterification or peptide coupling with an amine $R_5R_6NH_2$, $R_5$ et $R_6$ being defined above, in order to obtain the compound of formula (XIV) in which $R_1$ is as defined previously. Through the action of triphosgene, the isocyanate corresponding to the compound of formula (XIV) is formed, and is condensed with an amine of formula $R_a NH_2$ in order to obtain the urea of formula (XV).

The compound of formula (XV) is subjected to a cyclization reaction in a basic medium in order to obtain the compound of formula (XVI). The compound (XVI) is subjected to an alkylation reaction in the presence of a base and of a halogenated derivative $R_aX$ in order to obtain the compound of formula (I).

Scheme 4 presents a pathway for obtaining the compounds of formula (I) in which $R_2$ and $R_3$ together form a nitrogenous heterocycle of formula (A) as defined previously, and in which $R_1$ represents a group as defined in the general formula, except for a hydrogen atom, and in which $R_4$ is as defined previously.

The compound of formula (XII) is subjected, in the presence of a palladium catalyst, of a ligand and of a base,

- to a reaction with phenylboronic or heteroarylboronic derivatives or phenylboronate esters or heteroarylboronate esters according to a Suzuki coupling,
- or alternatively to an imination reaction with benzophenone imine, followed by acid hydrolysis and a sulphonylation reaction with a sulphonyl chloride of formula $R_6SO_2Cl$,
- or alternatively to a cyanation reaction with zinc cyanide, followed by acid hydrolysis and esterification or peptide coupling with an amine $R_5R_6NH_2$, in order to obtain the compound of formula (XVI) in which $R_1$ is as defined previously.

The compound (XVI) is subjected to an alkylation reaction in the presence of a base and of a halogenated derivative $R_aX$ in order to obtain the compound of formula (I).

Scheme 5 presents a pathway for obtaining the compounds of formula (I) in which $R_2$ and $R_3$ together form a nitrogenous heterocycle of formula (B) as defined previously, and in which $R_1$ represents a hydrogen atom and in which $R_4$ is as defined previously.

Scheme 5 (Method 5):

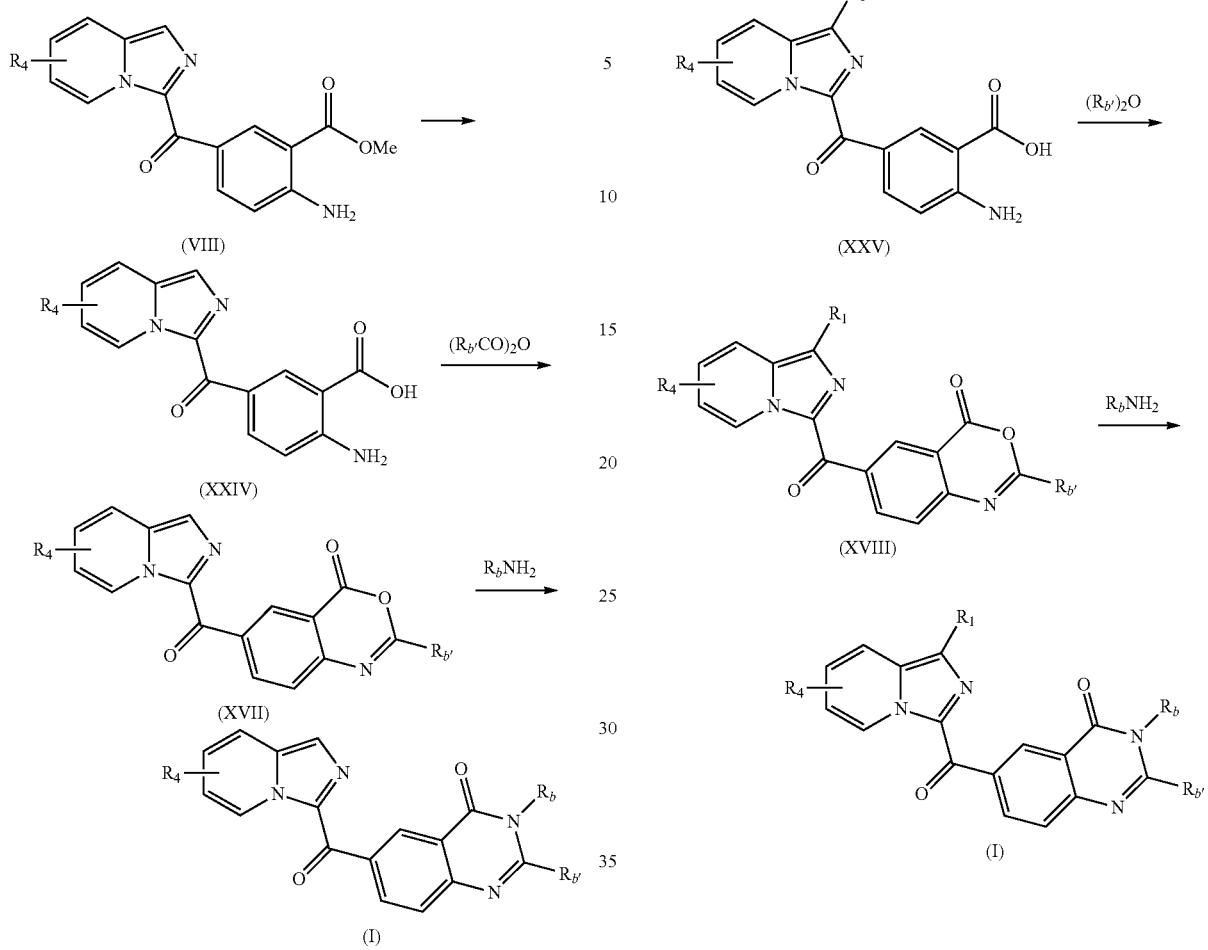

The compound (VIII) is subjected to a saponification reaction in order to obtain the compound (XXIV). The compound (XXIV) is subjected to a condensation reaction with an alkyl or aryl anhydride $(R_bCO)_2O$ in order to obtain the compound of formula (XVII). The compound of formula (XVII) is subjected to a condensation reaction with an amine $R_bNH_2$ in order to obtain a compound of formula (I) in which $R_b$ and $R_{b'}$ are defined as previously.

Scheme 6 presents a pathway for obtaining the compounds of formula (I) in which $R_2$ and $R_3$ together form a nitrogenous heterocycle of formula (B) as defined previously and in which $R_1$ is as defined previously, except for a hydrogen, and in which $R_4$ is as defined previously.

The compound (XIV) is subjected to a saponification reaction in order to obtain the compound (XXV). The compound (XXV) is then subjected to a condensation reaction with an alkyl or aryl anhydride $(R_bCO)_2O$ in order to obtain the compound of formula (XVIII). The compound of formula (XVIII) is subjected to a condensation reaction with an amine $R_bNH_2$ in order to obtain a compound of formula I in which $R_b$ and $R_{b'}$ are defined as previously.

Scheme 7 presents a pathway for obtaining the compounds of formula (I) in which $R_2$ and $R_3$ together form a nitrogenous heterocycle of formula (C) as defined previously, and in which $R_{c''}$ and also $R_1$ and $R_4$ are as defined previously.

Scheme 6 (Method 6):

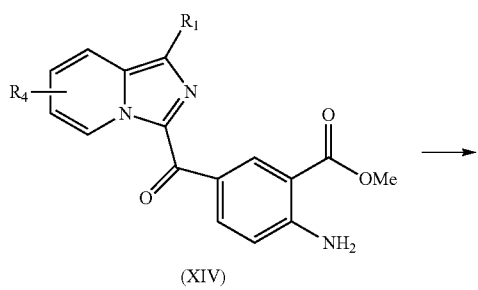

Scheme 7 (Method 7):

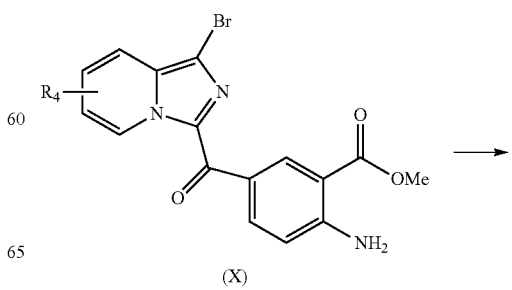

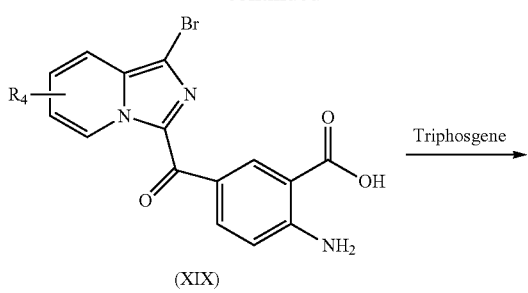

(XIX)

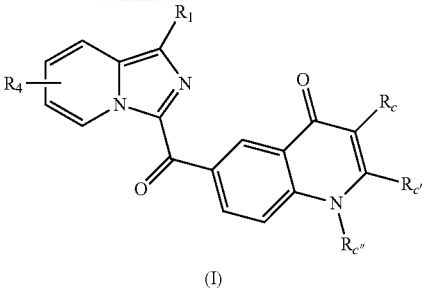

(I)

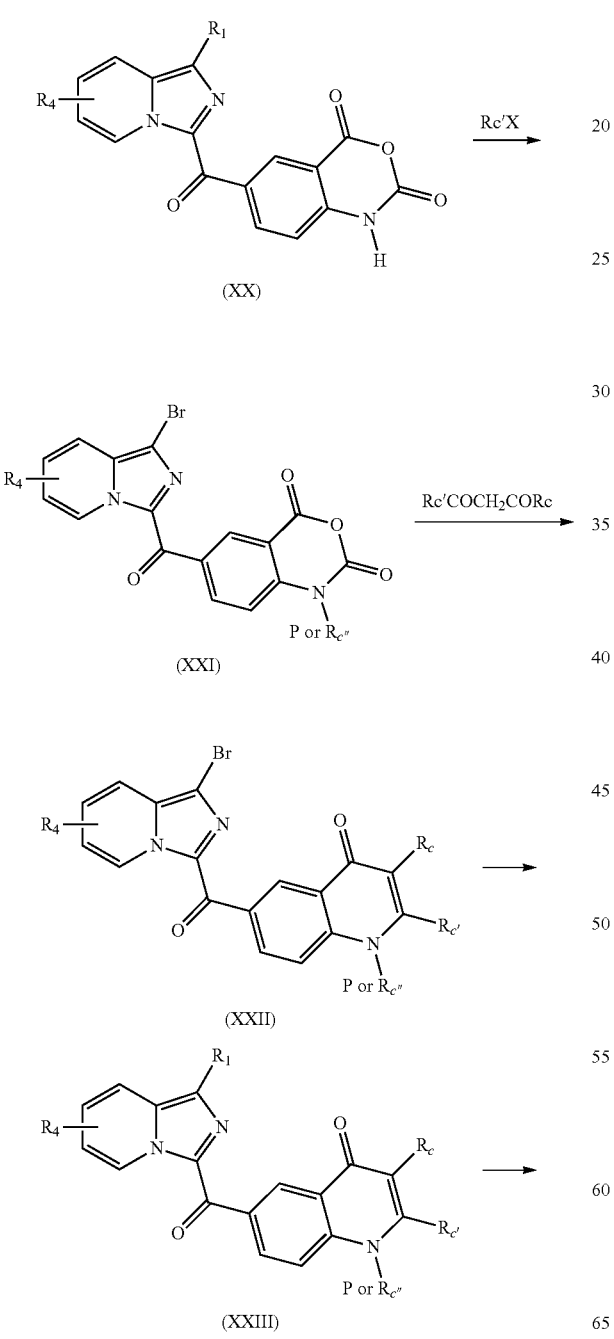

The compound (X) is subjected to a saponification reaction in order to obtain the compound (XIX). The compound (XIX) is subjected to a condensation reaction in the presence of triphosgene in order to obtain the compound (XX). The compound (XX) is subjected to an alkylation reaction in the presence of a halogenated derivative $R_{c''}X$ or of a protective group in order to obtain the compound (XXI). The compound (XXI) is subjected to a condensation reaction with a malonic derivative in order to obtain the compound (XXII) in which $R_{c'}$ et $R_c$ are defined as previously. The compound (XXII) is subjected, in the presence of a palladium catalyst, of a ligand and of a base,

- to a reaction with phenylboronic or heteroarylboronic derivatives or phenylboronate esters or heteroarylboronate esters according to a Suzuki coupling,
- or alternatively to an imination reaction with benzophenone imine, followed by acid hydrolysis and a sulphonylation reaction with a sulphonyl chloride of formula $R_6SO_2Cl$,
- or alternatively to a cyanation reaction with zinc cyanide, followed by acid hydrolysis and esterification or peptide coupling with an amine $R_5R_6NH_2$, in order to obtain the compound of formula (XXIII) in which $R_1$ is as defined previously. The compound (XXIII) is subjected to a deprotection reaction in order to obtain the compounds of formula I in which $R_{c''}$ is a hydrogen atom.

The following examples describe the preparation of certain compounds in accordance with the use according to the invention. These examples are not limiting and merely illustrate formula (I) for the use according to the present invention. The numbers of the compounds exemplified refer to those given in the table hereinafter, which shows the chemical structures and the physical properties of some compounds.

In the schemes above, the starting compounds, the reactants and the intermediates, when their preparation is not described, are commercially available or described in the literature, or else can be prepared according to methods which are described therein or which are known to those skilled in the art. Certain intermediates which are of use for preparing the compounds of formula (I) can also serve as final products of formula (I), as will become apparent in the examples given hereinafter.

By way of example, the derivatives of formula (I) chosen from the following compounds, can be used for preparing a medicament for the treatment of bladder cancer:

6-(imidazo[1,5-a]pyridine-3-ylcarbonyl)-3-propylquinazoline-2,4(1H,3H)-dione,

3-{3-[(2,4-dioxo-3-propyl-1,2,3,4-tetrahydroquinazolin-6-yl)carbonyl]imidazo[1,5-a]pyridin-1-yl}benzoic acid, 3-[(2,4-dioxo-3-propyl-1,2,3,4-tetrahydroquinazolin-6-yl)carbonyl]imidazo[1,5-a]pyridine-6-carboxylic acid, 3-(3-{[3-(4-fluorobenzyl)-1-methyl-2,4-dioxo-1,2,3,4-tetra-hydroquinazolin-6-yl]carbonyl}imidazo[1,5-a]pyridin-1-yl)benzoic acid,
3-{3[(2,4-dioxo-3-propyl-1,2,3,4-tetrahydroquinazolin-6-yl)carbonyl]imidazo[1,5-a]pyridin-1-yl}benzamide,
6-({1-[3-(5-methyl-1,3,4 oxadiazol-2-yl)phenyl]imidazo[1,5-a]pyridin-3-yl}carbonyl-3-propylquinazoline-2,4(1H,3H)-dione,
6-({1-[3-(3-methyl-1,2,4-oxadiazol-5-yl)phenyl]imidazo[1,5-a]pyridin-3-yl}carbonyl)-3-propylquinazoline-2,4(1H,3H)-dione,
N-{3-[(2,4-dioxo-3-propyl-1,2,3,4-tetrahydroquinazolin-6-yl)carbonyl]imidazo[1,5-a]pyridin-1-yl}methanesulphonamide,
2-morpholin-4-ylethyl 3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzoate,
N-[2-(dimethylamino)ethyl]-3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzamide,
3-(3-{[3-(4-fluorobenzyl)-1-propyl-2,4-dioxo-1,2,3,4-tetra-hydroquinazolin-6-yl]carbonyl}imidazo[1,5-a]pyridin-1-yl)benzoic acid,
3-(4-fluorobenzyl)-1-methyl-6-[(1-pyridin-3-ylimidazo[1,5-a]pyridin-3-yl) carbonyl]quinazoline-2,4(1H, 3H)-dione,
3-{3-[(2-methyl-4-oxo-3-propyl-3,4-dihydroquinazolin-6-yl)carbonyl]imidazo[1,5-a]pyridin-1-yl}benzoic acid,
3-{3-[(2-methyl-4-oxo-3-propyl-3,4-dihydroquinazolin-6-yl)carbonyl]imidazo[1,5-a]pyridin-1-yl}benzamide,
6-(imidazo[1,5-a]pyridin-3-ylcarbonyl)quinazolin-4(3H)-one,
3-[3-({3-[2-(4-fluorophenoxy)ethyl]-1-propyl-2,4-dioxo-1,2,3,4-tetrahydroquinazolin-6-yl}carbonyl)imidazo[1,5-a]pyridin-1-yl]benzoic acid.

Abbreviations

TOTU: O-[(ethoxycarbonyl)cyanomethylenamino]-N,N,N',N'-tetramethyluronium tetrafluoroborate
NMP: N-Methylpyrrolidone
DME: Ethylene glycol dimethyl ether
DMF: Dimethylformamide
THF: Tetrahydrofuran
Binap: 2,2'-bis(diphenylphosphino)-1,1'-binaphthyl
The NMR analyses were carried out on Bruker Avance 250 MHz, 300 MHz and 400 MHz apparatuses.
The melting points were measured on a Buchi B-450 apparatus.
The mass spectrometry analyses were carried out on a Waters Alliance 2695 (UV: PDA996, MS: LCZ), Alliance 2695 (UV: PDA 996, MS: ZQ (simple Quad) ZQ1), Alliance 2695 (UV: PDA 996, MS: ZQ (simple Quad) ZQ2), Waters UPLC Acquity (UV: Acquity PDA, MS: SQD (simple Quad) SQW), Agilent MSD, Waters ZQ, waters SQD apparatus.

EXAMPLE 1

6-(Imidazo[1,5-a]pyridine-3-ylcarbonyl)-3-propylquinazoline-2,4(1H,3H)-dione (compound No. 1)

Methyl 2-amino-5-(imidazo[1,5-a]pyridine-3-yl carbonyl)benzoate 13.4 ml (96 mmol) of triethylamine and then, under a nitrogen atmosphere at 0° C., 13.7 g (48 mmol) of 4-oxo-2-phenyl-4H-3,1-benzoxazine-6-carbonyl chloride (described in WO 05/028476) are added to 3.5 g (30 mmol) of imidazo[1,5-a]pyridine [described in J. Chem. Soc.; (1955), 2834-2836] in 250 ml of 1,2-dichloroethane. After 4.5 hours of stirring at ambient temperature, the reaction medium is filtered. The residue obtained is washed with 1,2-dichloroethane. After drying overnight at 40° C. under reduced pressure, 3 g of a yellow solid are obtained.

The residue obtained is placed in solution in 100 ml of NMP. A solution of 8.4 g (0.15 mol) of KOH in 10 ml of water is added dropwise under a nitrogen atmosphere at ambient temperature. The reaction medium is heated at 80° C. for 6 hours and then poured, at ambient temperature, onto an aqueous 1N hydrochloric acid solution. The precipitate obtained is filtered off, rinsed with water and then dried at 40° C. under reduced pressure overnight. After silica gel column chromatography, elution being carried out with a dichloromethane/methanol/0.1% triethylamine mixture, 5.5 g of a yellow solid are obtained.

7 g (0.022 mol) of caesium carbonate, then, dropwise, 1.34 ml (0.022 mol) of methyl iodide are added, under a nitrogen atmosphere at ambient temperature, to 5.5 g (0.02 mol) of the residue obtained in 100 ml of DMF. After stirring for 24 hours at ambient temperature, the reaction medium is poured onto water. The precipitate obtained is filtered off, rinsed with water and then dried overnight at 40° C. under reduced pressure. 5.1 g of a yellow solid are obtained.
Melting point: 192° C.
MH+: 296

Methyl 5-(imidazo[1,5-a]pyridin-3-ylcarbonyl)-2-[(propylcarbamoyl)amino]benzoate 0.35 g (1.2 mmol) of triphosgene is added, at ambient temperature under a nitrogen atmosphere, to a suspension of 0.5 g (1.7 mmol) of methyl 2-amino-5-(imidazo[1,5-a]pyridine-3-yl carbonyl)benzoate in 20 ml of anhydrous dioxane. After heating for 2 hours at 100° C., 0.28 ml (3.4 mmol) of n-propylamine and then 0.71 ml (5 mmol) of triethylamine are added to the reaction medium at ambient temperature. After 18 hours of stirring at ambient temperature, $H_2O$ is added. The aqueous phase is extracted with dichloromethane. The organic phase is dried over sodium sulphate, filtered and concentrated under reduced pressure. The yellow solid obtained is purified by silica gel column chromatography, elution being carried out with a dichloromethane/methanol (98/2) mixture. 0.410 g of a yellow solid is obtained.
Melting point: 205° C.
MH+: 381

6-(Imidazo[1,5-a]pyridin-3-ylcarbonyl)-3-propylquinazoline-2,4(1H,3H)-dione 1.38 ml (1.38 mmol) of an aqueous 1N sodium hydroxide solution are added, at ambient temperature, to a suspension of 0.436 g (1.15 mmol) of methyl 5-(imidazo[1,5-a]pyridin-3-ylcarbonyl)-2-[(propylcarbamoyl)amino]benzoate in 10 ml of methanol. After heating at reflux for 2 hours, the methanol is concentrated under reduced pressure. An aqueous 1N hydrochloric acid solution is added. The precipitate obtained is filtered off, rinsed with water and then dried overnight at 40° C. under reduced pressure. 0.27 g of a yellow solid is obtained.
Melting point: 304° C.
$^1$H-NMR (D6-DMSO, 400 MHz): 0.91 (t, J=7.17 Hz, 3H), 1.63 (q, J=7.59 Hz, 2H), 3.89 (t, J=7.17 Hz, 2H), 7.25-7.37 (m, 2H), 7.39-7.43 (m, 1H), 7.82 (s, 1H), 7.97 (d, J=8.86 Hz, 1H), 8.59 (d, J=8.86 Hz, 1H), 9.18 (s, 1H), 9.74 (d, J=7.17 Hz, 1H), 11.8 (s, 1H)

EXAMPLE 2

Sodium salt of 3-{3-[(2,4-dioxo-3-propyl-1,2,3,4-tetrahydroquinazolin-6-yl)carbonyl]imidazo[1,5-a]pyridin-1-yl}benzoic acid (compound No. 10)

Methyl 2-amino-5-[1-bromo-(imidazo[1,5-a]pyridine-3-yl)carbonyl)]benzoate 0.42 g (2.4 mmol) of N-bromosuccinimide is added, under a nitrogen atmosphere at ambient temperature, to a solution of 0.67 g (2.4 mmol) of methyl 2-amino-5-(imidazo[1,5-a]pyridine-3-ylcarbonyl)benzoate in 20 ml of dichloromethane. After stirring for 2 h 30 minutes, water is added. The precipitate obtained is filtered off, rinsed with water and dried overnight at 40° C. under reduced pressure. 0.77 g of a yellow solid is obtained.
Melting point: 230° C.
MH+: 375, 377

Methyl 2-amino-5-({1-[3-(methoxycarbonyl)phenyl]imidazo[1,5-a]pyridin-3-yl}carbonyl)benzoate 0.248 g (1.38 mmol) of [4-(methoxycarbonyl)phenyl]boronic acid, 0.57 g (2.30 mmol) of potassium carbonate in 2 ml of water, and 0.027 g (0.02 mmol) of tetrakis(triphenylphosphine)palladium are added to a solution of 0.43 g (1.15 mmol) of methyl 2-amino-5-[1-bromo(imidazo[1,5-a]pyridine-3-yl)carbonyl)]benzoate in 10 ml of DME, under an inert argon atmosphere. The reaction medium is heated at 90° C. for 2 hours. The reaction medium is acidified with an aqueous 1N hydrochloric acid solution, and extracted with dichloromethane. The organic phase is washed with water, dried over sodium sulphate, filtered and concentrated under reduced pressure. The residue obtained is placed in solution in 5 ml of DMF. 30 µl (0.5 mmol) of methyl iodide and 0.052 g (0.16 mmol) of caesium carbonate are added. After stirring the 24 hours at ambient temperature, the reaction medium is hydrolysed with water and then extracted with ethyl acetate. The organic phase is dried over sodium sulphate, filtered and then concentrated under reduced pressure. The solid obtained is taken up in methanol. After filtration and drying overnight at 50° C. under reduced pressure, 0.379 g of a yellow solid is obtained.
Melting point: 203° C.
MH+: 430

Methyl 5-({1-[3-(methoxycarbonyl)phenyl]imidazo[1,5-a]pyridin-3-yl}carbonyl)-2-[(propylcarbamoyl)amino]benzoate 0.181 g (0.61 mmol) of triphosgene is added to 0.75 g (0.87 mmol) of methyl 2-amino-5-({1-[3-(methoxycarbonyl)phenyl]imidazo[1,5-a]pyridin-3-yl}carbonyl)benzoate in 10 ml of dioxane, under an inert atmosphere. The reaction medium is heated at 100° C. for 3 hours. 0.14 ml (1.75 mmol) of propylamine and 0.37 ml (2.62 mmol) of triethylamine are added at ambient temperature. After stirring for 2 hours at ambient temperature, the reaction medium is hydrolysed with water. The medium is filtered, washed with water, and dried under reduced pressure at 50° C. overnight. The yellow solid obtained is purified by silica gel column chromatography with a dichloromethane/methanol (95/5) mixture. 0.27 g of a yellow solid is obtained.
Melting point: 212° C.
MH+: 515

3-{3-[(2,4-Dioxo-3-propyl-1,2,3,4-tetrahydroquinazolin-6-yl)carbonyl]imidazo[1,5-a]pyridin-1-yl}benzoic acid 1.31 ml (1.31 mmol) of an aqueous 1N sodium hydroxide solution is added to 0.27 g (0.52 mmol) of methyl 5-({1-[3-(methoxycarbonyl)phenyl]imidazo[1,5-a]pyridin-3-yl}carbonyl)-2-[(propylcarbamoyl)amino]benzoate in 8 ml of methanol. The reaction medium is heated at 70° C. for 5.5 hours. The methanol is concentrated under reduced pressure. The residue is taken up in water. The aqueous phase is acidified with an aqueous 1N hydrochloric acid solution, and then extracted with dichloromethane. The organic phase is dried over sodium sulphate, filtered and then concentrated under reduced pressure. The solid obtained is taken up in methanol and then filtered and dried at 50° C. under reduced pressure overnight. 0.245 g of a yellow solid is obtained.
Melting point: 365° C.
MH+: 469

Sodium salt of 3-{3-[(2,4-dioxo-3-propyl-1,2,3,4-tetrahydroquinazolin-6-yl)carbonyl]imidazo[1,5-a]pyridin-1-yl}benzoic acid 0.51 ml (0.51 mmol) of an aqueous 1 N sodium hydroxide solution is added to 0.245 g (0.52 mmol) of 3-{3-[(2,4-dioxo-3-propyl-1,2,3,4-tetrahydroquinazolin-6-yl)carbonyl]imidazo[1,5-a]pyridin-1-yl}benzoic acid in 5 ml of methanol. The reaction medium is stirred for 1.5 hours at ambient temperature. After the addition of diisopropyl ether, the precipitate formed is filtered off, rinsed with diisopropyl ether, and dried at 50° C. under reduced pressure overnight. 0.242 g of a yellow solid is obtained.
Melting point: 383° C.
MH+: 469
$^1$H-NMR (D6-DMSO, 400 MHz): 0.90 (t, J=7.82 Hz, 3H), 1.58-1.67 (m, 2H), 3.88 (t, J=7.07 Hz, 1H), 7.32-7.35 (m, 2H), 7.45 (t, J=7.82 Hz, 1H), 7.53 (t, J=7.82 Hz, 1H), 7.88-7.94 (m, 2H), 8.22 (d, J=8.94 Hz, 1H), 8.44 (t, J=1.7 Hz, 1H), 8.74 (d, J=8.7 Hz, 1H), 9.14 (d, J=1.9 Hz, 1H), 9.82 (d, J=7 Hz, 1H), 11.9 (bs, 1H)

EXAMPLE 3

3-[(2,4-Dioxo-3-propyl-1,2,3,4-tetrahydroquinazolin-6-yl)carbonyl]imidazo[1,5-a]pyridine-6-carboxylic acid (compound No. 8)

3-[(4-Amino-3-carboxyphenyl)carbonyl]imidazo[1,5-a]pyridine-6-carboxylic acid 3.68 ml (0.026 mol) of triethylamine and then, under a nitrogen atmosphere at ambient temperature, 1.5 g (8.5 mmol) of methyl imidazo[1,5-a]pyridine-6-carboxylate [described in WO 06/097625] are added to 4.02 g (0.014 mol) of 4-oxo-2-phenyl-4H-3,1-benzoxazine-6-carbonyl chloride in 60 ml of 1,2-dichloroethane. After stirring for 24 hours at ambient temperature, the reaction medium is filtered, and washed with 1,2-dichloroethane, then with an aqueous 1 N hydrochloric acid solution and then with water. After drying overnight under reduced pressure at 40° C., the product obtained is dissolved in 60 ml of an NMP. 3.59 g (6.4 mmol)

of potassium hydroxide dissolved in 11 ml of water are added. The reaction medium is heated at 100° C. for 8 hours and then poured onto an aqueous 1N hydrochloric acid solution. After filtration, the solid obtained is rinsed with water and then dried overnight in an incubator under reduced pressure at 40° C. 5.45 g of a yellow solid are obtained.

MH+: 326

Methyl 3-{[4-amino-3-(methoxycarbonyl)phenyl]carbonyl}imidazo[1,5-a]pyridine-6-carboxylate 9.4 g (2.9 mmol) of caesium carbonate and then 1.8 ml (2.9 mmol) of methyl iodide at ambient temperature are added, under an inert atmosphere, to 4.2 g (1.3 mmol) of 3-[(4-amino-3-carboxyphenyl)carbonyl]imidazo[1,5-a]pyridine-6-carboxylic acid in 60 ml of DMF. After stirring for 4.5 hours at ambient temperature, the reaction medium is hydrolysed with water. The precipitate obtained is filtered off, rinsed with water and then dried at 40° C. under reduced pressure overnight. The solid obtained is purified by silica gel column chromatography, elution being carried out with dichloromethane. 1.3 g of a yellow solid are obtained.

MH+: 354

Methyl 3-({3-(methoxycarbonyl)-4-[(propylcarbamoyl)amino]imidazo[1,5-a]pyridine-6-carboxylate 0.14 g (0.49 mmol) of triphosgene is added, at ambient temperature under a nitrogen atmosphere, to 0.3 g (0.7 mmol) of methyl 3-{[4-amino-3-(methoxycarbonyl)phenyl]carbonyl}imidazo[1,5-a]pyridine-6-carboxylate in 10 ml of anhydrous dioxane. After heating for 1 h 15 minutes at 100° C., 0.12 ml (1.4 mmol) of n-propylamine and 0.29 ml (2 mmol) of triethylamine are added to the reaction medium at ambient temperature. After stirring for 4 hours at ambient temperature, the reaction medium is hydrolysed with water. The precipitate obtained is filtered off, rinsed with water and then dried under reduced pressure at 40° C. overnight. The solid obtained is triturated from THF and then filtered and dried under reduced pressure at 40° C. overnight. 0.21 g of a yellow solid is obtained.

Melting point: 266° C.
MH+: 439

3-[(2,4-Dioxo-3-propyl-1,2,3,4-tetrahydroquinazolin-6-yl)carbonyl]imidazo[1,5-a]pyridine-6-carboxylic acid 1.2 ml (1.2 mmol) of an aqueous 1N sodium hydroxide solution are added, at ambient temperature, to 0.21 g of methyl 3-({3-(methoxycarbonyl)-4-[(propylcarbamoyl)amino]imidazo[1,5-a]pyridine-6-carboxylate in 5 ml of methanol. After heating at reflux for 4 hours, the reaction medium is acidified with an aqueous 1N hydrochloric acid solution. The precipitate obtained is filtered off and then rinsed with water and dried under reduced pressure at 40° C. overnight. The solid obtained is recrystallized under hot conditions from methanol and then dried under reduced pressure at 40° C. overnight. 0.118 g of a yellow solid is obtained.

Melting point: 384° C.
MH+: 393
$^1$H-NMR (D6-DMSO, 400 MHz): 0.92 (t, J=7.2 Hz, 3H), 1.59-1.68 (m, 2H), 3.87-3.94 (m, 2H), 7.33 (d, J=8.2 Hz, 1H), 7.72 (d, J=9.3 Hz, 1H), 7.98 (s, 1H), 8.06 (d, J=9.3 Hz, 1H), 8.59 (d, J=8.51 Hz, 1H), 9.20 (d, J=2.03 Hz, 1H), 11.8 (s, 1H), 13.7 (s, 1H)

EXAMPLE 4

Sodium salt of 3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzoic acid (compound No. 49)

Methyl 2-{[(4-fluorobenzyl)carbamoyl]amino}-5-({1-[3-(methoxycarbonyl)phenyl]imidazo[1,5-a]pyridin-3-yl}carbonyl)benzoate 2.14 g (7.2 mmol) of triphosgene are added at ambient temperature and under an inert atmosphere to 2.58 g (6 mmol) of methyl 2-amino-5-({1-[3-(methoxycarbonyl)phenyl]imidazo[1,5-a]pyridin-3-yl}carbonyl)benzoate in 50 ml of dioxane. After heating for 7 hours at reflux, 2.25 g (18 mmol) of 4-fluorobenzylamine and 1.82 g (18 mmol) of triethylamine are added at ambient temperature. The reaction medium is heated for 3 hours at reflux and then concentrated under reduced pressure. The residue is triturated from water. After filtration, the solid is rinsed with methanol and then dried under reduced pressure at 40° C. overnight. 3.3 g of a yellow solid are obtained.

MH+: 581

3-(3-{[3-(4-Fluorobenzyl)-2,4-dioxo-1,2,3,4-tetrahydroquinazolin-6-yl]carbonylimidazo[1,5-a]pyridin-1-yl}benzoic acid 2.85 ml (0.0285 mol) of an aqueous 1N sodium hydroxide solution are added to 3.3 g (5.7 mmol) of methyl 2-{[(4-fluorobenzyl)carbamoyl]amino}-5-({1-[3-(methoxycarbonyl)phenyl]-imidazo[1,5-a]pyridin-3-yl}carbonyl)benzoate dissolved in 250 ml of methanol. After heating at reflux for 2 hours, the reaction medium is acidified with 50 ml of an aqueous 1N hydrochloric acid solution and then diluted with 700 ml of water. The precipitate obtained is filtered off, and dried under reduced pressure at 40° C. overnight. 3.01 g of a yellow solid are obtained.

MH+: 535

Methyl 3-(3-{[3-(4-fluorobenzyl)-1-methyl-2,4-dioxo-1,2,3,4-tetrahydro quinazolin-6-yl]carbonyl}imidazo[1,5-a]pyridin-1-yl)benzoate 2.44 g (7.5 mmol) of caesium carbonate and 1.06 g (7.5 mmol) of methyl iodide are added, under an inert atmosphere, to 1.3 g (2.5 mmol) of 3-(3-{[3-(4-fluorobenzyl)-2,4-dioxo-1,2,3,4-tetrahydroquinazolin-6-yl]carbonylimidazo[1,5-a]pyridin-1-yl}benzoic acid in 50 ml of DMF. The reaction medium is stirred for 3 hours at ambient temperature under a nitrogen atmosphere and then concentrated under reduced pressure. The residue obtained is washed with 200 ml of water and then dried under reduced pressure at 40° C. overnight. 1.35 g of a yellow solid are obtained.

MH+: 563

Sodium salt of 3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzoic acid 24 ml (24 mmol) of an aqueous 1N lithium hydroxide solution are added to 1.3 g (2.4 mmol) of methyl 3-(3-{[3-

(4-fluorobenzyl)-1-methyl-2,4-dioxo-1,2,3,4-tetrahydroquinazolin-6yl]carbonyl}imidazo[1,5-a]pyridin-1-yl)benzoate in 120 ml of THF. The reaction medium is heated for 5 hours at reflux and then acidified at 5° C. with 45 ml of an aqueous 1 N hydrochloric acid solution and, finally, diluted with 200 ml of water. After filtration, the residue obtained is dried under reduced pressure at 40° C. overnight. 0.62 ml (0.62 mmol) of an aqueous 1 N sodium hydroxide solution is added to 0.35 g (0.64 mmol) of the yellow solid obtained, in 20 ml of methanol. After filtration, the residue obtained is dried under reduced pressure at 40° C. overnight. 0.38 g of a yellow solid is obtained.

MH+: 549

$^1$H-NMR (D6-DMSO, 500 MHz): 3.62 (s, 3H), 5.17 (s, 2H), 7.11-7.18 (ps t, J=8.9 Hz, 2H), 7.35-7.40 (ps t, 8.9 Hz, 1H), 7.42-7.48 (m, 3H), 7.54-7.60 (ps t, J=8.9 Hz, 1H), 7.70-7.74 (ps d, J=8.9 Hz, 1H), 7.89-7.95 (ps t, J=8.9 Hz, 2H), 8.26-8.30 (ps d, J=8.9 Hz, 1H), 8.44-8.48 (m, 1H), 8.96-9.01 (ps d, J=8.9 Hz, 1H), 9.22-9.24 (m, 1H), 9.88-9.91 (ps d, J=7.2 Hz, 1H)

EXAMPLE 5

3-{3[(2,4-Dioxo-3-propyl-1,2,3,4-tetrahydroquinazolin-6-yl)carbonyl]imidazo[1,5-a]pyridin-1-yl}benzamide (compound No. 29)

10.7 mg (0.2 mmol) of ammonium chloride, 5.17 mg (0.4 mmol) of N,N-diisopropylethylamine and 49.2 mg (0.2 mmol) of TOTU are added, at 0° C. under an inert atmosphere, to 46.8 mg (0.1 mmol) of 3-{3-[(2,4-dioxo-3-propyl-1,2,3,4-tetrahydroquinazolin-6-yl)carbonyl]imidazo[1,5-a]pyridin-1-yl}benzoic acid in 2 ml of DMF. The reaction medium is stirred for 12 hours at ambient temperature and then poured onto 30 ml of a saturated sodium hydrogen carbonate solution. The precipitate obtained is filtered off, washed with water, and then dried under reduced pressure at 40° C. overnight. 0.042 g of a yellow solid is obtained.

MH+: 468

$^1$H-NMR (D6-DMSO, 500 MHz): δ=0.92 (t, 3H, J=7.7 Hz), 1.66 (tq, 2H, J=7.7 Hz, 7.3 Hz), 3.94 (t, 2H, J=7.3 Hz), 7.34-7.42 (2 m, 2H), 7.52-7.61 (2m, 2H), 7.69 (t, 1H, J=7.6 Hz), 7.96 (m, 1H), 8.10-8.23 (2 m, 2H), 8.41-8.46 (m, 2H), 8.80 (dd, 1H, J=8.9 Hz, 2.2 Hz), 9.27 (d, 1H, 1.9 Hz), 9.88 (d, 1H, J=7.1 Hz), 11.83 (s, 1 H)

EXAMPLE 6

6-({1-[3-(5-Methyl-1,3,4 oxadiazol-2-yl)phenyl] imidazo[1,5-a]pyridin-3-yl}carbonyl-3-propylquinazoline-2,4(1H, 3H)-dione (compound No. 34)

N'-acetyl-3-{3-[2,4-dioxo-3-propyl-1,2,3,4-tetrahydroquinazolin-6-yl]carbonyl}imidazo[1,5-a]pyridin-1-yl}benzohydrazide 29.6 mg (0.4 mmol) of acetohydrazide, 98.4 mg (0.3 mmol) of TOTU and 0.104 ml (0.6 mmol) of N,N-diisopropylethylamine are added, under an inert atmosphere, at 0° C., to 93.7 mg (0.2 mmol) of 3-{3-[(2,4-dioxo-3-propyl-1,2,3,4-tetrahydroquinazolin-6-yl)carbonyl]imidazo[1,5-a]pyridin-1-yl}benzoic acid in 6 ml of DMF. The reaction medium is stirred for 1 hour at 0° C., then for 6 hours at 50° C., and then concentrated under reduced pressure. The residue is taken up in 10 ml of methanol. The precipitate obtained is filtered off, washed with diethyl ether and with pentane, and then dried under reduced pressure at 40° C. overnight. 45 mg of a yellow solid are obtained.

MH+: 525

6-({1-[3-(5-Methyl-1,3,4 oxadiazol-2-yl)phenyl] imidazo[1,5-a]pyridin-3-yl}carbonyl-3-propylquinazoline-2,4(1H, 3H)-dione 35 mg (0.066 mmol) of N'-acetyl-3-{3-[2,4-dioxo-3-propyl-1,2,3,4-tetrahydroquinazolin-6-yl]carbonyl}imidazo[1,5-a]pyridin-1-yl}benzohydrazide in 1 ml of phosphorus oxychloride are heated at 100° C. for 15 minutes. The reaction medium is concentrated under reduced pressure. The residue obtained is hydrolysed with water and with a saturated sodium hydrogen carbonate solution. The aqueous phase is extracted with dichloromethane. The organic phase is concentrated under reduced pressure. The solid obtained is purified by silica gel column chromatography, elution being carried out with methanol. 0.025 g of a yellow solid is obtained.

MH+: 507

$^1$H-NMR (D6-DMSO, 500 MHz): 0.91 (t, J=7.5 Hz, 3H), 1.65 (qt, J=7.5 Hz, 7.5 Hz, 2 H), 2.67 (s, 3H), 3.93 (t, J=7.5 Hz, 2 H), 7.33-7.43 (m, 2 H), 7.58-7.64 (m, 1H), 7.77-7.84 (m, 1H), 8.04-8.06 (m, 1 H), 8.28-8.32 (m, 1H), 8.39-8.43 (m, 1H), 8.59 (s, 1H), 8.71-8.74 (m, 1H), 9.37 (s, 1H), 9.86-9.90 (s, 1H), 11.85 (br s, 1H)

EXAMPLE 7

6-({1-[3-(3-Methyl-1,2,4-oxadiazol-5-yl)phenyl] imidazo[1,5-a]pyridin-3-yl}carbonyl)-3-propylquinazoline-2,4(1H, 3H)-dione (compound No. 36)

3-{34(2,4-Dioxo-3-propyl-1,2,3,4-tetrahydroquinazoli-6-ylcarbonyl) imidazo[1,5-a]pyridi-1-A-N-[(1E)-hydroxyethanimidoyl]benzamide 39 mg (0.24 mmol) of 1,1'-carbonyldiimidazole are added, at ambient temperature under an inert atmosphere, to 94 mg (0.2 mmol) of 3-{3-[(2,4-dioxo-3-propyl-1,2,3,4-tetrahydroquinazolin-6-yl)carbonyl]imidazo[1,5-a]pyridin-1-yl}benzoic acid in 5 ml of DMF. After stirring for 12 hours at ambient temperature, 22.2 mg (0.3 mmol) of acetamidoxime are added. The reaction medium is stirred for 5 hours at ambient temperature and then concentrated under reduced pressure. The residue is triturated from diethyl ether, filtered and then dried under reduced pressure at 40° C. overnight. 0.101 g of a yellow solid is obtained.

MH+: 525

6-({1-[3-(3-Methyl-1,2,4-oxadiazol-5-yl)phenyl] imidazo[1,5-a]pyridin-3-yl}carbonyl)-3-propylquinazoline-2,4(1H, 3H)-dione A solution of 0.1 g (0.19 mmol) of 3-{3-[(2,4-dioxo-3-propyl-1,2,3,4-tetrahydroquinazoli-6-ylcarbonyl)imidazo[1,5-a]pyridi-1-yl]-N-[(1E)-hydroxyethan imidoyl]benzamide in 3 ml of DMF is heated at 120° C. for 5 hours. The reaction medium is concentrated under reduced pressure. The residue obtained is taken up in diethyl ether, filtered and then dried under reduced pressure at 40° C. overnight. 0.083 g of a yellow solid is obtained.

MH+: 507

$^1$H-NMR (D6-DMSO): 0.91 (t, J=7.5 Hz, 3H), 1.65 (qt, J=7.5 Hz, 7.5 Hz, 2H), 2.47 (s, 3H), 3.94 (t, J=7.5 Hz, 2H), 7.36-7.45 (m, 2H), 7.59-7.66 (m, 1H), 7.82-7.89 (m, 1H), 8.13-8.19 (m, 1H), 8.36-8.45 (m, 2H), 8.68 (s, 1H), 8.75-8.79 (m, 1H), 9.25. 9.28 (m, 1H), 9.85-9.90 (m, 1H), 11.85 (br s, 1H)

EXAMPLE 8

N-{3-[(2,4-dioxo-3-propyl-1,2,3,4-tetrahydroquinazolin-6-yl)carbonyl]imidazo[1,5-a]pyridin-1-yl}methanesulphonamide (compound No. 13)

Methyl 5-[(1-bromoimidazo(1,5-a)pyridin-3-yl)carbonyl]-2-(propyl carbamoyl)aminobenzoate 0.55 g (0.0019 mol) of triphosgene are added, at ambient temperature under an inert atmosphere, to 1 g (2.7 mmol) of methyl 2-amino-5-[1-bromo-(imidazo[1,5-a]pyridine-3-yl)carbonyl)]benzoate in 30 ml of anhydrous dioxane. The reaction medium is heated for 1.5 hours at 100° C. 0.44 ml (5.3 mmol) of n-propylamine and 1.12 ml (8 mmol) of triethylamine are added at ambient temperature. After 2 h 30 minutes, the reaction medium is hydrolysed with water. The aqueous phase is extracted with dichloromethane. The organic phase is dried over sodium sulphate, filtered and then concentrated under reduced pressure. The solid obtained is triturated from dichloromethane, filtered and then dried under reduced pressure at 40° C. overnight.

MH+: 459, 461

Melting point: 236° C.

6-[(1-Bromoimidazo(1,5-a)pyridin-3-yl)carbonyl]-3-propylquinazoline-2,4(1H,3H)-dione 3.14 ml (3.1 mmol) of an aqueous 1N sodium hydroxide solution are added, at ambient temperature, to 1.2 g (2.6 mmol) of methyl 5-[(1-bromoimidazo(1,5-a)pyridin-3-yl)carbonyl]-2-[(propylcarbamoyl)aminobenzoate in 20 ml of methanol. After heating at reflux for 3 hours, the reaction medium is hydrolysed with an aqueous 1 N hydrochloric acid solution. The precipitate obtained is filtered off, rinsed with methanol and dried under reduced pressure at 40° C. overnight. 1.09 g of a yellow solid are obtained.

MH+: 427, 429

Melting point: 322° C.

6-[(1-Aminoimidaz(1,5-a)pyridin-3-yl)carbonyl]-3-propylquinazoline-2,4(1H,3H)-dione 1.45 g (4.7 mmol) of caesium carbonate, 1.13 ml (6.7 mmol) of benzophenone imine, 0.278 g (0.45 mmol) of binap and 0.204 g (0.22 mmol) of (dibenzilideneacetone)dipalladium are added, at ambient temperature under an argon atmosphere, to 0.955 g (2 mmol) of 6-[(1-bromoimidazo(1,5-a)pyridin-3-yl)carbonyl]-3-propylquinazoline-2,4(1H,3H)-dione in 20 ml of DMSO. The reaction medium is heated at 110° C. for 18 hours. The reaction medium is extracted with ethyl acetate. The organic phase is dried over sodium sulphate, filtered and concentrated under reduced pressure.

The residue obtained is dissolved in 40 ml of THF. 4.5 ml (9 mmol) of an aqueous 2N hydrochloric acid solution are added at ambient temperature. After stirring for 4 hours at ambient temperature, the reaction medium is concentrated under reduced pressure. The residue obtained is washed with dichloromethane and with methanol, and then dried under reduced pressure at 40° C. overnight. 0.558 g of a red solid is obtained.

MH+: 364

N-{3-[(2,4-dioxo-3-propyl-1,2,3,4-tetrahydroquinazolin-6-yl)carbonyl]imidazo[1,5-a]pyridin-1-yl}methanesulphonamide 0.1 ml (1.2 mmol) of mesyl chloride is added, at 0° C. under an inert atmosphere, to 0.25 g (0.4 mmol) of 6-[(1-aminoimidazo(1,5-a)pyridin-3-yl)carbonyl]-3-propylquinazoline-2,4(1H,3H)-dione in 5 ml of pyridine. After the addition of methanol, the reaction medium is concentrated under reduced pressure. The residue is taken up with dichloromethane. The organic phase is washed with an aqueous 1N hydrochloric acid solution and then with water, dried over sodium sulphate, filtered and concentrated under reduced pressure. The residue is recrystallized under hot conditions from methanol, and purified on a silica gel frit, elution being carried out with DMF. 0.057 g of an orange solid is obtained.

Melting point: 334° C.

MH+: 442

$^1$H-NMR (D6-DMSO, 400 MHz): 0.88 (t, J=7.37 Hz, 3H), 1.55-1.65 (m, 2H), 3.29 (s, 3H), 3.87-3.90 (m, 2H), 7.27-7.31 (m, 2H), 7.40-7.44 (m, 1H), 7.92 (d, J=9 Hz, 1H), 8.52 (d, J=8.46 Hz, 1H), 9.15 (d, J=2.18 Hz, 1H), 9.71 (d, J=7.1 Hz, 1H), 10.2 (s, 1H), 11.8 (s, 1H)

EXAMPLE 9

2-Morpholin-4-ylethyl 3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzoate hydrochloride (compound No. 82)

0.022 g (0.61 mmol) of 4-(2-chloroethyl)morpholine hydrochloride and 0.189 g (1.37 mmol) of potassium carbonate are added, under an inert atmosphere, to 0.3 g (0.55 mmol) of 3-(3-{[3-(4-fluorobenzyl)-1-methyl-2,4-dioxo-1,2,3,4-tetrahydroquinazolin-6-yl]carbonyl}imidazo[1,5-a]pyridin-1-yl) acid in 8 ml of DMF. After stirring for 18 h at ambient temperature and then 8 hours at 50° C., the reaction medium is hydrolysed with water and extracted with ethyl acetate. The organic phase is washed with water, dried over sodium sulphate, filtered and then concentrated under reduced pressure. The yellow solid obtained is purified by silica gel column chromatography, elution being carried out with a dichloromethane/methanol (95/5) mixture. 0.61 ml of an aqueous 1 N hydrochloric acid solution is added to 0.334 g of the yellow solid obtained, in 5 ml of methanol. The reaction medium is stirred for 1 hour at ambient temperature. Diethyl ether is added, and the reaction medium is then filtered. The precipitate obtained is rinsed with diethyl ether, and then dried under reduced pressure at 50° C. overnight. 0.298 g of a yellow solid is obtained.

Melting point: 215° C.

MH+: 662

$^1$H-NMR (D6-DMSO, 500 MHz): 3.21-3.31 (m, 2H), 3.31 (s, 3H), 3.46-3.54 (m, 2H), 3.6-3.7 (m, 2H), 3.61 (s, 3H), 3.70-3.80 (m, 2H), 3.90-4 (m, 2H), 4.65-4.75 (m, 2H), 5.16 (s, 2H), 7.11-7.16 (m, 2H), 7.37-7.39 (m, 1H), 7.42-7.45 (m, 2H), 7.55-7.58 (m, 1H), 7.67 (d, J=9.28 Hz, 1H), 7.73 (t, J=7.69 Hz, 1H), 8.07 (d, J=7.69 Hz, 1H), 8.29-8.34 (m, 2H), 8.55 (s, 1H), 8.82 (d, J=9.01 Hz, 1H), 9.27 (d, J=1.85 Hz, 1H), 9.83 (d, J=7.16 Hz, 1H), 10.9 (s, 1H)

EXAMPLE 10

N-[2-(dimethylamino)ethyl]-3-(3-{[3-(4-fluorobenzyl)-1-methyl-2,4-dioxo-1,2,3,4-tetrahydroquinazolin-6-yl]carbonyl}imidazo[1,5-a]pyridin-1-yl)benzamide hydrochloride (compound No. 116)

0.06 ml (0.55 mmol) of N,N-dimethylethylenediamine, 0.134 g (0.41 mmol) of TOTU and 0.14 ml (0.82 mmol) of diisopropylethylamine are added to 0.15 g (0.27 mmol) of 3-(3-{[3-(4-fluorobenzyl)-1-methyl-2,4-dioxo-1,2,3,4-tetrahydroquinazolin-6-yl]carbonyl}imidazo[1,5-a]pyridin-1-yl) benzoic acid in 5 ml of DMF. The reaction medium is heated at 80° C. for 16 hours. The reaction medium is hydrolysed with water, and extracted with ethyl acetate. The organic phase is washed with water, dried over sodium sulphate, filtered and concentrated under reduced pressure. The yellow solid obtained is purified by silica gel column chromatography, elution being carried out with a dichloromethane/methanol (95/5) mixture. 0.23 ml of an aqueous 1N hydrochloric acid solution in diethyl ether is added to 0.095 g of the yellow solid obtained. After stirring for 1 hour, diethyl ether is added. The precipitate obtained is filtered off, rinsed with water and then dried under reduced pressure at 50° C. overnight. 0.1 g of a yellow solid is obtained.

Melting point: 247° C.
MH+: 619
$^1$H-NMR (D6-DMSO, 400 MHz): 2.50 (m, 6H), 2.84 (s, 2H), 3.31 (s, 3H), 3.61(s, 1H), 3.64-6.70 (m, 1H), 5.16 (s, 2H), 7.7.11-7.17 (m, 2H), 7.37-7.46 (m, 3H), 7.55-7.60 (m, 1H), 7.67-7.71 (m, 2H), 7.93 (d, J=8.19 Hz, 1H), 8.19 (d, J=7.51 Hz, 1H), 8.38-8.43 (m, 2H), 8.87 (d, J=8.88 Hz, 1H), 8.92 (t, J=5.12 Hz, 1H), 9.27 (d, J=2Hz, 1H), 9.81 (s, 1H), 9.84 (d, J=7.1 Hz, 1H)

EXAMPLE 11

Sodium salt of 3-(3-{[3-(4-fluorobenzyl)-1-propyl-2,4-dioxo-1,2,3,4-tetrahydroquinazolin-6-yl]carbonyl}imidazo[1,5-a]pyridin-1-yl)benzoic acid (compound No. 72)

Propyl 3-(3-{[3-(4-fluorobenzyl)-1-Propyl-2,4-dioxo-1,2,3,4-tetrahydroquinazolin-6-yl]carbonyl}imidazo[1,5-a]pyridin-1-yl)benzoate 1.371 g (4.21 mmol) of caesium carbonate and 0.715 g (4.21 mmol) of propyl iodide are added, under an inert atmosphere, to 0.75 g (1.4 mmol) of 3-(3-{[3-(4-fluorobenzyl)-2,4-dioxo-1,2,3,4-tetrahydroquinazolin-6-yl]carbonylimidazo[1,5-a]pyridin-1-yl}benzoic acid in 30 ml of DMF. The reaction medium is stirred for 3 hours at ambient temperature under a nitrogen atmosphere and then concentrated under reduced pressure. The residue obtained is washed with 100 ml of water and then dried under reduced pressure at 40° C. overnight. The solid obtained is purified by silica gel column chromatography, elution being carried out with a dichloromethane/methanol (75/1) mixture. 0.55 g of a yellow solid is obtained.
MH+: 619

Sodium salt of 3-(3-{[3-(4-fluorobenzyl)-1-propyl-2,4-dioxo-1,2,3,4-tetrahydroquinazolin-6-yl]carbonyl}imidazo[1,5-a]pyridin-1-yl)benzoic acid 8.9 ml (8.9 mmol) of an aqueous 1N lithium hydroxide solution are added to 0.55 g (0.889 mmol) of propyl 3-(3-{[3-(4-fluorobenzyl)-1-propyl-2,4-dioxo-1,2,3,4-tetrahydroquinazolin-6-yl]carbonyl}imidazo[1,5-a]pyridin-1-yl)benzoate in 50 ml of THF. The reaction medium is heated for 6 hours at reflux and then acidified at 5° C. with 17 ml of an aqueous 1N hydrochloric acid solution and, finally, diluted with 100 ml of water. After filtration, the residue obtained is dried under reduced pressure at 40° C. overnight.

0.408 ml (0.408 mmol) of an aqueous 1N sodium hydroxide solution is added to 0.24 g (0.416 mmol) of the yellow solid obtained, in 20 ml of methanol. After filtration, the residue obtained is dried under reduced pressure at 40° C. overnight. 0.24 g of a yellow solid is obtained.

MH+: 577
$^1$H-NMR (D6-DMSO, 500 MHz): 0.97 (t, J=7.5 Hz, 3H, 1.71 (tq, $J_1/J_2$=7.5 Hz, 2H), 4.18 (t, J=7.5 Hz, 2H), 5.20 (s, 2H), 7.17 (ps t, J=9.3 Hz, 2H), 7.37-7.41 (m, 1H), 7.44-7.49 (3 m, 3H), 7.59 (m, 1H), 7.78 (ps d, J=8.5 Hz, 1H), 7.91 (2 m, 2H), 8.28 (ps d, J=9.8 Hz, 1H), 8.45 (m, 1H), 8.99-9.02 (m, 1H), 9.23 (m, 1H), 9.90 (ps d, J=7.5 Hz, 1H)

EXAMPLE 12

3-(4-Fluorobenzyl)-1-methyl-6-[(1-pyridin-3-ylimidazo[1,5-a]pyridin-3-yl)carbonyl]quinazoline-2,4 (1H, 3H)-dione (compound No. 112)

Methyl 5-[(1-bromoimidazo[1,5-a]pyridin-3-yl)carbonyl]-2-{[(4-fluorobenzyl)carbamoyl] amino}benzoate 3 g (10.4 mmol) of triphosgene diluted in 40 ml of dioxane are added to 5.57 g (14.9 mmol) of methyl 2-amino-5-[1-bromo-(imidazo[1,5-a]pyridine-3-yl)carbonyl)]benzoate in 160 ml of dioxane, under an inert atmosphere. The reaction medium is heated at reflux for 1 hour. 3.7 g (0.030 mol) of 4-fluorobenzylamine and 6.22 ml (0.045 mol) of triethylamine are added at ambient temperature. The reaction medium is stirred for 4 hours at ambient temperature and then hydrolysed with water. The precipitate obtained is filtered off, rinsed with water and dried under reduced pressure at 50° C. overnight. The solid obtained taken up with methanol, filtered, rinsed with methanol, and dried under reduced pressure overnight. 12 g of a yellow solid are obtained (yield=95.5%).

MH+: 525, 527
Melting point: 203° C.

6-[(1-Bromoimidazo[1,5-a]pyridin-3-yl)carbonyl]-3-(4-fluorobenzyl)quinazoline-2,4(1H, 3H)-dione 22.33 ml (22.33 mmol) of an aqueous 1N sodium hydroxide solution are added to 7.8 g (0.0149 mol) of methyl 5-[(1-bromoimidazo[1,5-a]pyridin-3-yl)carbonyl]-2-{[(4-fluorobenzyl)carbamoyl]amino}benzoate in 100 ml of methanol. The reaction medium is heated for 2.5 hours at reflux. After hydrolysis with water, the precipitate obtained is filtered off, rinsed with water and dried under reduced pressure at 50° C. overnight.

The solid obtained is taken up in an aqueous 0.1N hydrochloric acid solution, rinsed with water, and dried under reduced pressure at 50° C. overnight. 5.4 g of a yellow solid are obtained.

Melting point: 325° C.

MH+: 494, 496

6-[(1-Bromoimidazo[1,5-a]pyridin-3-yl)carbonyl]-3-(4-fluorobenzyl)-1-methylquinazoline-2,4(1H, 3H)-dione 1.87 g (5.7 mmol) of caesium carbonate and 0.39 ml (6.2 mmol) of methyl iodide are added, at ambient temperature under an inert atmosphere, to 2.6 g (5.17 mmol) of 6-[(1-bromoimidazo[1,5-a]pyridin-3-yl)carbonyl]-3-(4-fluorobenzyl) quinazoline-2,4(1H, 3H)-dione in 50 ml of DMF. The reaction medium is stirred for 18 hours at ambient temperature and then filtered. The precipitate is rinsed with water and then dried under reduced pressure at 50° C. overnight. 2.54 g of a yellow solid are obtained.

Melting point: 280° C.

MH+: 507, 509

3-(4-Fluorobenzyl)-1-methyl-6-[(1-pyridin-3-ylimidazo[1,5-a]pyridin-3-yl)carbonyl]quinazoline-2,4(1H, 3H)-dione 0.04 g (0.32 mmol) of 3-pyridylboronic acid, 0.2 g (0.81 mmol) of potassium phosphate dihydrate dissolved in 0.29 ml of water, and 6.2 mg (0.01 mmol) of tetrakis(triphenylphosphine)palladium are added to 0.15 g (0.27 mmol) of 6-[(1-bromoimidazo[1,5-a]pyridin-3-yl)carbonyl]-3-(4-fluorobenzyl)-1-methylquinazoline-2,4 (1H, 3H)-dione in 3 ml of DMF, under an inert argon atmosphere. The reaction medium is microwave-heated at 150° C. for 20 minutes. After filtration through talc, the reaction medium is concentrated under reduced pressure. The residue obtained is purified by silica gel column chromatography, elution being carried out with a dichloromethane/methanol (95/5) mixture. 0.12 g of a yellow solid is obtained.

Melting point: 207° C.

MH+: 506

3-(4-Fluorobenzyl)-1-methyl-6-[(1-pyridin-3-ylimidazo[1,5-a]pyridin-3-yl)carbonyl]quinazoline-2,4 (1H, 3H)-dione hydrochloride 0.35 ml (0.35 mmol) of a 1N hydrochloric acid solution in diethyl ether is added to 0.12 g (0.23 mmol) of 3-(4-fluorobenzyl)-1-methyl-6-[(1-pyridin-3-ylimidazo[1,5-a]pyridin-3-yl)carbonyl]quinazoline-2,4(1H, 3H)-dione in 3 ml of methanol. After stirring for 1 hour at ambient temperature, the reaction medium is filtered. The precipitate obtained is rinsed with diethyl ether, and dried under reduced pressure at 50° C. overnight. 0.12 g of a yellow solid is obtained.

MH+: 506

Melting point: 267° C.

$^1$H-NMR (D6-DMSO, 400 MHz): 3.60 (s, 3H), 5.16 (s, 2H), 7.14 (t, J=8.34 Hz, 2H), 7.36-7.47 (m, 3H), 7.60 (t, J=7.05 Hz, 1H), 7.65 (d, J=8.98 Hz, 1H), 7.83 (t, J=7.05 Hz, 1H), 8.43 (d, J=8.98 Hz, 1H), 8.66-8.75 (m, 2H), 8.83 (d, J=8.98 Hz, 1H), 9.30(m, 2H), 9.81 (d, J=7.05 Hz, 1H)

EXAMPLE 13

3-{3-[(2-Methyl-4-oxo-3-propyl-3,4-dihydroquinazolin-6-yl)carbonyl]imidazo[1,5-a]pyridin-1-yl}benzoic acid (compound No. 53)

2-Amino-5-(1-bromoimidazo[1,5-a]pyridin-3-ylcarbonyl)benzoic acid 60 ml (60 mmol) of an aqueous 1N sodium hydroxide solution are added, at ambient temperature, to 3.74 g (10 mmol) of methyl 2-amino-5-[1-bromo-(imidazo[1,5-a]pyridine-3-yl)carbonyl)]benzoate in 300 ml of methanol and 125 ml of water. The reaction medium is heated at reflux for 6 hours and then 140 ml of an aqueous 1N hydrochloric acid solution are added. After concentration of the methanol under reduced pressure, the precipitate obtained is filtered off, washed with water and then dried under reduced pressure at 40° C. for 18 hours. 3.53 g of a yellow solid are obtained.

MH+: 360, 362

2-(acetylamino)-5-[(1-bromoimidazo[1,5-a]pyridin-3-yl)carbonyl]benzoic acid 0.92 g (2.56 mmol) of 2-amino-5-(1-bromo-imidazo[1,5-a]pyridin-3-ylcarbonyl)benzoic acid in 30 ml of acetic anhydride are heated for 5.5 hours at reflux. The reaction medium is concentrated under reduced pressure. The residue is taken up in water and then filtered and dried under reduced pressure overnight at 40° C. 1.1 g of a yellow solid are obtained.

MH+: 402, 404

6-[(1-Bromoimidazo[1,5-a]pyridin-3-yl)carbonyl]-2-methyl-3-propylquinazolin-4(3H)-one 1.32 g (22.4 mmol) of n-propylamine are added, at 0° C. under an inert atmosphere, to 0.9 g (2.2 mmol) of 6-[(1-bromoimidazo[1,5-a]pyridin-3-yl)carbonyl]-2-methyl-4H-3,1-benzoxazin-4-one in 15 ml of glacial acetic acid. The reaction medium is microwave-heated at 160° C. for 45 minutes. The reaction medium is concentrated under reduced pressure. The residue obtained is taken up with a saturated aqueous solution of sodium carbonate. The precipitate obtained is filtered off, and then dried under reduced pressure at 50° C. overnight. 0.67 g of a yellow solid is obtained.

MH+: 425, 427

Methyl 3-{3-[(2-methyl-4-oxo-3-propyl-3,4-dihydroquinazolin-6-yl)carbonyl]imidazo[1,5-a]pyridin-1-yl}benzoate 0.35 g (1.95 mmol) of 3-methoxycarbonylphenylboronic acid, 0.689 g (3.24 mmol) of potassium phosphate dissolved in 3 ml of water, and 0.037 g (0.032 mmol) of tetrakis (triphenylphosphine)palladium are added to 0.69 g (1.62 mmol) of 6-[(1-bromoimidazo[1,5-a]pyridin-3-yl)carbonyl]-2-methyl-3-propylquinazolin-4(3H)-one in 15 ml of NMP. The reaction medium is microwave-heated for 15 minutes at 150° C. and then concentrated under reduced pressure. After the addition of 100 ml of water, the precipitate is filtered off and then dried under reduced pressure at 50° C. overnight. The solid obtained is purified by silica gel column chromatography, elution being carried out with a dichloromethane/methanol (50/1) mixture.

MH+: 481

3-{3-[(2-Methyl-4-oxo-3-propyl-3,4-dihydroquinazolin-6-yl)carbonyl]imidazo[1,5-a]pyridin-1-yl}benzoic acid 7.65 ml of an aqueous 1N sodium hydroxide solution are added to 0.735 g (1.53 mmol) of methyl 3-{3-[(2-methyl-4-oxo-3-propyl-3,4-dihydroquinazolin-6-yl)carbonyl]imidazo[1,5-a]pyridin-1-yl}benzoate in 30 ml of THF. The reaction medium is heated for 2.5 hours at reflux. After acidification with 10 ml of an aqueous 1N hydrochloric acid solution, the reaction medium is concentrated under reduced pressure. The residue is taken up in 20 ml of water. The precipitate obtained is filtered off, and dried under reduced pressure at 50° C. overnight. 0.52 g of a yellow solid is obtained.

MH+: 467

$^1$H-NMR (D6-DMSO, 500 MHz): 0.97 (t, J=7.6 Hz, 3 H), 1.69-1.76 (m, 2 H), 2.71 (s, 3H), 4.07-4.11 (m, 2 H), 7.40-7.44 (m, 1H), 7.59-7.66 (m, 1H), 7.71-7.80 (m, 2 H), 8.01-8.05 (m, 1 H), 8.28-8.39 (2 m, 2 H), 8.55-8.58 (m, 1 H), 8.79-8.82 (m, 1 H), 9.30-9.34 (m, 1 H), 9.88-9.22 (m, 1 H), 13.23 (br s, 1H)

EXAMPLE 14

3-{3-[(2-Methyl-4-oxo-3-propyl-3,4-dihydroquinazolin-6-yl)carbonyl]imidazo[1,5-a]pyridin-1-yl}benzamide (compound No. 55)

0.107 g (2 mmol) of ammonium chloride, 0.328 g (1 mmol) of TOTU and 0.517 g (4 mmol) of N,N-diisopropylethylamine are added, at ambient temperature under an inert atmosphere, to 0.233 g (0.5 mol) of 3-{3-[(2-methyl-4-oxo-3-propyl-3,4-dihydroquinazolin-6-yl)carbonyl]imidazo[1,5-a]pyridin-1-yl}benzoic acid in 30 ml of DMF. The reaction medium is stirred for 5 hours at ambient temperature and then concentrated under reduced pressure. 50 ml of a saturated solution of sodium hydrogen carbonate are added to the residue. The precipitate obtained is filtered off, and then dried under reduced pressure at 50° C. overnight. 0.230 g of a yellow solid is obtained.

MH+: 466

$^1$H-NMR (D6-DMSO, 500 MHz): 0.98 (t, J=8 Hz, 3H), 1.74 (m, 2H), 2.71 (s, 3H), 4.10 (t, J=8.1 Hz, 2H), 7.40-7.45 (m, 1H), 7.54-7.64 (m, 2H), 7.67-7.71 (m, 1 H), 7.75-7.80 (m, 1 H), 7.96-8.00 (m, 1 H), 8.19-8.23 (m, 2 H), 8.42-8.48 (m, 2H), 8.82-8.85 (m, 1H), 9.39-9.41 (m, 1 H), 9.90-9.95 (m, 1 H)

EXAMPLE 15

6-(Imidazo[1,5-a]pyridin-3-ylcarbonyl)quinazolin-4(3H)-one (compound No. 3)

0.36 g (3.6 mmol) of formamidine acetate is added to 0.2 g (0.72 mmol) of 2-amino-5-(imidazo[1,5-a]pyridin-3-ylcarbonyl)benzoïc acid (described in WO06/097625) in 7 ml of ethanol. The reaction medium is microwave-heated at 150° C. for 25 minutes. The reaction medium is hydrolysed with an aqueous 1N sodium hydroxide solution. The aqueous phase is extracted with dichloromethane. The heterogeneous organic phase is filtered. The solid obtained is purified by silica gel column chromatography, elution being carried out with a dichloromethane/methanol (90/10) mixture. 54 mg of a yellow solid are obtained.

MH+: 291

Melting point: 289° C.

$^1$H-NMR (D6-DMSO, 400 MHz): 7.29-7.47 (m, 2H), 7.80-7.82 (m, 1H), 7.96 (s, 1H), 8.04-8.07 (m, 1H), 8.23 (s, 1H), 8.67-8.70 (m, 1H), 9.29 (s, 1H), 9.52-9.53 (m, 1H), 12.5 (s, 1H)

EXAMPLE 16

Sodium salt of 3-[3-({3-[2-(4-fluorophenoxy)ethyl]-1-propyl-2,4-dioxo-1,2,3,4-tetrahydroquinazolin-6-yl}carbonyl)imidazo[1,5-a]pyridin-1-yl]benzoic acid (compound No. 221)

Methyl 5-[(1-bromoimidazo[1,5-a]pyridin-3-yl)carbonyl]-2-({[2-(4-fluorophenoxy)ethyl]carbamoyl}amino)benzoate 4.75 g (16 mmol) of triphosgene are added, at ambient temperature and under an inert atmosphere, to 4.99 g (13.3 mmol) of methyl 2-amino-5-({1-[3-(methoxycarbonyl)phenyl]imidazo[1,5-a]pyridin-3-yl}carbonyl)benzoate in 220 ml of dioxane. After heating for 5 hours at reflux, 6.21 g (40 mmol) of 2-(4-fluorophenoxy)-1-ethylamine and 4.05 g (40 mmol) of triethylamine are added at ambient temperature. The reaction medium is heated for 3 hours at reflux and then concentrated under reduced pressure. The residue is triturated from water. After filtration, the solid is rinsed with methanol and then dried under reduced pressure at 40° C. overnight. 6.67 g of a yellow solid are obtained.

MH+: 555

6-[(1-Bromoimidazo[1,5-a]pyridin-3-yl)carbonyl]-3-[2-(4-fluorophenoxy)ethyl]quinazoline-2,4(1H,3H)-dione 60.1 ml (60.1 mmol) of an aqueous 1N sodium hydroxide solution are added to 6.67 g (12 mmol) of methyl 5-[(1-bromoimidazo[1,5-a]pyridin-3-yl)carbonyl]-2-({[2-(4-fluorophenoxy)ethyl]carbamoyl}amino)benzoate dissolved in 600 ml of methanol. After heating at reflux for 2 hours, the reaction medium is acidified with 120 ml of an aqueous 1N hydrochloric acid solution and then diluted with 2000 ml of water. The precipitate obtained is filtered off, and dried under reduced pressure at 40° C. overnight. 5.83 g of a yellow solid are obtained.

MH+: 523.2, 525.2

6-[(1-Bromoimidazo[1,5-a]pyridin-3-yl)carbonyl]-3-[2-(4-fluorophenoxy)ethyl]-1-propylquinazoline-2,4(1H,3H)-dione 722 g (22.16 mmol) of caesium carbonate and 5.65 g (33.24 mmol) of propyl iodide are added, under an inert atmosphere, to 5.6 g (11.08 mmol) of 6-[(1-bromoimidazo[1,5-a]pyridin-3-yl)carbonyl]-3-[2-(4-fluorophenoxy)ethyl]quinazoline-2,4(1H,3H)-dione in 300 ml of DMF. The reaction medium is stirred for 12 hours at ambient temperature under a nitrogen atmosphere and then concentrated under reduced pressure. The residue obtained is washed with 700 ml of water and then dried under reduced pressure at 40° C. overnight. 5.74 g of a yellow solid are obtained.

MH+: 565, 567

Methyl 3-[3-({3-[2-(4-fluorophenoxy)ethyl]-1-propyl-2,4-dioxo-1,2,3,4-tetrahydroquinazolin-6-yl}carbonyl)imidazo[1,5-a]pyridin-1-yl]benzoate 2.178 g (12.1 mmol) of 3-methoxycarbonylphenylboronic acid, 4.279 g (20.16 mmol) of potassium phosphate dissolved in 30 ml of water, and 582.4 g (0.504 mmol) of tetrakis(triphenylphosphine)palladium are added to 5.7 g (10.08 mmol) of 6-[(1-bromoimidazo[1,5-a]pyridin-3-yl)carbonyl]-3-[2-(4-fluorophenoxy)ethyl]-1-propylquinazoline-2,4(1H,3H)-dione in 180 ml of NMP. The reaction medium is microwave-heated for 15 minutes at 120° C. and then concentrated under reduced pressure. The solid obtained is purified by silica gel column chromatography, elution being carried out with a dichloromethane/methanol (100/1) mixture. 4.32 g of a yellow solid are obtained.

MH+: 621.3

Sodium salt of 3-[3-({3-[2-(4-fluorophenoxy)ethyl]-1-propyl-2,4-dioxo-1,2,3,4-tetrahydroquinazolin-6-yl}carbonyl)imidazo[1,5-a]pyridin-1-yl]benzoic acid 69.6 ml (69.6 mmol) of an aqueous 1N lithium hydroxide solution are added to 4.32 g (6.96 mmol) of methyl 3-[3-({3-[2-(4-fluorophenoxy)ethyl]-1-propyl-2,4-dioxo-1,2,3,4-tetrahydroquinazolin-6-yl}carbonyl)imidazo[1,5-a]pyridin-1-yl]benzoate in 500 ml of THF. The reaction medium is heated for 3 hours at reflux and then acidified at ambient temperature with 150 ml of an aqueous 1N hydrochloric acid solution and, finally, diluted with 700 ml of water. After filtration, the residue obtained is dried under reduced pressure at 40° C. overnight.

5.88 ml (5.88 mmol) of an aqueous 1N sodium hydroxide solution are added to 4.11 g (6 mmol) of the yellow solid obtained, in 100 ml of methanol. After filtration, the residue obtained is dried under reduced pressure at 40° C. 3.46 g of a yellow solid are obtained.

MH+: 607.3

M.p.: 190-205° C. (decomposition)

$^1$H-NMR (D6-DMSO, 500 MHz): 0.98 (t, J=7.7 Hz, 3H), 1.71 (tq, J1=J2=7.7 Hz, 2H), 4.17 (t, J=7.7 Hz, 2H), 4.24 (t, J=6.6 Hz, 2H), 4.39 (t, J=6.6 Hz, 2H), 6.97-7.00 (2m, 2H), 7.10-7.16 (2m, 2H), 7.38-7.41 (m, 1H), 7.47-7.52 (m, 1H), 7.57-7.61 (m, 1H), 7.75-7.79 (m, 1H), 7.94-7.98 (2m, 2H), 8.26-8.30 (m, 1H), 8.49-8.52 (m, 1H), 8.97-9.02 (m, 1H), 9.26-9.28 (m, 1H), 9.89-9.93 (m, 1H)

The table which follows illustrates the chemical structures and the physical properties of some compounds according to the invention. In this table:

Me and Et represent respectively methyl and ethyl groups;
the wavy lines indicate the bond attached to the rest of the molecule;
"M.p." represents the melting point of the compound, expressed in degrees Celsius;
"M+H$^+$" represents the mass of the compound, obtained by LC-MS (Liquid Chromatography-Mass Spectroscopy).

TABLE NO 1
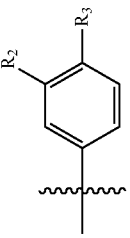
(I)
| No. | R₁ | R₃ R₂ [substituent] | R₄ | Salt | M.p. (°C.) | M + H⁺ |
|---|---|---|---|---|---|---|
| 1 Ex 1 | H | 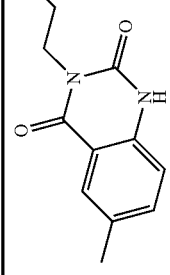 | H | / | 304 | 349 |
| 2 | H | 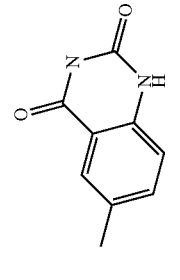 | H | / | 341 | 307 |
| 3 Ex 15 | H | 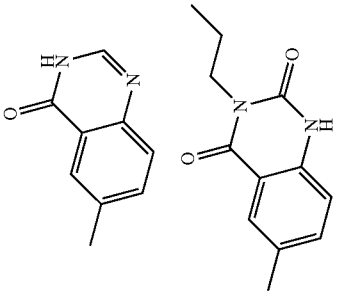 | H | / | 289 | 291 |
| 4 | H |  | 7-COOH | / | 380 | 393 |

TABLE NO 1-continued
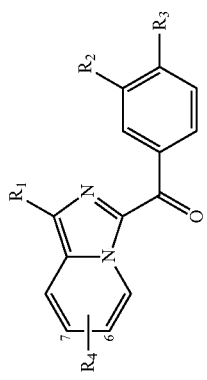
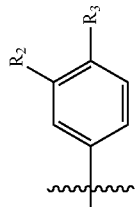
| No. | R₁ | | R₄ | Salt | M.p. (° C.) | M + H⁺ |
|---|---|---|---|---|---|---|
| 5 | H | (3-methyl-2,4-dioxo-quinazolinyl) | 7-COOH | / | 404 | 365 |
| 7 | —CO—NH₂ | (3-propyl-2,4-dioxo-quinazolinyl) | H | / | / | 392 |
| 8 Ex 3 | H | (3-propyl-2,4-dioxo-quinazolinyl) | 6-COOH | / | 384 | 393 |
| 9 | H | (3-propyl-2,4-dioxo-quinazolinyl) | 6-NHCOCH₂-piperidinyl | HCl | 234 | 503 |

TABLE NO 1-continued (I)

| No. | R₁ | [core structure] | R₄ | Salt | M.p. (°C.) | M + H⁺ |
|---|---|---|---|---|---|---|
| 10 Ex 2 | 3-methylbenzoate (C(=O)O⁻ on m-tolyl) | 3-propyl-6-methyl-quinazoline-2,4-dione | H | Na | 383 | 469 |
| 11 | H | 3-(carboxymethyl)-6-methyl-quinazoline-2,4-dione (CH₂CO₂⁻) | H | Na | 398 | 365 |
| 12 | H | 3-propyl-6-methyl-quinazoline-2,4-dione | —NH-C(=O)-CH₂-CH₂-OH | / | 278 | 436 |
| 13 Ex 8 | —NH—SO₂Me | 3-propyl-6-methyl-quinazoline-2,4-dione | H | / | 334 | 442 |

TABLE NO 1-continued

| No. | R₁ | | R₄ | Salt | M.p. (° C.) | M + H⁺ |
|---|---|---|---|---|---|---|
| 14 | 3-methylbenzoate | N-methyl-6-methylquinazoline-2,4-dione | H | Na | >41 | 441 |
| 15 | 4-methylbenzoate | N-propyl-6-methylquinazoline-2,4-dione | H | Na | >410 | 469 |
| 16 | ethyl 3-methylbenzoate | N-isopropyl-6-methylquinazoline-2,4-dione | H | — | 257 | 497 |

TABLE NO 1-continued

| No. | R₁ | | R₄ | Salt | M.p. (° C.) | M + H⁺ |
|---|---|---|---|---|---|---|
| 17 | phenyl | methyl 2-(6-methyl-2,4-dioxoquinazolin-3(4H)-yl)acetate | H | / | 361 | 455 |
| 18 | phenyl | 2-(6-methyl-2,4-dioxoquinazolin-3(4H)-yl)acetate | H | Na | 345 | 440 |
| 19 | 3-methylbenzoate | 3-benzyl-6-methylquinazoline-2,4(1H,3H)-dione | H | Na | 340 | 517 |
| 20 | 3-methylbenzoate | 3-isopropyl-6-methylquinazoline-2,4(1H,3H)-dione | H | Na | 363 | 469 |

TABLE NO 1-continued

| No. | R₁ | | R₂ R₃ | R₄ | Salt | M.p. (° C.) | M + H⁺ |
|---|---|---|---|---|---|---|---|
| 21 | 2-F, 5-methyl benzoate | | N-propyl quinazoline-2,4-dione, 6-methyl | H | Na | 318 | 487 |
| 22 | 3-F, 5-methyl benzoate | | N-propyl quinazoline-2,4-dione, 6-methyl | H | Na | 390 | 487 |
| 23 | H | | N-(methoxycarbonylmethyl) quinazoline-2,4-dione, 6-methyl | H | / | 308 | 379 |

TABLE NO 1-continued (I)

| No. | R₁ | | R₄ | Salt | M.p. (° C.) | M + H⁺ |
|---|---|---|---|---|---|---|
| 24 | methyl 3-benzoate | 4-oxo-3H-quinazolin-2-yl (6-methyl) | H | / | 318 | 425 |
| 26 | H | ethyl 2-(6-methyl-4-oxo-3H-quinazolin-2-yl)acetate | H | / | 263 | 377 |
| 28 | methyl 3-benzoate | 3-propyl-6-methyl-quinazoline-2,4-dione | H | / | 271 | 483 |

TABLE NO 1-continued

| No. | R₁ | (I) structure | R₄ | Salt | M.p. (° C.) | M + H⁺ |
|---|---|---|---|---|---|---|
| 29 Ex 5 | 3-methylbenzamide (C(=O)NH₂) | N-propyl quinazoline-2,4-dione with 6-methyl | H | / | 345-346 | 468 |
| 30 | 3-methylbenzoic acid (C(=O)OH) | N-(3,3,3-trifluoropropyl) quinazoline-2,4-dione with 6-methyl | H | / | 371 | 523 |
| 31 | 3-methylbenzoate (C(=O)O⁻) | N-(4-fluorobenzyl) quinazoline-2,4-dione with 6-methyl | H | Na | 317 | 535 |

TABLE NO 1-continued
| No. | R₁ | | R₂ R₃ | R₄ | Salt | M.p. (° C.) | M + H⁺ |
|---|---|---|---|---|---|---|---|
| 32 |  | | 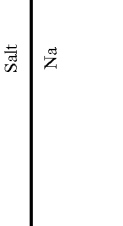 | H | Na | 316 | 553 |
| 33 | 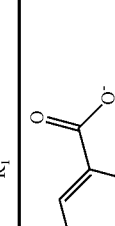 | |  | H | Na | 325 | 551 |
| 34 Ex 6 |  | | 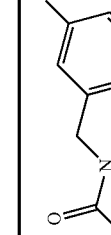 | H | / | / | 507 |

TABLE NO 1-continued

| No. | R1 | R2-R3 aryl group | R4 | Salt | M.p. (°C.) | M + H+ |
|---|---|---|---|---|---|---|
| 35 | 3-cyanophenyl | N-propyl-6-methyl-quinazoline-2,4-dione | H | / | 294-296 | 450 |
| 36 Ex 7 | 3-methyl-1,2,4-oxadiazol-5-yl phenyl | N-propyl-6-methyl-quinazoline-2,4-dione | H | / | 276-277 | 507 |
| 37 | 3-(methylsulfonylaminocarbonyl)phenyl | N-propyl-6-methyl-quinazoline-2,4-dione | H | / | 250-260 | 546 |

TABLE NO 1-continued

| No. | R1 | | R4 | Salt | M.p. (°C.) | M + H+ |
|---|---|---|---|---|---|---|
| 38 | hydroxamic acid meta-substituted benzene | propyl-quinazolinedione with 6-methyl | H | / | 269 | 484 |
| 39 | 3-methylbenzoic acid | 2,2,2-trifluoroethyl quinazolinedione with 6-methyl | H | / | 387 | 509 |
| 40 | 3-methylbenzoic acid | propyl N-methyl quinazolinedione with 6-methyl | H | / | 184-185 | 483 |

TABLE NO 1-continued

| No. | R$_1$ | R$_2$, R$_3$ (aryl) | (central structure) | R$_4$ | Salt | M.p. (°C.) | M + H$^+$ |
|---|---|---|---|---|---|---|---|
| 41 | 3-(N-methoxycarbamoyl)phenyl | 4-methylphenyl | N-propyl quinazoline-2,4-dione (6-methyl) | H | / | 255 | 498 |
| 42 | 3-carbamoylphenyl | 4-methylphenyl | N-benzyl quinazoline-2,4-dione (6-methyl) | H | / | 341 | 516 |
| 43 | 3-carboxyphenyl | 4-methylphenyl | N-propyl, N'-methoxymethyl quinazoline-2,4-dione (6-methyl) | H | / | 268 | 513 |

TABLE NO 1-continued

| No. | R1 | R3/R2 substituent | R4 | Salt | M.p. (°C.) | M + H+ |
|---|---|---|---|---|---|---|
| 44 | 3-methylbenzamide | 3,5-difluorobenzyl quinazoline-2,4-dione (6-methyl) | H | / | 340 | 552 |
| 45 | 3-methylbenzamide | 4-fluorobenzyl quinazoline-2,4-dione (6-methyl) | H | / | 319 | 534 |
| 46 | H | 3-propyl-2-phenyl-quinazolin-4-one (6-methyl) | H | / | / | 409 |
| 47 | 3-methylbenzonitrile | 3-propyl-1-methyl-quinazoline-2,4-dione (6-methyl) | H | / | 230 | 464 |

TABLE NO 1-continued

| No. | R1 | R2, R3 group | R4 | Salt | M.p. (° C.) | M + H+ |
|---|---|---|---|---|---|---|
| 48 | 3-methylbenzamide (C(O)NH2) | 3-methyl-quinazoline-2,4-dione | H | / | 274 | 440 |
| 49 Ex 4 | 3-methylbenzoic acid (C(O)OH) | 1-(4-fluorobenzyl)-3-methyl-quinazoline-2,4-dione | H | Na | 182 | 549 |
| 50 | 3-methylbenzoic acid (C(O)OH) | 1-(3,5-difluorobenzyl)-3-methyl-quinazoline-2,4-dione | H | / | 300-301 | 567 |

TABLE NO 1-continued (I)

| No. | R₁ | R₂ R₃ | R₄ | Salt | M.p. (° C.) | M + H⁺ |
|---|---|---|---|---|---|---|
| 51 | 3-methylbenzamide | N-(3,5-difluorobenzyl)-N'-methyl-7-methylquinazoline-2,4-dione | H | / | 290 | 566 |
| 52 | 3-methylbenzamide | N-(4-fluorobenzyl)-N'-methyl-7-methylquinazoline-2,4-dione | H | / | 305 | 548 |
| 53 Ex 13 | 3-methylbenzoic acid | 2-methyl-3-propyl-6-methylquinazolin-4(3H)-one | H | / | 305 | 467 |

TABLE NO 1-continued

| No. | R₁ | | R₄ | Salt | M.p. (° C.) | M + H⁺ |
|---|---|---|---|---|---|---|
| 54 | 3-methylbenzamide | N-methyl-6-methyl-3-propylquinazoline-2,4-dione | H | / | 265 | 482 |
| 55 Ex 14 | 3-methylbenzamide | 2,6-dimethyl-3-propylquinazolin-4-one | H | / | 238 | 466 |
| 56 | 3-methylbenzoic acid | 6-methyl-3-propylquinazolin-4-one | H | / | 311-312 | 453 |
| 57 | 3-methylbenzamide | 6-methyl-3-propylquinazolin-4-one | H | / | 251 | 452 |

TABLE NO 1-continued

| No. | R₁ | | R₄ | Salt | M.p. (° C.) | M + H⁺ |
|---|---|---|---|---|---|---|
| 58 | 3-methylbenzamide | 3-(4-chlorobenzyl)-7-methylquinazoline-2,4(1H,3H)-dione | H | / | 338 | 550 |
| 59 | 5-(3-methylphenyl)-3-methyl-1,2,4-oxadiazole | 1-methyl-3-propyl-6-methylquinazoline-2,4(1H,3H)-dione | H | / | 241 | 521 |
| 60 | 3-methylbenzoic acid | 3-benzyl-1-methyl-6-methylquinazoline-2,4(1H,3H)-dione | H | / | 295 | 531 |

TABLE NO 1-continued

| No. | R₁ | R₂/R₃ structure | R₄ | Salt | M.p. (° C.) | M + H⁺ |
|---|---|---|---|---|---|---|
| 61 | 2-methyl-1,3,4-oxadiazol-5-yl phenyl | 1-propyl-3-methyl-7-methyl-quinazoline-2,4-dione | H | / | 255 | 521 |
| 62 | 3-methylbenzamide | 1-benzyl-3-methyl-7-methyl-quinazoline-2,4-dione | H | / | 298 | 530 |
| 63 | 3-methylbenzoic acid | 1-propyl-3-propyl-7-methyl-quinazoline-2,4-dione | H | / | 250 | 511 |

TABLE NO 1-continued

| No. | R₁ | | R₄ | Salt | M.p. (° C.) | M + H⁺ |
|---|---|---|---|---|---|---|
| 64 | 3-cyanophenyl (methyl) | N-(3,5-difluorobenzyl)-N'-methyl-6-methylquinazoline-2,4-dione | H | / | 285 | 548 |
| 65 | 3-carbamoylphenyl (methyl) | N,N'-dipropyl-6-methylquinazoline-2,4-dione | H | / | 231 | 510 |
| 66 | 3-carboxyphenyl (methyl) | N-propyl-N'-(cyclopropylmethyl)-6-methylquinazoline-2,4-dione | H | / | 271 | 523 |

TABLE NO 1-continued

| No. | R₁ | R₂, R₃ structure | R₄ | Salt | M.p. (° C.) | M + H⁺ |
|---|---|---|---|---|---|---|
| 67 | 3-methyl benzamide | propyl/methyl quinazolinedione with cyclopropylmethyl | H | / | 254 | 522 |
| 68 | 3-methyl benzamide | 4-chlorobenzyl/methyl quinazolinedione | H | / | 310 | 564 |
| 69 | 3-methyl-1,2,4-oxadiazol-5-yl phenyl | 3,5-difluorobenzyl quinazolinedione | H | / | 319 | 591 |

TABLE NO 1-continued

| No. | R1 | R2, R3 substituent | R4 | Salt | M.p. (°C.) | M + H+ |
|---|---|---|---|---|---|---|
| 70 | 3-methylbenzoate | quinazoline-2,4-dione with 4-chlorobenzyl and methyl, 6-methyl | H | Na | 255 | 564 |
| 71 | 3-methylbenzoate | quinazoline-2,4-dione with 4-fluorobenzyl and methoxymethyl, 6-methyl | H | Na | 284-286 | 579 |
| 72 Ex 11 | 3-methylbenzoate | quinazoline-2,4-dione with 4-fluorobenzyl and propyl, 6-methyl | H | Na | 239-245 | 577 |

TABLE NO 1-continued (I)

| No. | R$_1$ | R$_2$, R$_3$ structure | R$_4$ | Salt | M.p. (° C.) | M + H$^+$ |
|---|---|---|---|---|---|---|
| 73 | 3-methyl-1,2,4-oxadiazol-5-yl phenyl | N-(3,5-difluorobenzyl), N'-methyl, 6-methyl quinazolinedione | H | / | 258 | 605 |
| 74 | 3-methylbenzamide | N-(4-fluorobenzyl), N'-propyl, 6-methyl quinazolinedione | H | / | 250-252 | 576 |
| 75 | 3-methylbenzamide | N-(4-fluorobenzyl), N'-methoxymethyl, 6-methyl quinazolinedione | H | / | 297-298 | 578 |

TABLE NO 1-continued
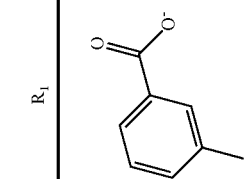
| No. | R1 | R2 R3 | R4 | Salt | M.p. (° C.) | M + H+ |
|---|---|---|---|---|---|---|
| 76 | 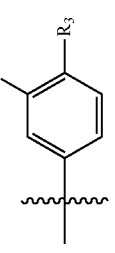 | 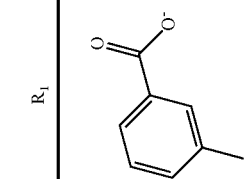 | H | / | 150-153 | 481 |
| 77 | 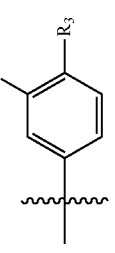 | 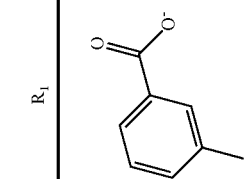 | H | / | 140-145 | 480 |
| 78 | 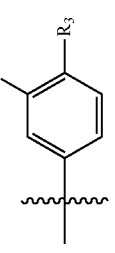 |  | H | / | 263 | 563 |

TABLE NO 1-continued (I)

| No. | R₁ | R₂, R₃ substituent | R₄ | Salt | M.p. (°C.) | M + H⁺ |
|---|---|---|---|---|---|---|
| 79 | ethyl 3-benzoate | N-(4-fluorobenzyl), N'-methyl, 5-methyl benzodiazinedione | H | / | 203-204 | 577 |
| 80 | 3-methylbenzamide | 3-propyl-2-isopropyl-6-methyl-quinazolin-4(3H)-one | H | / | 141-143 | 494 |
| 81 | 3-methylbenzoate | 3-propyl-2-isopropyl-6-methyl-quinazolin-4(3H)-one | H | Na | 226-230 | 494 |

TABLE NO 1-continued

| No. | R₁ | R₂/R₃ structure | R₄ | Salt | M.p. (°C.) | M + H⁺ |
|---|---|---|---|---|---|---|
| 82 Ex 9 | 2-(morpholin-4-yl)ethyl 3-methylbenzoate group | 1-(4-fluorobenzyl)-3-methyl-7-methyl-quinazoline-2,4-dione linkage | H | Na | 215 | 662 |
| 83 | 2-(dimethylamino)ethyl 3-methylbenzoate group | 1-(4-fluorobenzyl)-3-methyl-7-methyl-quinazoline-2,4-dione linkage | H | / | 238 | 620 |
| 84 | 3-methylbenzoate anion | 3-propyl-2-cyclopropyl-6-methyl-quinazolin-4(3H)-one linkage | H | Na | 235–238 | 493 |

TABLE NO 1-continued (I)

| No. | R₁ | R₂-R₃ substituent group | R₄ | Salt | M.p. (° C.) | M + H⁺ |
|---|---|---|---|---|---|---|
| 85 | 3-methylbenzoate anion | N-(4-fluorobenzyl), N'-ethyl, 6-methyl quinazolinedione | H | Na | 244-246 | 563 |
| 86 | 2-(pyrrolidin-1-yl)ethyl 3-methylbenzoate | N-(4-fluorobenzyl), N'-methyl, 6-methyl quinazolinedione | H | / | 210 | 646 |
| 87 | 2-hydroxyethyl 3-methylbenzoate | N-(4-fluorobenzyl), N'-methyl, 6-methyl quinazolinedione | H | / | 234 | 593 |

TABLE NO 1-continued

| No. | $R_1$ | | $R_4$ | Salt | M.p. (°C.) | M + H⁺ |
|---|---|---|---|---|---|---|
| 88 | 3-methyl-1,2,4-oxadiazol-5-yl phenyl | 4-fluorobenzyl methyl quinazolinedione (5-methyl) | H | / | 266-268 | 587 |
| 89 | 3-methylbenzoate | 3-fluorobenzyl methyl quinazolinedione (6-methyl) | H | Na | 275-278 | 549 |
| 90 | 2-propoxy-4-fluorophenyl | carboxymethyl quinazolinedione (6-methyl) | H | / | / | 517 |

TABLE NO 1-continued
| No. | R1 | | R4 | Salt | M.p. (° C.) | M + H+ |
|---|---|---|---|---|---|---|
| 91 |  | 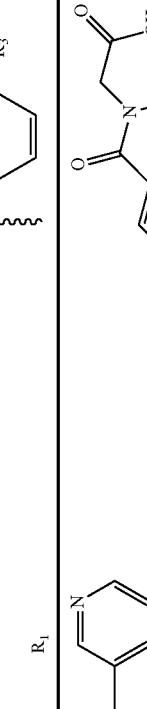 | H | / | / | 442 |
| 92 | 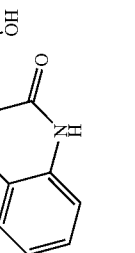 | 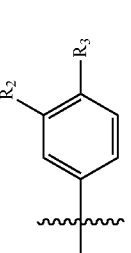 | H | / | / | 472 |
| 93 |  | 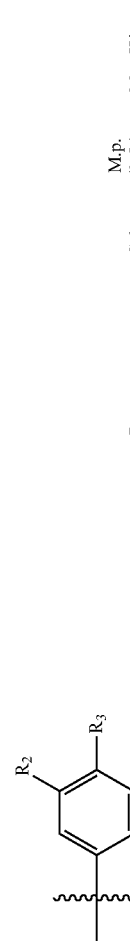 | H | HCl | / | 602 |

TABLE NO 1-continued

| No. | R₁ | | R₂ R₃ | R₄ | Salt | M.p. (° C.) | M + H⁺ |
|---|---|---|---|---|---|---|---|
| 94 | 3-methylbenzoic acid | | 3-(3-methylbutyl)-6-methylquinazoline-2,4-dione | H | / | / | 497 |
| 94a | 3-methylbenzoic acid | | 3-(pyridin-3-ylmethyl)-6-methylquinazoline-2,4-dione | H | HCl | / | 554 |
| 95 | 3-methylbenzoic acid | | 3-(2-piperidin-1-ylethyl)-6-methylquinazoline-2,4-dione | H | HCl | / | 575 |

TABLE NO 1-continued

| No. | R₁ | (structure) | R₄ | Salt | M.p. (° C.) | M + H⁺ |
|---|---|---|---|---|---|---|
| 96 | 3-methylbenzoic acid | N-ethylpyrrolidinylmethyl quinazolinedione (6-methyl) | H | HCl | / | 575 |
| 97 | 3-methylbenzoic acid | isohexyl quinazolinedione (6-methyl) | H | / | / | 511 |
| 98 | 3-methylbenzoic acid | 3-(pyridin-3-yl)propyl quinazolinedione (6-methyl) | H | HCl | / | 583 |

TABLE NO 1-continued
| No. | R₁ | | R₄ | Salt | M.p. (° C.) | M + H⁺ |
|---|---|---|---|---|---|---|
| 99 | 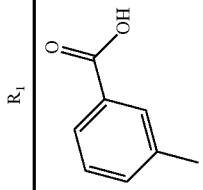 | 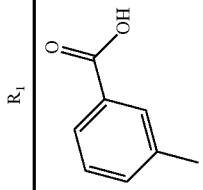 | H | / | / | 521 |
| 100 | 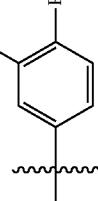 | 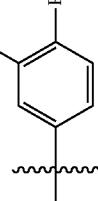 | H | / | / | 524 |
| 101 | 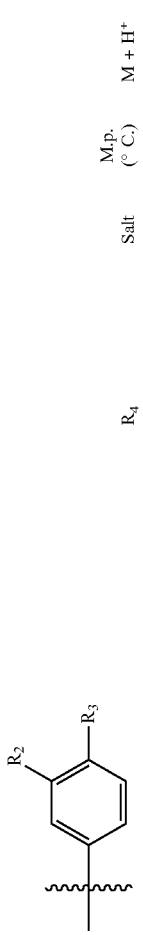 | 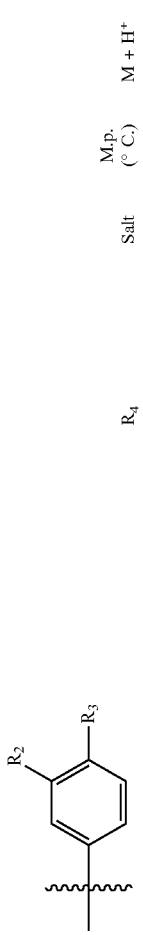 | H | / | / | 521 |

TABLE NO 1-continued

| No. | R$_1$ | | R$_4$ | Salt | M.p. (° C.) | M + H$^+$ |
|---|---|---|---|---|---|---|
| 102 | 3-methylbenzoic acid | pyrrolidine-ethyl quinazolinedione (6-methyl) | H | / | / | 538 |
| 103 | 3-methylbenzoic acid | 1-(pyridin-4-yl)ethyl quinazolinedione (6-methyl) | H | HCl | / | 568 |
| 104 | 3-methylbenzoic acid | (S)-1-(methylcarbamoyl)ethyl quinazolinedione (6-methyl) | H | / | / | 512 |

TABLE NO 1-continued

| No. | R₁ | R₂–R₃ substituent | R₄ | Salt | M.p. (°C.) | M + H⁺ |
|---|---|---|---|---|---|---|
| 105 | 3-methylbenzoic acid | 3-(2-cyclopentylethyl)-7-methyl-quinazoline-2,4-dione | H | / | / | 523 |
| 106 | 5-methylnicotinic acid | 3-(4-fluorobenzyl)-1-methyl-7-methyl-quinazoline-2,4-dione | H | HCl | / | 550 |
| 107 | N-methyl-3-methylbenzamide | 3-(4-fluorobenzyl)-1-methyl-7-methyl-quinazoline-2,4-dione | H | / | 318 | 562 |

TABLE NO 1-continued
| No. | R₁ | | R₂, R₃ | R₄ | Salt | M.p. (° C.) | M + H⁺ |
|---|---|---|---|---|---|---|---|
| 108 | 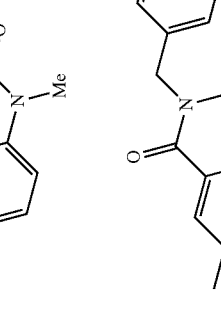 | | 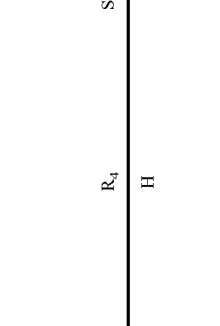 | H | / | / | 548 |
| 109 | 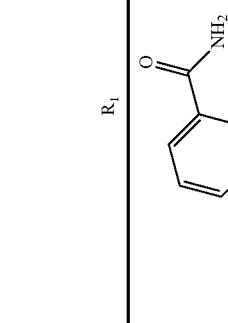 | | 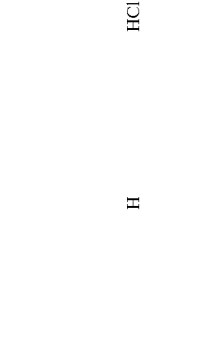 | H | HCl | 177 | 690 |
| 110 | 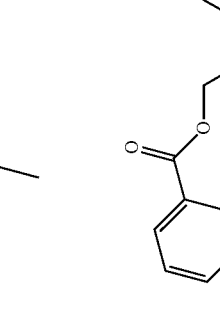 | | 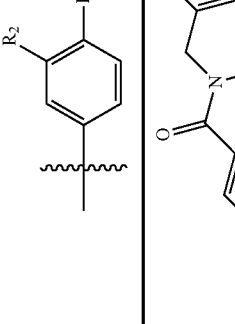 | H | HCl | 187 | 674 |

TABLE NO 1-continued
| No. | R₁ | | R₄ | Salt | M.p. (° C.) | M + H⁺ |
|---|---|---|---|---|---|---|
| 111 |  | 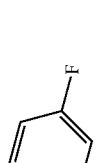 | H | / | 224 | 505 |
| 112 Ex 12 |  | 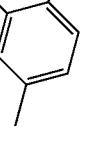 | H | HCl | 267 | 506 |
| 113 | 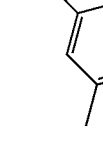 | 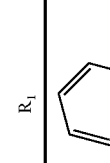 | H | / | 106 | 637 |

TABLE NO 1-continued

| No. | R₁ | R₂, R₃ | R₄ | Salt | M.p. (°C.) | M + H⁺ |
|---|---|---|---|---|---|---|
| 114 | 3-methyl-benzonitrile | 3-methyl-1-(4-fluorobenzyl)-quinazoline-2,4-dione | H | / | / | 530 |
| 115 | 3-methyl-N-(2-morpholinoethyl)benzamide | 3-methyl-1-(4-fluorobenzyl)-quinazoline-2,4-dione | H | HCl | 214 | 661 |
| 116 Ex 10 | 3-[N-(2-dimethylaminoethyl)carbamoyl]phenyl | 3-methyl-1-(4-fluorobenzyl)-quinazoline-2,4-dione | H | HCl | 247 | 619 |

TABLE NO 1-continued
| No. | R₁ | | R₄ | Salt | M.p. (° C.) | M + H⁺ |
|---|---|---|---|---|---|---|
| 117 | 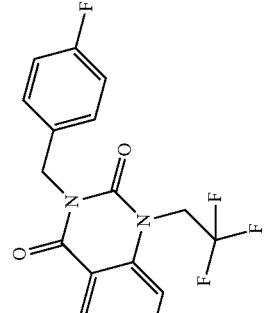 | 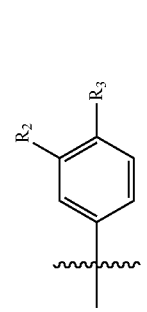 | H | Na | / | 598 |
| 118 | 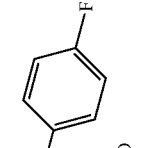 | 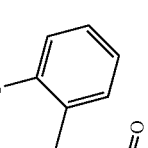 | H | Na | / | 617 |

TABLE NO 1-continued

| No. | R₁ | R₂ R₃ structure | R₄ | Salt | M.p. (° C.) | M + H⁺ |
|---|---|---|---|---|---|---|
| 119 | 3-methylbenzoic acid | N-(2-methoxyethyl), 4-fluorobenzyl, 6-methyl quinazoline-2,4-dione | H | Na | / | 593 |
| 120a | 3-methyl-N,N-dimethylbenzamide | N-Me, 4-fluorobenzyl, 6-methyl quinazoline-2,4-dione | H | / | 259 | 576 |
| 120 | 3-(3-(dimethylamino)propoxy)-methylphenyl | N-Me, 4-fluorobenzyl, 6-methyl quinazoline-2,4-dione | H | HCl | 247 | 606 |

TABLE NO 1-continued

| No. | R₁ | R₄ | Salt | M.p. (° C.) | M + H⁺ |
|---|---|---|---|---|---|
| 121 | 3-methylphenoxy-CH₂CH₂-NMe₂ | H | HCl | 287 | 592 |
| 122 | 3-methylphenoxy-CH₂CH₂-morpholine | H | HCl | 274 | 634 |
| 123 | 3-methyl-hydroxyphenyl | H | / | 216 | 521 |

TABLE NO 1-continued
| No. | R₁ | R₂ R₃ | R₄ | Salt | M.p. (°C.) | M + H⁺ |
|---|---|---|---|---|---|---|
| 124 | 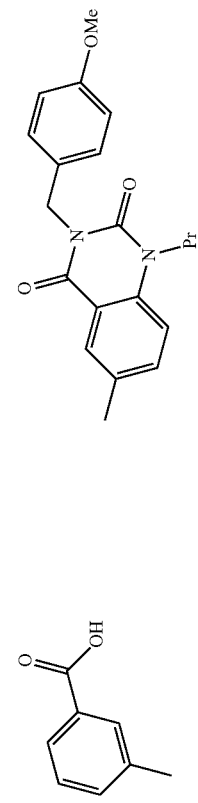 | 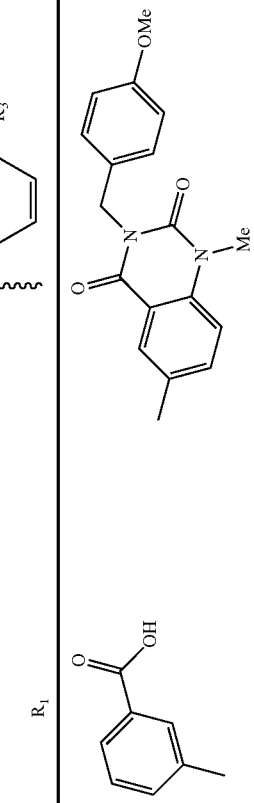 | H | Na | 258 | 561 |
| 125 | 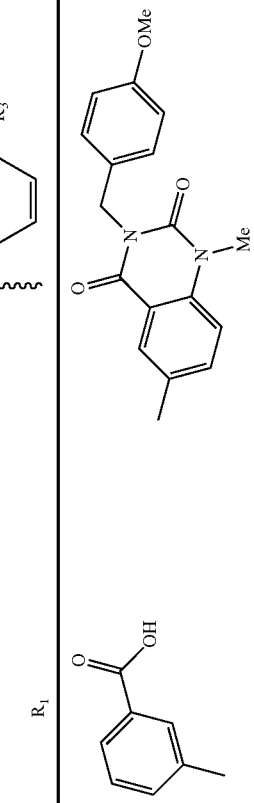 | 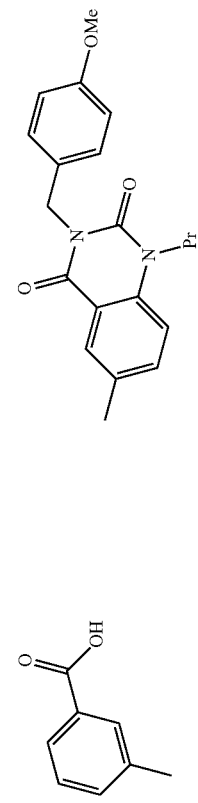 | H | Na | 240 | 589 |
| 126 | 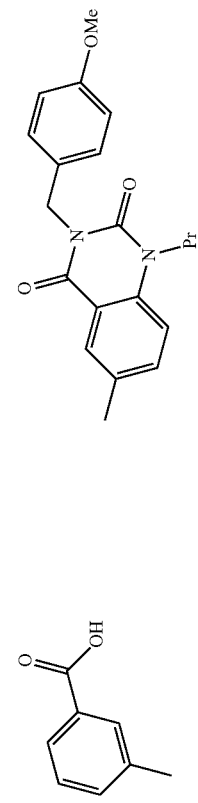 | 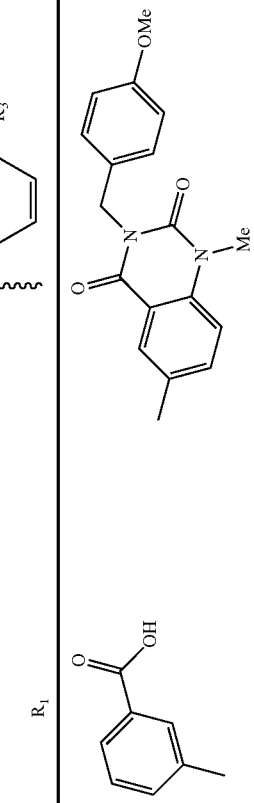 | H | HCl | 275 | 534 |

TABLE NO 1-continued
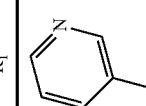
| No. | R₁ | | R₄ | Salt | M.p. (°C.) | M + H⁺ |
|---|---|---|---|---|---|---|
| 127 | *3-methylpyridine* | *4-fluorobenzyl quinazolinedione with Pr and methyl* | H | HCl | 273 | 534 |
| 128 | *3-methylpyridine N-oxide* | *4-fluorobenzyl quinazolinedione with Pr and methyl* | H | / | 223 | 550 |
| 129 | *3-methylbenzoic acid* | *4-methylbenzyl quinazolinedione with Pr and methyl* | H | Na | 246 | 573 |

TABLE NO 1-continued

| No. | R₁ | R₂ R₃ | R₄ | Salt | M.p. (° C.) | M + H⁺ |
|---|---|---|---|---|---|---|
| 130 | 3-carboxyphenyl | 4-fluorobenzyl-substituted quinazolinedione with Pr, 6-methyl | H | Na | 256 | 591 |
| 131 | pyridine N-oxide | 4-fluorobenzyl-substituted quinazolinedione with Pr, 6-methyl | H | HCl | 291 | 550 |

TABLE NO 1-continued

| No. | R₁ | R₂ R₃ | R₄ | Salt | M.p. (°C.) | M + H⁺ |
|---|---|---|---|---|---|---|
| 132 | 3-methylbenzoic acid | 4-fluorobenzyl-dihydroquinazolinedione with ethyl-pyrrolidine, 6-methyl | H | Na | / | 632 |
| 133 | 3-methylpyridine | 4-fluorobenzyl-dihydroquinazolinedione with pentafluoroethyl-ethyl, 6-methyl | H | / | / | 624 |

TABLE NO 1-continued
| No. | R₁ | (structure) | R₄ | Salt | M.p. (° C.) | M + H⁺ |
|---|---|---|---|---|---|---|
| 134 | 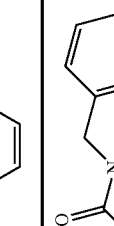 | 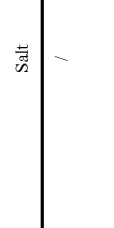 | H | / | / | 605 |
| 135 | 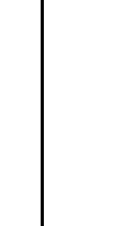 | 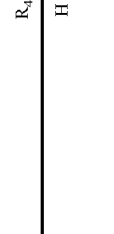 | H | Na | 236 | 627 |

TABLE NO 1-continued
| No. | R₁ | R₂ R₃ R₄ | Salt | M.p. (° C.) | M + H⁺ |
|---|---|---|---|---|---|
| 136 |  |  H | / | 112 | 681 |
| 137 |  |  H | Na | 237 | 599 |

TABLE NO 1-continued
| No. | R₁ | R₃ R₂ | R₄ | Salt | M.p. (° C.) | M + H⁺ |
|---|---|---|---|---|---|---|
| 138 | 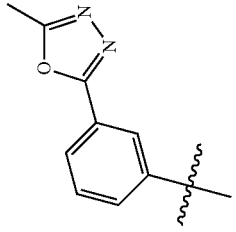 | 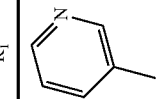 | H | HCl | 226 | 563 |
| 139 | 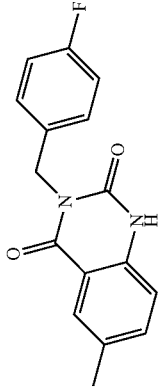 | 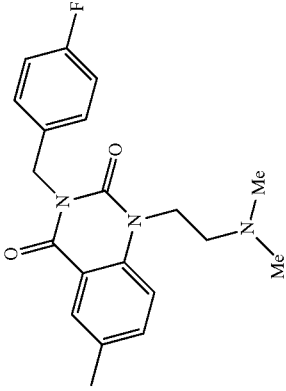 | H | / | / | 573 |

TABLE NO 1-continued

| No. | R₁ | (structure) | R₄ | Salt | M.p. (°C.) | M + H⁺ |
|---|---|---|---|---|---|---|
| 140 | 2-methyl-1,3,4-oxadiazol-5-yl phenyl | 3-(4-fluorobenzyl)-1-methyl-6-methyl-quinazoline-2,4-dione | H | / | / | 587 |
| 141 | 3-methylbenzoic acid | 3-(4-fluorobenzyl)-1-(2,2,3,3,3-pentafluoropropyl)-6-methyl-quinazoline-2,4-dione | H | Na | / | 667 |

TABLE NO 1-continued
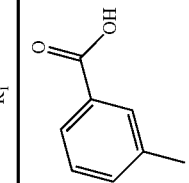
(I)
| No. | R₁ | | R₄ | Salt | M.p. (° C.) | M + H⁺ |
|---|---|---|---|---|---|---|
| 142 |  | 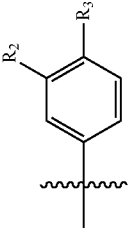 | H | Na | / | 646 |
| 143 | 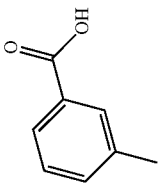 |  | H | Na | / | 648 |

TABLE NO 1-continued

| No. | R₁ | (structure) | R₄ | Salt | M.p. (°C.) | M + H⁺ |
|---|---|---|---|---|---|---|
| 144 | 3-methylpyridinyl | N-(4-fluorobenzyl), N'-(2-piperidinylethyl) methyl-benzo-diazinedione | H | / | / | 603 |
| 145 | 3-methylpyridinyl | N-propyl, N'-methyl methyl-quinazolinedione | H | HCl | 250 | 440 |
| 146 | 3-methylpyridinyl | N-propyl, N'-propyl methyl-quinazolinedione | H | HCl | 278 | 468 |

TABLE NO 1-continued

| No. | R₁ | | R₄ | Salt | M.p. (° C.) | M + H⁺ |
|---|---|---|---|---|---|---|
| 147 | 3-methylpyridine N-oxide | N-(4-fluorobenzyl), N'-Me, 6-methyl quinazoline-2,4-dione | H | — | 294 | 522 |
| 148 | 3-methylbenzoic acid | N-(4-fluorophenethyl), N'-Me, 6-methyl quinazoline-2,4-dione | H | Na | 256 | 563 |
| 149 | 3-methylpyridine | N-benzyl, N'-Pr, 6-methyl quinazoline-2,4-dione | H | HCl | 225 | 516 |

TABLE NO 1-continued

| No. | R₁ | R₂-R₃ substituent | R₄ | Salt | M.p. (°C.) | M + H⁺ |
|---|---|---|---|---|---|---|
| 150 | 3-methyl pyridine N-oxide | N-(4-fluorophenethyl)-N'-methyl-6-methylquinazoline-2,4-dione | H | / | 257 | 536 |
| 151 | 2-amino-5-methylpyridine | N-(4-fluorobenzyl)-N'-propyl-6-methylquinazoline-2,4-dione | H | / | 259 | 549 |
| 152 | 3-methyl pyridine N-oxide | N-benzyl-N'-propyl-6-methylquinazoline-2,4-dione | H | / | 128 | 532 |

TABLE NO 1-continued

| No. | R₁ | | R₄ | Salt | M.p. (° C.) | M + H⁺ |
|---|---|---|---|---|---|---|
| 153 | N-methylpyrazol-4-yl | 4-F-benzyl, N-Pr, 6-methyl quinazoline-2,4-dione | H | / | 233 | 537 |
| 154 | 2-OMe-5-methylpyridin-5-yl | 4-F-benzyl, N-Pr, 6-methyl quinazoline-2,4-dione | H | HCl | 128 | 564 |
| 155 | pyridine N-oxide-3-yl | N-benzyl, N-Me, 6-methyl quinazoline-2,4-dione | H | / | / | 504 |

TABLE NO 1-continued

| No. | R₁ | | R₄ | Salt | M.p. (° C.) | M + H⁺ |
|---|---|---|---|---|---|---|
| 156 | 5-methyl-2-aminopyridinyl | 3-(4-fluorobenzyl)-1-methyl-6-methylquinazoline-2,4-dione | H | / | 278 | 521 |
| 157 | Me | 3-(4-fluorobenzyl)-1-propyl-6-methylquinazoline-2,4-dione | H | / | / | 471 |
| 158 | 3-methylbenzoic acid | 3-(4-fluorophenethyl)-1-propyl-6-methylquinazoline-2,4-dione | H | Na | 221 | 591 |

TABLE NO 1-continued

| No. | R₁ | | R₄ | Salt | M.p. (° C.) | M + H⁺ |
|---|---|---|---|---|---|---|
| 159 | 3-methylpyridin-yl | N-propyl, N'-(4-fluorophenethyl), 6-methyl quinazoline-2,4-dione | H | HCl | 525 | 548 |
| 160 | 3-methylpyridine N-oxide | N-propyl, N'-(4-fluorophenethyl), 6-methyl quinazoline-2,4-dione | H | / | 250 | 564 |
| 161 | 2-methoxy-5-methylpyridinyl | N-methyl, N'-(4-fluorobenzyl), 6-methyl quinazoline-2,4-dione | H | HCl | 230 | 536 |

TABLE NO 1-continued

| No. | R₁ | R₂ R₃ | R₄ | Salt | M.p. (°C.) | M + H⁺ |
|---|---|---|---|---|---|---|
| 162 | 1-methyl-pyrazol-4-yl | 3-(1-(4-fluorobenzyl)-3-methyl-6-methyl-2,4-dioxo-1,2,3,4-tetrahydroquinazolin) | H | / | 194 | 509 |
| 163 | 4-(4-methylpyridin-2-yl)piperazin-1-yl | 3-(1-(4-fluorobenzyl)-3-propyl-6-methyl-2,4-dioxo-1,2,3,4-tetrahydroquinazolin) | H | / | 160 | 618 |

TABLE NO 1-continued

| No. | R₁ | | R₄ | Salt | M.p. (° C.) | M + H⁺ |
|---|---|---|---|---|---|---|
| 164 | 3-methylpyridine | 4-(2-morpholinoethoxy)benzyl-6-methylquinazoline-2,4-dione N-Me | H | / | / | 617 |
| 165 | 3-methylpyridine | 3-isopentyl-6-methyl-1-methylquinazoline-2,4-dione | H | / | / | 482 |
| 166 | 3-methylpyridine | 4-(2-(pyrrolidin-1-yl)ethoxy)benzyl-6-methylquinazoline-2,4-dione | H | / | / | 587 |

TABLE NO 1-continued
| No. | R₁ | R₄ | Salt | M.p. (° C.) | M + H⁺ |
|---|---|---|---|---|---|
| 167 | 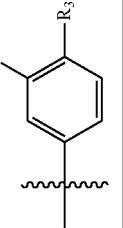 | 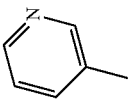 | H | / | 506 |
| 168 | 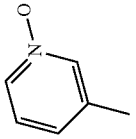 | 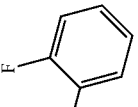 | H | / | 522 |

TABLE NO 1-continued

| No. | R₁ | | R₄ | Salt | M.p. (° C.) | M + H⁺ |
|---|---|---|---|---|---|---|
| 169 | 3-methylbenzoic acid group | 4-(2-pyrrolidin-1-yl-ethoxy)benzyl-methylquinazolinedione | H | / | / | 630 |
| 170 | Me | 4-fluorobenzyl-N-Me methylquinazolinedione | H | / | / | 443 |
| 171 | 3-methylbenzoic acid group | isohexyl-N-Me methylquinazolinedione | H | Na | / | 525 |

TABLE NO 1-continued
| No. | R₁ | R₂, R₃ | R₄ | Salt | M.p. (° C.) | M + H⁺ |
|---|---|---|---|---|---|---|
| 172 | 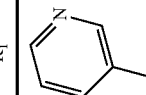 | 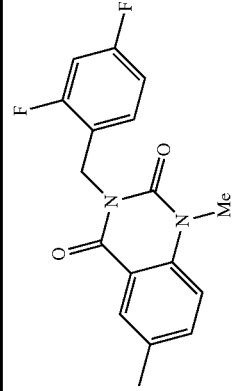 | H | / | / | 524 |
| 173 | 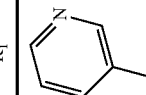 | 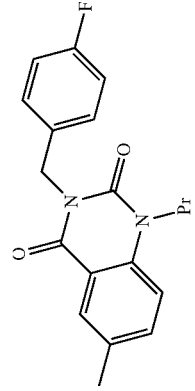 | H | / | 261 | 590 |
| 174 | 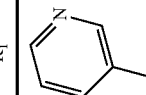 | 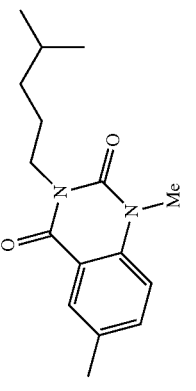 | H | / | / | 498 |

TABLE NO 1-continued

| No. | R₁ | (structure) | R₄ | Salt | M.p. (°C.) | M + H⁺ |
|---|---|---|---|---|---|---|
| 175 | 3-pyridyl | N-(3,5-difluorobenzyl)-N'-methyl-6-methylquinazoline-2,4-dione | H | / | / | 524 |
| 176 | 3-methylbenzoic acid | N-[4-(2-dimethylaminoethoxy)benzyl]-6-methylquinazoline-2,4-dione | H | Na | / | 604 |
| 177 | 2-methyl-3-benzoic acid | N-(4-fluorobenzyl)-N'-propyl-6-methylquinazoline-2,4-dione | H | Na | 236 | 591 |

TABLE NO 1-continued
| No. | R₁ | | R₄ | Salt | M.p. (°C.) | M + H⁺ |
|---|---|---|---|---|---|---|
| 178 | 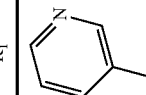 | 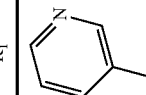 | H | HCl | 229 | 530 |
| 179 | 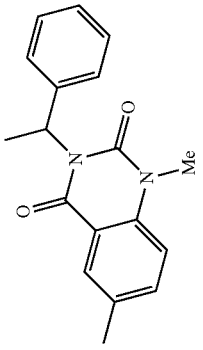 | 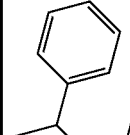 | H | Na | 270 | 563 |
| 180 | 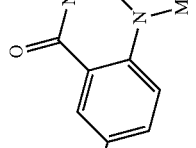 | 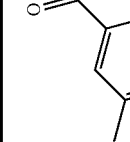 | H | HCl | 261 | 502 |

TABLE NO 1-continued

| No. | R₁ | | R₄ | Salt | M.p. (° C.) | M + H⁺ |
|---|---|---|---|---|---|---|
| 181 | 3-methylpyridin-yl | 3-fluorobenzyl quinazoline-2,4-dione N-Me, 6-methyl | H | / | / | 506 |
| 182 | 3-methylpyridin-yl | 2,4-difluorobenzyl quinazoline-2,4-dione N-Me, 6-methyl | H | / | / | 524 |

TABLE NO 1-continued

| No. | R₁ | (structure) | R₄ | Salt | M.p. (°C.) | M + H⁺ |
|---|---|---|---|---|---|---|
| 183 | (piperazinyl-pyridyl) | (4-fluorobenzyl/methyl tolyl quinazolinedione) | H | / | 261 | 590 |
| 184 | (3-pyridyl) | (1-phenylethyl/methyl tolyl quinazolinedione) | H | HCl | 261 | 502 |

TABLE NO 1-continued

| No. | R₁ | | R₄ | Salt | M.p. (° C.) | M + H⁺ |
|---|---|---|---|---|---|---|
| 185 | 3-methylbenzoic acid | N-(1-phenylethyl), N'-Pr, 6-methyl quinazoline-2,4-dione | H | Na | 238 | 573 |
| 186 | 3-methylbenzoic acid | N-(1-phenylethyl), N'-Me, 6-methyl quinazoline-2,4-dione | H | Na | 274 | 545 |
| 187 | 3-methylpyridine N-oxide | N-(4-methylpentyl), N'-Me, 6-methyl quinazoline-2,4-dione | H | / | / | 498 |

TABLE NO 1-continued

| No. | R₁ | (structure) | R₄ | Salt | M.p. (° C.) | M + H⁺ |
|---|---|---|---|---|---|---|
| 188 | 3-pyridyl-methyl | N-(3,5-difluorobenzyl), N'-Me, 6-methyl quinazoline-2,4-dione | H | / | / | 524 |
| 189 | 3-(carboxy)benzyl | N-[4-(2-dimethylaminoethoxy)benzyl] quinazoline-2,4-dione | H | Na | / | 604 |
| 190 | 2-methyl-3-(carboxy)phenyl | N-(4-fluorobenzyl), N'-Pr, 6-methyl quinazoline-2,4-dione | H | Na | 236 | 591 |

TABLE NO 1-continued
| No. | R₁ | (structure) | R₄ | Salt | M.p. (°C.) | M + H⁺ |
|---|---|---|---|---|---|---|
| 191 | 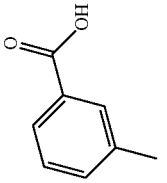 | 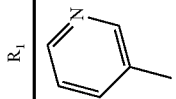 | H | HCl | 229 | 530 |
| 192 | 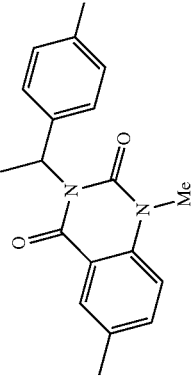 | 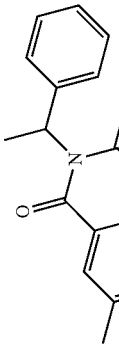 | H | HCl | 198 | 520 |
| 193 | 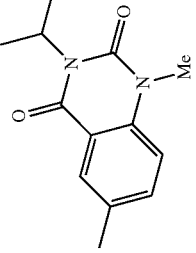 | 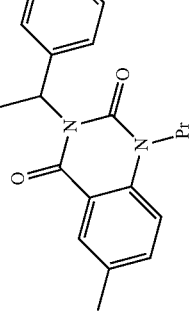 | H | Na | 270 | 563 |

TABLE NO 1-continued
| No. | R₁ | R₂, R₃ | R₄ | Salt | M.p. (°C.) | M + H⁺ |
|---|---|---|---|---|---|---|
| 194 | 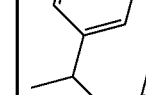 | 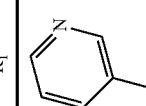 | H | HCl | 218 | 548 |
| 195 | 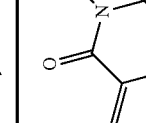 | 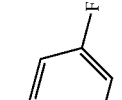 | H | Na | 233 | 591 |
| 196 |  | 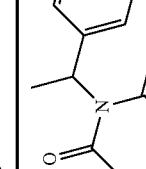 | H | Na | / | 587 |

TABLE NO 1-continued

| No. | R₁ | R₂ R₃ (substituent) | R₄ | Salt | M.p. (°C.) | M + H⁺ |
|---|---|---|---|---|---|---|
| 197 | 3-methylbenzoic acid | 3-(4-methylbenzyl)-7-methyl-quinazoline-2,4-dione with N-Me | H | Na | 257 | 545 |
| 198 | 3-methylbenzoic acid | 3-[1-(4-fluorophenyl)cyclopropyl]-7-methyl-quinazoline-2,4-dione with N-Pr | H | Na | 285 | 575 |
| 199 | 3-pyridyl | 3-[1-(4-fluorophenyl)cyclopropyl]-7-methyl-quinazoline-2,4-dione with N-Pr | H | HCl | 264 | 560 |

TABLE NO 1-continued

| No. | R₁ | | R₂, R₃ structure | R₄ | Salt | M.p. (°C.) | M + H⁺ |
|---|---|---|---|---|---|---|---|
| 200 | 3-methylbenzoic acid | | 4-fluorophenyl cyclopropyl quinazolinedione-Pr | H | Na | 258 | 603 |
| 201 | 1,5-dimethylpyrazole | | 4-fluorobenzyl methylquinazolinedione | H | / | / | 509 |
| 202 | 3-methylpyridine | | cyclopentylethyl methylquinazolinedione | H | / | / | 494 |

TABLE NO 1-continued
| No. | R₁ | | R₄ | Salt | M.p. (° C.) | M + H⁺ |
|---|---|---|---|---|---|---|
| 203 | 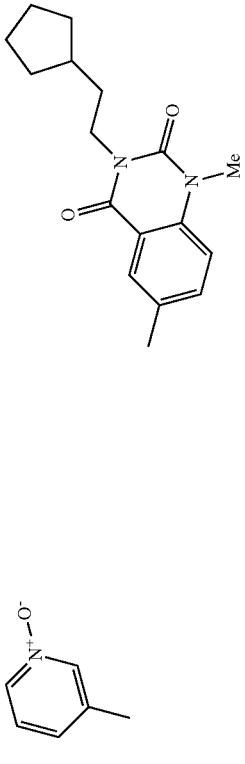 | 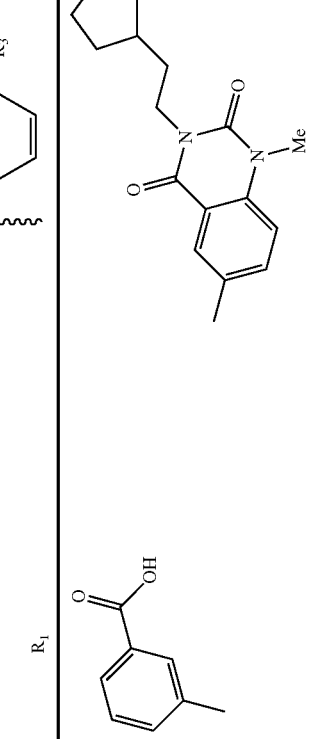 | H | Na | / | 537 |
| 204 | 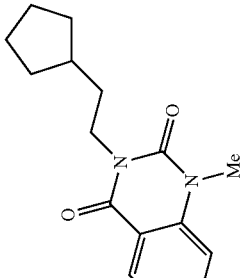 | 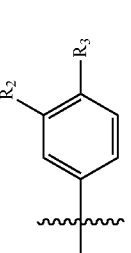 | H | / | / | 510 |

TABLE NO 1-continued

| No. | R₁ | R₂, R₃ structure | R₄ | Salt | M.p. (°C.) | M + H⁺ |
|---|---|---|---|---|---|---|
| 205 | 3-methylbenzoic acid | cyclopentylethyl-substituted quinazoline-2,4-dione with N-Pr and 6-methyl | H | Na | / | 565 |
| 206 | 3-methylpyridine | isohexyl-substituted quinazoline-2,4-dione with N-Pr and 6-methyl | H | / | / | 510 |
| 207 | 3-methylbenzoic acid | isohexyl-substituted quinazoline-2,4-dione with N-Pr and 6-methyl | H | Na | / | 553 |

TABLE NO 1-continued

| No. | R₁ | (structure) | R₄ | Salt | M.p. (° C.) | M + H⁺ |
|---|---|---|---|---|---|---|
| 208 | 4-methylpyridine | N-(4-fluorobenzyl), N'-Me quinazoline-2,4-dione with 6-methyl | H | HCl | 195 | 506 |
| 209 | 3-methylpyridine | N-(4-fluorobenzyl), N'-(3,3,3-trifluoropropyl) quinazoline-2,4-dione with 6-methyl | H | / | 240 | 588 |
| 210 | 3-methylpyridine | N-(thiophen-2-ylmethyl), N'-Me quinazoline-2,4-dione with 6-methyl | H | / | / | 494 |

TABLE NO 1-continued

| No. | R₁ | R₂/R₃ | R₄ | Salt | M.p. (°C.) | M + H⁺ |
|---|---|---|---|---|---|---|
| 211 | 3-methylbenzoic acid | thiophene-methyl quinazolinedione, N-Me, 6-methyl | H | Na | / | 537 |
| 212 | 3-methylpyridine | thiophene-methyl quinazolinedione, N-Pr, 6-methyl | H | / | / | 522 |
| 213 | 3-methylbenzoic acid | thiophene-methyl quinazolinedione, N-Pr, 6-methyl | H | Na | / | 565 |

TABLE NO 1-continued

| No. | R₁ | R₂, R₃ | R₄ | Salt | M.p. (° C.) | M + H⁺ |
|---|---|---|---|---|---|---|
| 214 | 3-pyridyl-CH₂- | 2-(4-fluorophenoxy)ethyl / N-Me quinazolinedione (6-methyl) | H | / | / | 536 |
| 215 | 3-pyridyl-CH₂- | 2-(4-fluorophenoxy)ethyl / N-Pr quinazolinedione (6-methyl) | H | / | / | 564 |
| 216 | 2-thienyl-CH₂- | 4-fluorobenzyl / N-Me quinazolinedione (6-methyl) | H | / | 243 | 511 |

TABLE NO 1-continued

| No. | R₁ | R₂, R₃ group | R₄ | Salt | M.p. (°C.) | M + H⁺ |
|---|---|---|---|---|---|---|
| 217 | 3-methoxyphenyl (m-OMe-C₆H₄) | N-(4-fluorobenzyl), N'-Me, 6-methyl quinazoline-2,4-dione | H | / | 255 | 535 |
| 218 | nBu | N-(4-fluorobenzyl), N'-Me, 6-methyl quinazoline-2,4-dione | H | / | / | 485 |
| 219 | 3-methylpyridine N-oxide | N-[2-(4-fluorophenoxy)ethyl], N'-Pr, 6-methyl quinazoline-2,4-dione | H | / | / | 580 |

TABLE NO 1-continued

| No. | R₁ | (structure) | R₄ | Salt | M.p. (° C.) | M + H⁺ |
|---|---|---|---|---|---|---|
| 220 | 3-methylpyridyl | 5-methylthiophene-CH2-N(C=O)N(Me)- fused to 6-methylbenzo (dioxo) | H | / | / | 508 |
| 221 Ex 16 | 3-methylbenzoic acid | 4-fluorophenoxyethyl-N(C=O)N(Pr)- fused to benzo (dioxo) | H | Na | / | 607 |
| 222 | 3-methylbenzoic acid | 5-methylthiophene-CH2-N(C=O)N(Pr)- fused to 6-methylbenzo (dioxo) | H | / | / | 536 |

TABLE NO 1-continued

| No. | R<sub>1</sub> | | R<sub>4</sub> | Salt | M.p. (° C.) | M + H<sup>+</sup> |
|---|---|---|---|---|---|---|
| 223 | 3-methylbenzoic acid | 4-((morpholinoethoxy)phenyl)methyl quinazolinedione | H | Na | / | 645 |
| 224 | 3-methylbenzoic acid | (5-methylthiophen-2-yl)methyl N-Pr methylquinazolinedione | H | Na | / | 579 |
| 225 | 2-fluoro-5-methylbenzoic acid | (4-fluorobenzyl) N-Pr methylquinazolinedione | H | Na | 313 | 595 |

TABLE NO 1-continued

| No. | R₁ | R₂, R₃ structure | R₄ | Salt | M.p. (° C.) | M + H⁺ |
|---|---|---|---|---|---|---|
| 226 | H | 3-methyl-1-(4-fluorobenzyl)-N-methyl quinazolinedione | H | / | / | 429 |
| 227 | 3-hydroxy-methylphenyl | 3-methyl-1-(4-fluorobenzyl)-N-propyl quinazolinedione | H | / | 146 | 549 |
| 228 | 3-acetylphenyl | 3-methyl-1-(4-fluorobenzyl)-N-propyl quinazolinedione | H | / | 227 | 575 |

TABLE NO 1-continued

| No. | R₁ | | R₄ | Salt | M.p. (° C.) | M + H⁺ |
|---|---|---|---|---|---|---|
| 229 | 3-methylphenyl-tetrazole | 4-fluorobenzyl, N-Me quinazolinedione, 6-methyl | H | / | / | 573 |
| 230 | 3-methylphenyl-tetrazole | 4-fluorobenzyl, N-Pr quinazolinedione, 6-methyl | H | / | / | 601 |
| 231 | 6-methylquinolin-3-yl | 4-fluorobenzyl, N-Me quinazolinedione, 6-methyl | H | HCl | 290 | 556 |

TABLE NO 1-continued

| No. | R₁ | R₃ | R₄ | Salt | M.p. (° C.) | M + H⁺ |
|---|---|---|---|---|---|---|
| 232 | [pyrimidine with N(CH₃)₂] | [4-fluorobenzyl, propyl, methyl-substituted quinazolinedione] | H | / | / | 578 |
| 233 | [amidoxime on m-tolyl] | [4-fluorobenzyl, propyl, methyl-substituted quinazolinedione] | H | / | / | 591 |
| 234 | [amidoxime on m-tolyl] | [4-fluorobenzyl, methyl, methyl-substituted quinazolinedione] | H | / | / | 563 |

TABLE NO 1-continued

| No. | R₁ | | R₄ | Salt | M.p. (° C.) | M + H⁺ |
|---|---|---|---|---|---|---|
| 235 | 4-methylphenoxymethyl with COOH | N-(4-fluorobenzyl), N'-Pr quinazolinedione with 6-Me | H | Na | 217 | 607 |
| 236 | 3-methylbenzyl with OtBu | N-(4-fluorobenzyl), N'-Me quinazolinedione with 6-Me | H | / | 182 | 591 |
| 237 | 3-methylbenzyl with OtBu | N-(4-fluorobenzyl), N'-Pr quinazolinedione with 6-Me | H | / | 108 | 619 |

TABLE NO 1-continued

| No. | R₁ | | R₄ | Salt | M.p. (° C.) | M + H⁺ |
|---|---|---|---|---|---|---|
| 238 | dimethylamino-pyrimidinyl | N-isopentyl, N'-Me methyl-quinazolinedione | H | / | / | 526 |
| 239 | dimethylamino-pyrimidinyl | N-isopentyl, N'-Pr methyl-quinazolinedione | H | / | / | 554 |
| 240 | methyl-pyridinonyl | N-isopentyl, N'-Pr methyl-quinazolinedione | H | / | 285 | 550 |

TABLE NO 1-continued

| No. | R₁ | (structure) | R₄ | Salt | M.p. (° C.) | M + H⁺ |
|---|---|---|---|---|---|---|
| 241 | (dimethylamino-pyrimidinyl) | (methyl-quinazolinedione with morpholinoethyl and isohexyl) | H | / | / | 625 |
| 242 | (3-methylphenyl-oxadiazolone) | (methyl-quinazolinedione with 4-fluorobenzyl and n-propyl) | H | / | / | 617 |

TABLE NO 1-continued

| No. | R₁ | | R₄ | Salt | M.p. (°C.) | M + H⁺ |
|---|---|---|---|---|---|---|
| 243 | 3-(3-methylphenyl)-1,2,4-oxadiazol-5(4H)-one | 4-fluorobenzyl / methyl / 6-methyl quinazoline-2,4-dione | H | / | / | 589 |
| 244 | CH=CH-COOH (but-2-enoic acid) | 4-fluorobenzyl / propyl / 6-methyl quinazoline-2,4-dione | H | Na | 342 | 527 |
| 245 | 2-(dimethylamino)pyrimidin-5-yl | 2-cyclopentylethyl / propyl / 6-methyl quinazoline-2,4-dione | H | / | / | 566 |

TABLE NO 1-continued

| No. | R₁ | R₃ | R₄ | Salt | M.p. (° C.) | M + H⁺ |
|---|---|---|---|---|---|---|
| 246 | COOH-butyl | 5-methyl-3-(4-fluorobenzyl)-quinazoline-2,4-dione (N-Me) | H | Na | 349 | 501 |
| 247 | 5-methyl-2-morpholinopyrazine | 5-methyl-3-(4-fluorobenzyl)-quinazoline-2,4-dione (N-Me) | H | HCl | / | 592 |
| 248 | 3-methyl-1H-pyrazole | 5-methyl-3-(4-fluorobenzyl)-quinazoline-2,4-dione (N-Me) | H | HCl | / | 495 |

TABLE NO 1-continued
| No. | R₁ | | R₄ | Salt | M.p. (°C.) | M + H⁺ |
|---|---|---|---|---|---|---|
| 249 | 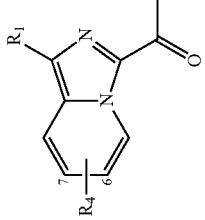 | 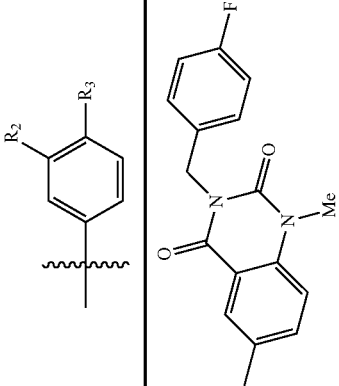 | H | HCl | / | 551 |
| 250 | 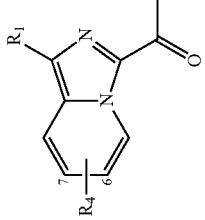 | 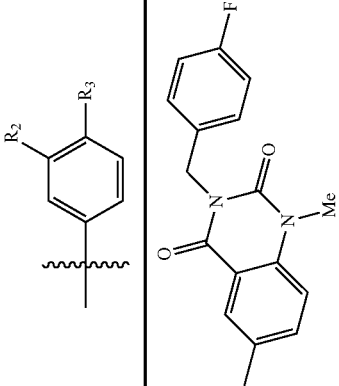 | H | HCl | / | 520 |
| 251 | 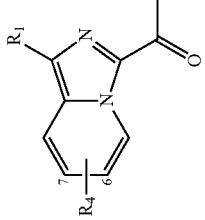 | 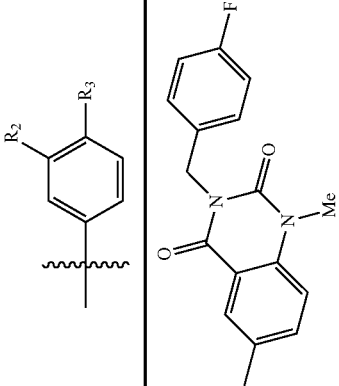 | H | HCl | / | 495 |

TABLE NO 1-continued

| No. | R₁ | | R₄ | Salt | M.p. (° C.) | M + H⁺ |
|---|---|---|---|---|---|---|
| 250 | 4-tert-butylphenyl | 4-fluorobenzyl-6-methylquinazoline-2,4-dione | H | HCl | / | 561 |
| 251 | 2-methyl-6-(trifluoromethoxy)phenyl | 4-fluorobenzyl-6-methylquinazoline-2,4-dione | H | HCl | / | 589 |

TABLE NO 1-continued

| No. | R₁ | | R₄ | Salt | M.p. (° C.) | M + H⁺ |
|---|---|---|---|---|---|---|
| 252 | 2-methyl-imidazole-4-yl-phenyl | 3-(4-fluorobenzyl)-1-methyl-6-methyl-quinazoline-2,4-dione | H | HCl | / | 602 |
| 253 | 2-methyl-5-methoxy-phenyl (Me, OMe) | 3-(4-fluorobenzyl)-1-methyl-6-methyl-quinazoline-2,4-dione | H | HCl | / | 549 |
| 254 | 2,5-dimethoxy-phenyl (OMe, OMe) | 3-(4-fluorobenzyl)-1-methyl-6-methyl-quinazoline-2,4-dione | H | HCl | / | 565 |

TABLE NO 1-continued

| No. | R₁ | R₂ R₃ (attachment) | R₄ | Salt | M.p. (° C.) | M + H⁺ |
|---|---|---|---|---|---|---|
| 255 | 4-Cl-phenyl | 3-(6-methyl-1-(4-fluorobenzyl)-N-Me-quinazoline-2,4-dione) | H | HCl | / | 539 |
| 256 | 2-OMe-4-methyl-phenyl (with F) | 3-(6-methyl-1-(4-fluorobenzyl)-N-Me-quinazoline-2,4-dione) | H | HCl | / | 553 |
| 257 | 2,3-diF-4-methyl-phenyl | 3-(6-methyl-1-(4-fluorobenzyl)-N-Me-quinazoline-2,4-dione) | H | HCl | / | 541 |

TABLE NO 1-continued

| No. | R₁ | (structure) | R₄ | Salt | M.p. (° C.) | M + H⁺ |
|---|---|---|---|---|---|---|
| 258 | 2-(4-methylphenyl)furan | 3-(4-fluorobenzyl)-1-methyl-6-methyl-quinazoline-2,4-dione | H | HCl | / | 571 |
| 259 | 6-methylimidazo[1,2-a]pyridine | 3-(4-fluorobenzyl)-1-methyl-6-methyl-quinazoline-2,4-dione | H | HCl | / | 545 |
| 260 | 7-methylindole | 3-(4-fluorobenzyl)-1-methyl-6-methyl-quinazoline-2,4-dione | H | HCl | / | 544 |

TABLE NO 1-continued

| No. | R₁ | | R₄ | Salt | M.p. (° C.) | M + H⁺ |
|---|---|---|---|---|---|---|
| 261 | 5-methyl-2-(piperidin-1-yl)pyrimidine | 3-(4-fluorobenzyl)-1-methyl-6-methylquinazoline-2,4-dione | H | HCl | / | 590 |
| 262 | 4-(OtBu-methyl)phenyl | 3-(4-fluorobenzyl)-1-methyl-6-methylquinazoline-2,4-dione | H | HCl | / | 591 |
| 263 | 3-chloro-2-fluoro-5-methylphenyl | 3-(4-fluorobenzyl)-1-methyl-6-methylquinazoline-2,4-dione | H | HCl | / | 557 |

TABLE NO 1-continued

| No. | R₁ | | R₄ | Salt | M.p. (° C.) | M + H⁺ |
|---|---|---|---|---|---|---|
| 264 | 2-OMe, 5-MeO, 4-Me pyrimidine | 3-(4-fluorobenzyl)-1-methyl-7-methyl-quinazoline-2,4-dione | H | HCl | / | 567 |
| 265 | 2,4-difluoro-methylphenyl | 3-(4-fluorobenzyl)-1-methyl-7-methyl-quinazoline-2,4-dione | H | HCl | / | 541 |
| 266 | 4-methyl-benzo[d][1,3]dioxole | 3-(4-fluorobenzyl)-1-methyl-7-methyl-quinazoline-2,4-dione | H | HCl | / | 549 |

TABLE NO 1-continued (I)

| No. | R₁ | R₂, R₃ substituent | R₄ | Salt | M.p. (° C.) | M + H⁺ |
|---|---|---|---|---|---|---|
| 267 | 4-OCF₃-phenyl-methyl | 3-(4-fluorobenzyl)-1-methyl-6-methyl-quinazoline-2,4-dione | H | HCl | / | 589 |
| 268 | N-benzyl-3-methylbenzamide | 3-(4-fluorobenzyl)-1-methyl-6-methyl-quinazoline-2,4-dione | H | HCl | / | 638 |
| 269 | 2-methylbenzofuran | 3-(4-fluorobenzyl)-1-methyl-6-methyl-quinazoline-2,4-dione | H | HCl | / | 545 |

TABLE NO 1-continued

| No. | R₁ | | R₄ | Salt | M.p. (° C.) | M + H⁺ |
|---|---|---|---|---|---|---|
| 270 | 8-methylquinolin-yl | 3-({1-[(4-fluorophenyl)methyl]-N-methyl-dioxo-6-methylquinazoline}) | H | HCl | / | 556 |
| 271 | 4-(1-isopropylpiperazin-4-yl)-5-methylpyridin-2-yl | 3-({1-[(4-fluorophenyl)methyl]-N-methyl-dioxo-6-methylquinazoline}) | H | HCl | / | 632 |
| 272 | 3,4-dimethyl-1H-pyrazol-5-yl | 3-({1-[(4-fluorophenyl)methyl]-N-methyl-dioxo-6-methylquinazoline}) | H | HCl | / | 509 |

TABLE NO 1-continued

| No. | R₁ | | R₄ | Salt | M.p. (° C.) | M + H⁺ |
|---|---|---|---|---|---|---|
| 273 | 5-methylthiophene-2-COOH | 3-(4-fluorobenzyl)-1-methyl-6-methylquinazoline-2,4-dione | H | HCl | / | 555 |
| 274 | 4-methylquinoline | 3-(4-fluorobenzyl)-1-methyl-6-methylquinazoline-2,4-dione | H | HCl | / | 556 |
| 275 | 3-methyl-(trifluoromethyl)phenyl | 3-(4-fluorobenzyl)-1-methyl-6-methylquinazoline-2,4-dione | H | HCl | / | 573 |

TABLE NO 1-continued
| No. | R₁ | | R₄ | Salt | M.p. (°C.) | M + H⁺ |
|---|---|---|---|---|---|---|
| 276 | 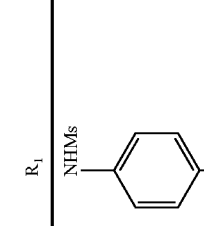 | 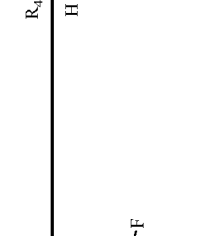 | H | HCl | / | 598 |
| 277 | 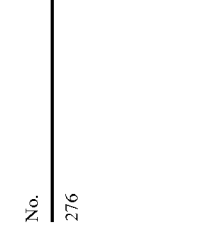 | 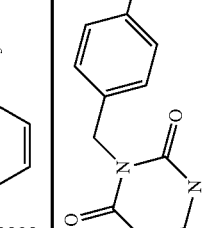 | H | HCl | / | 567 |
| 278 |  | 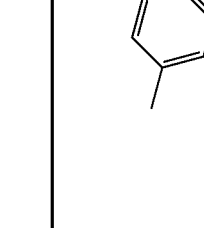 | H | HCl | / | 571 |

TABLE NO 1-continued

| No. | R₁ | | R₄ | Salt | M.p. (° C.) | M + H⁺ |
|---|---|---|---|---|---|---|
| 279 | 5-methyl-2-aminopyrimidin-yl | 3-(4-fluorobenzyl)-1-methyl-6-methylquinazoline-2,4-dione | H | HCl | / | 522 |
| 280 | 5-methyl-2-pyridone | 3-(4-fluorobenzyl)-1-methyl-6-methylquinazoline-2,4-dione | H | HCl | / | 522 |
| 281 | 5-methyl-2-(dimethylamino)pyrimidin-yl | 3-(4-fluorobenzyl)-1-methyl-6-methylquinazoline-2,4-dione | H | HCl | / | 550 |

TABLE NO 1-continued

| No. | R₁ | R₂ R₃ | R₄ | Salt | M.p. (°C.) | M + H⁺ |
|---|---|---|---|---|---|---|
| 282 | ureido-dimethyl-tolyl group | 4-fluorobenzyl-methyl-methyltoluquinazolinedione | H | HCl | / | 522 |
| 283 | (4-methylphenyl)acetic acid group | 4-fluorobenzyl-methyl-methyltoluquinazolinedione | H | HCl | / | 563 |
| 284 | 4-fluoro-3-methyl-5-methoxyphenyl | 4-fluorobenzyl-methyl-methyltoluquinazolinedione | H | HCl | / | 553 |

TABLE NO 1-continued

| No. | R₁ | | R₄ | Salt | M.p. (° C.) | M + H⁺ |
|---|---|---|---|---|---|---|
| 285 | 3-methylbenzyl-COOH | 4-fluorobenzyl uracil with methyl | H | HCl | / | 563 |
| 286 | 3-pyridyl | 2,6-dimethyl-7-methyl-4-quinolinone | H | / | / | 395 |
| 287 | 2-(dimethylamino)-5-pyrimidinyl | N,N-dimethylcarboxamide quinolinone | H | / | / | 510 |

TABLE NO 1-continued

| No. | R₁ | (structure) | R₄ | Salt | M.p. (° C.) | M + H⁺ |
|---|---|---|---|---|---|---|
| 288 | dimethylamino-pyrimidinyl | N,N,2-trimethyl-1-propyl-4-oxo-6-methylquinoline-3-carboxamide | H | / | / | 538 |
| 289 | 3-methylpyridyl | N,N,1,2-tetramethyl-4-oxo-6-methylquinoline-3-carboxamide | H | / | / | 466 |
| 290 | 3-methylbenzoic acid | 3-[2-(4-fluorophenoxy)ethyl]-1-methyl-6-methylquinazoline-2,4-dione | H | Na | / | 579 |

TABLE NO 1-continued

| No. | R₁ | R₂ R₃ | R₄ | Salt | M.p. (° C.) | M + H⁺ |
|---|---|---|---|---|---|---|
| 291 | (3-methylbenzoic acid structure) | (thiophene-methyl quinazolinedione structure) | H | Na | / | 551 |

The compounds according to the invention were subjected to pharmacological tests for determining their activity for the treatment of bladder cancer.

EXAMPLE 17

Evaluation of the Capacity of the FGF-R Antagonists to Inhibit Serum-induced Proliferation of Bladder Cancer Tumour Cells of TCC97-7 Type Carrying the Ser249Cys Mutation of FGF Receptor 3 and Demonstration of their Weak Cytotoxic Effect To do this, 2000 cells are seeded in the morning in 50 µl of complete medium (Ham-F/12, 1% FCS, 2 mM glutamine, non-essential amino acids, sodium pyruvate, 1% insulin/transferrin/selenium, hydrocortisone). In the evening, 50 µl of the various compounds are added at 0.02, 0.2, 2 or 20 µM after dilution in complete culture medium in order to obtain final concentrations of 0.01, 0.1, 1 and 10 µM. After 3 days, the cell proliferation is evaluated by measuring the number of nuclei at the bottom of each well corresponding to a number of cells. The nuclei are detected by means of labelling with Hoechst 33342 (Invitrogen, ref H3570). 100 µl of Hoechst 33342 diluted to 1/5000$^{th}$ in PBS are added to each well for 30 min at ambient temperature on non-fixed cells. The nuclei are detected by fluorescence at 350 nm at ×2 magnification with an Operetta (PerkinElmer) using the Acapella (PerkinElmer) imaging software and analysed using the Columbus (PerkinElmer) image analysis software. The percentage inhibition of the cell proliferation is calculated by considering the number of nuclei present in the wells in which the TCC97-7 cells are cultured in the absence of FGF-R antagonists to be 0% inhibition. 100% inhibition would correspond to a well no longer containing cells. The compounds of the present invention are considered to be active from the moment an inhibition of greater than or equal to 20% at the dose of less than or equal to 10 µM is observed.

In parallel to their antiproliferative capacity, the potential cytotoxic effect of the FGF-R antagonists is measured by means of quantifying the number of cells of which the membranes are permeabilized. The appearance of pores in the plasma membrane of the cells corresponds to a state of cell death which enables the Hoechst 33342 to penetrate more easily into the cell. This is reflected by a very strong increase in the amount of fluorescence detected in the nuclei. The percentage of cells in a state of cell death is calculated by the ratio between the number of very fluorescent nuclei to the total number of nuclei, multiplied by 100. The observations are carried out in the same way as the quantification of the nuclei for the cell proliferation.

Thus, compounds 29, 49, 55, 71, 79, 108, 112, 116, 140, 148, 207, 220, 291, 221, 224, 226 and 232 are capable of inhibiting the proliferation of the TCC97-7 cells by more than 20% at the doses of 0.1, 1 or 10 µM. This inhibition is not the result of strong cytotoxicity since the number of permeable cells does not exceed 25% at the maximum dose of 10 µM (Table No. 2).

TABLE NO. 2

Evaluation of the compounds with regard to their capacity to inhibit the proliferation in the presence of serum of the TCC97-7 cell line and observation of their weak cytotoxic effect

| | Inhibition of proliferation (%) | | | | Cytotoxicity (% of permeable cells) | | | |
|---|---|---|---|---|---|---|---|---|
| | 0.01 µM | 0.1 µM | 1 µM | 10 µM | 0.01 µM | 0.1 µM | 1 µM | 10 µM |
| compound 29 | 6 | 9 | 45 | 71 | 3 | 3 | 8 | 17 |
| compound 49 | | 9 | 55 | 81 | 5 | 5 | 6 | 12 |
| compound 55 | 3 | −2 | 29 | 47 | 5 | 5 | 6 | 6 |
| compound 71 | 0 | 1 | 14 | 85 | 4 | 4 | 5 | 1 |
| compound 79 | 5 | 0 | 17 | 71 | 1 | 1 | 2 | 10 |
| compound 108 | −4 | −5 | 6 | 22 | 4 | 5 | 4 | 4 |
| compound 112 | 8 | 18 | 61 | 84 | 4 | 4 | 16 | 11 |
| compound 116 | −1 | −3 | 22 | 83 | 2 | 2 | 2 | 3 |
| compound 140 | 0 | −1 | −7 | 26 | 1 | 1 | 1 | 2 |
| compound 148 | 12 | 6 | 15 | 81 | 4 | 4 | 4 | 11 |
| compound 207 | 2 | 7 | 45 | 82 | 5 | 4 | 5 | 23 |
| compound 220 | 4 | 3 | 13 | 49 | 6 | 5 | 5 | 11 |
| compound 291 | 1 | 5 | 40 | 81 | 2 | 2 | 2 | 4 |
| compound 221 | 5 | 27 | 80 | 85 | 4 | 5 | 6 | 7 |
| compound 224 | 3 | 0 | 27 | 82 | 3 | 3 | 4 | 9 |
| compound 226 | 3 | 8 | 28 | 73 | 5 | 6 | 10 | 25 |
| compound 232 | −6 | 1 | 20 | 79 | 3 | 3 | 4 | 23 |

EXAMPLE 18

Evaluation of the Capacity of the FGF-R Antagonists to Reduce the ATP Content of TCC97-7 Bladder Cancer Cells Carrying the Ser249Cys Mutation of FGF Receptor 3, Cultured in a Serum-Supplemented Medium To do this, 3000 cells are seeded in 50 µl of complete medium (Ham-F/12, 1% FCS, mM glutamine, non-essential amino acids, sodium pyruvate, 1% insulin/transferrin/selenium, hydrocortisone). 16 hours later, 50 µl of the various compounds are added at 0.2, 2, 20 and 60 µM after dilution in complete culture medium in order to obtain final concentrations of 0.1, 1, 10 and 30 µM. After 3 days, the ATP content of the cells is measured using the Cell Titer-Glo® Luminescent Cell Viability Assay kit (Promega, France) according to the supplier's recommendations. The percentage inhibition of the amount of intracellular ATP is calculated by considering the ATP content of the cells cultured in the absence of antagonist to be 0% inhibition. 100% inhibition would correspond to a well in which the ATP content is zero. The compounds of the present invention are considered to be active from the moment an inhibition of greater than or equal to 20% at the dose of less than or equal to 30 µM is observed.

Thus, compounds 29, 49, 55, 71, 79, 112, 116, 148, 207, 220, 291, 221, 224, 226, 232 and 240 are capable of inhibiting the amount of intracellular ATP in the TCC97-7 cells by more than 20% at the doses of 1, 10 or 30 µM (Table No. 3).

TABLE 3 measurement of the inhibition of the amount of intracellular ATP in TCC97-7 cells cultured in the presence of serum and brought into contact with various compounds

| | Inhibition of the amount of intracellular ATP (%) | | | |
|---|---|---|---|---|
| | 0.1 µM | 1 µM | 10 µM | 30 µM |
| DMSO | | | | 7 |
| compound 29 | −4 | 8 | 24 | |
| compound 49 | −2 | 14 | 67 | |
| compound 55 | 11 | 17 | 57 | |
| compound 71 | −4 | −1 | 94 | |
| compound 79 | −6 | 7 | 72 | |
| compound 112 | −3 | 51 | 88 | |
| compound 116 | 6 | 9 | 95 | |
| compound 148 | 1 | 8 | 66 | |
| compound 207 | 10 | 23 | 62 | |
| compound 220 | 6 | 10 | 16 | 60 |
| compound 291 | 8 | 27 | 71 | |
| compound 221 | −2 | 7 | 73 | |
| compound 224 | −1 | 20 | 83 | |
| compound 226 | −1 | 5 | 41 | |
| compound 232 | 7 | 8 | 45 | |
| compound 240 | −2 | 7 | 4 | 53 |

EXAMPLE 19

Evaluation of the Capacity of the FGF-R Antagonists to Reduce the Phosphorylation of the Signalling Pathway Involving Erk and Controlling Proliferation of TCC97-7 Bladder Cancer Cells Carrying the Ser249Cys Mutation of FGF Receptor 3, Cultured in a Serum-Supplemented Medium To do this, 3×10$^5$ cells are seeded in 1.9 ml of complete medium (Ham-F/12, 1% FCS, 2 mM glutamine, non-essential amino acids, sodium pyruvate, 1% insulin/transferrin/selenium, hydrocortisone) in 6-well plates. 48 h later, 100 µl of the various compounds are added at 200 µM after dilution in serum-free culture medium in order to obtain a final concentration of 10 µM. After 4 h, the medium is drawn off, the cells are rinsed with cold PBS and 80 µl of RIPA buffer (Sigma, R0278) containing a cocktail of protease and phosphatase inhibitors (Pierce, 78440) is added to each well at 4° C. for 30 min. The protein lysates are then collected and centrifuged at 13 000 rpm, at 4° C., for 10 min. The supernatants are then separated by acrylamide gel electrophoresis (4-20%). After transfer onto a nitrocellulose membrane, the membranes are saturated for 1 h at ambient temperature in TBS, 0.05% Tween, 5% skimmed milk, and then incubated overnight at 4° C. in the presence of anti-phosphoErk (Cell Signaling Technology, 4377) or anti-GAPDH (Cell Signaling Technology, 5174) primary antibodies diluted to 1/1000$^{th}$ in TBS, 0.05% Tween, 0.1% BSA. The following day, after 3 washes with TBS, 0.05% Tween, the membranes are incubated for 3 h with secondary antibodies coupled to HRP (Cell Signaling Technology, 7074) diluted to 1/1000$^{th}$ in TBS, 0.05% Tween, 0.1% BSA. After visualization using the SuperSignal West Dura chemiluminescent substrate reagent (Pierce), the bands corresponding to the phosphorylation of Erk or to GADPH are quantified using a ChemiGenius (Syngene) analyser. The results are then expressed as percentage inhibition of the Erk phosphorylation detected in the DMSO control condition. The compounds of the present invention are considered to be active from the moment an inhibition of greater than or equal to 20% at the dose or less than or equal to 10 µM is observed.

Thus, compounds 49, 207, 221, 224 and 290 sont are capable of inhibiting Erk phosphorylation in TCC97-7 cells by more than 20% at the dose of 10 µM (Table No. 4).

TABLE 4 measurement of the inhibition of Erk phosphorylation in TCC97-7 cells cultured in the presence of serum and brought into contact with various compounds

| | Inhibition of Erk phosphorylation (%) 10 µM |
|---|---|
| DMSO | 0 |
| compound 207 | 39 |
| compound 290 | 53 |
| compound 49 | 24 |
| compound 224 | 44 |
| compound 221 | 93 |

According to another of its aspects, the present invention relates to the use of pharmaceutical compositions comprising, as active ingredient, a compound of formula (I) for the treatment of bladder cancer. These pharmaceutical compositions contain an effective dose of at least one compound according to formula (I), or a pharmaceutically acceptable salt, and also at least one pharmaceutically acceptable excipient, used for the treatment of bladder cancer. Said excipients are chosen, according to the pharmaceutical form and the mode of administration desired, from the usual excipients which are known to those skilled in the art.

In the pharmaceutical compositions for oral, sublingual, subcutaneous, intramuscular, intravenous, topical, local, intratracheal, intranasal, transdermal, intravesical or rectal administration, the active ingredient of formula (I) above, or its optional salt, solvate or hydrate, can be administered in unit administration form, as a mixture with conventional pharmaceutical excipients, to animals or to human beings for the prophylaxis or treatment of the abovementioned disorders or diseases.

The appropriate unit administration forms include oral forms, such as tablets, soft or hard gel capsules, powders, granules and oral solutions or suspensions, sublingual, buccal, intratracheal, intraocular and intranasal administration forms, forms of administration by inhalation, topical, transdermal, subcutaneous, intramuscular, intravesical or intravenous administration forms, rectal administration forms, and implants. For topical application, the compounds according to formula (I) can be used in creams, gels, ointments or lotions.

The pharmaceutical compositions according to the use of the present invention are preferably administered orally.

By way of example, a unit administration form of a compound according to the invention in tablet form may comprise the following constituents:

| FGF receptor inhibitor compound | 50.0 mg |
|---|---|
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

The present invention also relates to a pharmaceutical composition as defined above, as a medicament for the treatment of bladder cancer.

A compound of formula (I) according to the use of the present invention can be administered alone or in combination with one or more compound(s) having an anti-angiogenic activity or with one or more cytotoxic compound(s) (chemotherapy), or else in combination with a radiation treatment. Thus, a subject of the present invention is also the use of a compound of formula (I), as defined above, in combination with one or more anti-cancer active ingredient(s) and/or with radiotherapy.

The compositions according to the invention, for oral administration, contain recommended doses of from 0.01 to 700 mg. There may be particular cases where higher or lower dosages are appropriate; such dosages do not depart from the context of the invention.

According to the usual practice, the dosage appropriate for each patient is determined by the physician according to the mode of administration and the age, weight and response of the patient, and also according to the degree of progression of the disease.

According to another of its aspects, the present invention also relates to a method for treating bladder cancer, which comprises the administration, to a patient, of an effective dose of a compound according to the invention, or a pharmaceutically acceptable salt thereof.

The invention claimed is:

1. A method for treating bladder cancer comprising administering to a subject in need thereof a compound selected from the group consisting of:
   3-[3-(2,4-dioxo-3-propyl-1,2,3,4-tetrahydroquinazoline-6-carbonyl)imidazo[1,5-a]pyridin-1-yl]benzamide;
   3-{3-[3-(4-fluorobenzyl)-1-methyl-2,4-dioxo-1,2,3,4-tetrahydroquinazoline-6-carbonyl]imidazo[1,5-a]pyridin-1-yl}benzoic acid;
   3-[3-(2-methyl-4-oxo-3-propyl-3,4-dihydroquinazoline-6-carbonyl)imidazo[1,5-a]pyridin-1-yl]benzamide;
   3-{3-[3-(4-fluorobenzyl)-1-methoxymethyl-2,4-dioxo-1,2,3,4-tetrahydroquinazoline-6-carbonyl]imidazo[1,5-a]pyridin-1-yl}benzoic acid;
   3-{3-[3-(4-fluorobenzyl)-1-methyl-2,4-dioxo-1,2,3,4-tetrahydroquinazoline-6-carbonyl]imidazo[1,5-a]pyridin-1-yl}benzoic acid ethyl ester;
   3-{3-[3-(3-fluorobenzyl)-1-methyl-2,4-dioxo-1,2,3,4-tetrahydroquinazoline-6-carbonyl]imidazo[1,5-a]pyridin-1-yl}benzamide;
   3-(4-fluorobenzyl)-1-methyl-6-(1-pyridin-3-ylimidazo[1,5-a]pyridine-3-carbonyl)-1H-quinazoline-2,4-dione;
   N-(2-dimethylaminoethyl)-3-{3-[3-(4-fluorobenzyl)-1-methyl-2,4-dioxo-1,2,3,4-tetrahydroquinazoline-6-carbonyl]imidazo[1,5-a]pyridin-1-yl}benzamide;
   3-(4-fluorobenzyl)-1-methyl-6-{1-[3-(5-methyl-[1,3,4]oxadiazol-2-yl)phenyl]imidazo[1,5-a]pyridine-3-carbonyl}-1H-quinazoline-2,4-dione;
   3-(3-{3-[2-(4-fluorophenyl)ethyl]-1-methyl-2,4-dioxo-1,2,3,4-tetrahydroquinazoline-6-carbonyl}imidazo[1,5-a]pyridin-1-yl)benzoic acid;
   3-{3-[3-(4-methylpentyl)-2,4-dioxo-1-propyl-1,2,3,4-tetrahydroquinazoline-6-carbonyl]imidazo[1,5-a]pyridin-1-yl}benzoic acid;
   1-methyl-3-(5-methylthiophen-2-ylmethyl)-6-(1-pyridin-3-ylimidazo[1,5-a]pyridine-3-carbonyl)-1H-quinazoline-2,4-dione;
   3-(3-(1-methyl-3-((5-methylthiophen-2-yl)methyl)-2,4-dioxo-1,2,3,4-tetrahydroquinazoline-6-carbonyl)imidazo[1,5-a]pyridin-1-yl)benzoic acid;
   3-(3-{3-[2-(4-fluorophenoxy)ethyl]-2,4-dioxo-1-propyl-1,2,3,4-tetrahydroquinazoline-6-carbonyl}imidazo[1,5-a]pyridin-1-yl)benzoic acid;
   3-{3-[3-(5-methylthiophen-2-ylmethyl)-2,4-dioxo-1-propyl-1,2,3,4-tetrahydroquinazoline-6-carbonyl]imidazo[1,5-a]pyridin-1-yl}benzoic acid;
   3-(4-fluorobenzyl)-6-(imidazo[1,5-a]pyridine-3-carbonyl)-1-methyl-1H-quinazoline-2,4-dione; and
   6-(1-(2-(dimethylamino)pyrimidin-5-yl)imidazo[1,5-a]pyridine-3-carbonyl)-3-(4-fluorobenzyl)-1-propylquinazoline-2,4-dione,
   or a pharmaceutically acceptable salt thereof.

2. The method according to claim 1, wherein the compound is in the form of a sodium salt or a hydrochloride salt.

3. A method for treating bladder cancer, comprising administering to a subject in need thereof a compound having the structure:

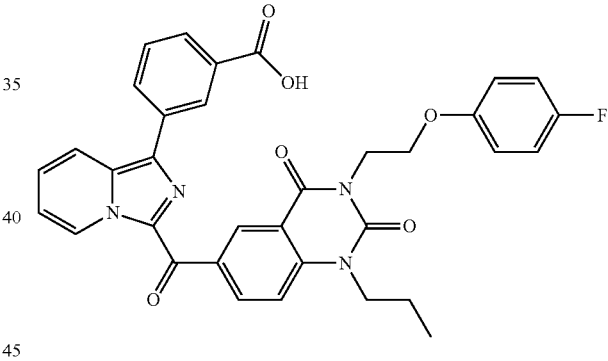

or a pharmaceutically acceptable salt thereof.

4. The method according to claim 3, wherein the compound is in the form of a sodium salt.

* * * * *